US011439612B2

(12) United States Patent
Levin et al.

(10) Patent No.: US 11,439,612 B2
(45) Date of Patent: Sep. 13, 2022

(54) FORMULATIONS FOR ADMINISTRATION OF EFLORNITHINE

(71) Applicant: Orbus Therapeutics, Inc., Palo Alto, CA (US)

(72) Inventors: Victor A. Levin, Palo Alto, CA (US); Noymi Yam, Palo Alto, CA (US); Alexander Vakoula, Palo Alto, CA (US)

(73) Assignee: ORBUS THERAPEUTICS, INC., Palo Alto, CA (US)

( * ) Notice: Subject to any disclaimer, the term of this patent is extended or adjusted under 35 U.S.C. 154(b) by 0 days.

(21) Appl. No.: 17/002,117

(22) Filed: Aug. 25, 2020

(65) Prior Publication Data

US 2021/0038549 A1 Feb. 11, 2021

Related U.S. Application Data

(63) Continuation of application No. 16/339,664, filed as application No. PCT/US2017/054450 on Sep. 29, 2017, now Pat. No. 10,786,470.

(60) Provisional application No. 62/404,981, filed on Oct. 6, 2016.

(51) Int. Cl.
| A61K 31/197 | (2006.01) |
| A61K 47/26 | (2006.01) |
| A61P 43/00 | (2006.01) |
| A61P 35/00 | (2006.01) |
| C07C 229/00 | (2006.01) |
| A61K 9/00 | (2006.01) |
| A61P 25/00 | (2006.01) |

(52) U.S. Cl.
CPC .......... *A61K 31/197* (2013.01); *A61K 9/0053* (2013.01); *A61K 9/0095* (2013.01); *A61K 47/26* (2013.01); *A61P 25/00* (2018.01); *A61P 35/00* (2018.01); *A61P 43/00* (2018.01); *C07C 229/00* (2013.01)

(58) Field of Classification Search
None
See application file for complete search history.

(56) References Cited

U.S. PATENT DOCUMENTS

| 4,330,559 | A | 5/1982 | Bey et al. |
| 5,614,557 | A | 3/1997 | Bey et al. |
| 6,199,698 | B1 * | 3/2001 | Hetrick .............. B65D 75/5855 |
| | | | 206/532 |
| 6,258,845 | B1 | 7/2001 | Gerner et al. |
| 6,277,411 | B1 | 8/2001 | Shaked et al. |
| 6,602,910 | B2 | 8/2003 | Levenson et al. |
| 6,653,351 | B2 | 11/2003 | Levin |
| 6,936,318 | B2 * | 8/2005 | Dent ...................... B32B 15/20 |
| | | | 428/35.9 |
| 6,998,502 | B1 | 2/2006 | Majeed et al. |
| 7,345,196 | B1 | 3/2008 | Majeed et al. |
| 9,072,778 | B2 | 7/2015 | Bachmann |
| 10,786,470 | B2 | 9/2020 | Levin et al. |
| 10,945,981 | B2 * | 3/2021 | Gerner ................. A61K 31/192 |
| 2002/0110590 | A1 | 8/2002 | Shaked et al. |
| 2003/0040526 | A1 | 2/2003 | Levin |
| 2003/0053973 | A1 | 3/2003 | Chou et al. |
| 2007/0246057 | A1 | 10/2007 | Muller |
| 2008/0027023 | A1 | 1/2008 | Ellervik et al. |
| 2010/0076009 | A1 | 3/2010 | Towner et al. |
| 2017/0273926 | A1 | 9/2017 | Levin |
| 2019/0091187 | A1 | 3/2019 | Levin |
| 2019/0133985 | A1 | 5/2019 | Levin |

FOREIGN PATENT DOCUMENTS

| CN | 1346282 A | 4/2002 |
| JP | 2004509845 A | 4/2004 |
| JP | 2005505528 A | 2/2005 |
| JP | 2012501652 A | 1/2012 |
| JP | 2013516456 A | 5/2013 |
| JP | 2018536707 A | 12/2018 |
| WO | WO-0168076 A2 | 9/2001 |

OTHER PUBLICATIONS

Obaleye et al., "Synthesis, Characterization, Crystal Structure and Antimicrobial Evaluation of a Novel—M-X-M-X—Type Infinite Chain 1D Cu(II) Complex with Eflornithine Hydrochloride Hydrate as Ligand", 2014, J. Inorg. Organomet. Polym., 24(5), pp. 827-835. (doi.org/10.1007/s10904-014-0052-x) (Year: 2014).*
Kumar et al., "A method to improve the efficacy of topical eflornithine hydrochloride cream", 2016, Drug Delivery, 23(5), pp. 1495-1501. (DOI: 10.3109/10717544.2014.951746) (Year: 2016).*
Carbone et al. Bioavailability Study of Oral Liquid and Tablet Forms of α-Difluoromethylornithine. Clinical Cancer Research, vol. 6. pp. 3850-3854 (Oct. 2000).
Co-pending U.S. Appl. No. 17/016,821, inventor Levin; Victor A., filed Sep. 10, 2020.
Co-pending U.S. Appl. No. 17/079,197, inventor Levin; Victor A., filed Oct. 23, 2020.
U.S. Appl. No. 16/087,195 Office Action dated Sep. 17, 2020.
U.S. Appl. No. 16/339,664 Ex Parte Quayle Action dated Jun. 25, 2020.
U.S. Appl. No. 16/339,664 Notice of Allowance dated Jul. 31, 2020.
U.S. Appl. No. 16/339,664 Notice of Allowance dated Sep. 4, 2020.

(Continued)

*Primary Examiner* — My-Chau T. Tran

(74) *Attorney, Agent, or Firm* — Wilson Sonsini Goodrich & Rosati

(57) ABSTRACT

Eflornithine is an agent that can be used to treat glioma, especially glioma of WHO Grade II or Grade III such as anaplastic glioma. Eflornithine can suppress or prevent mutations in glioma which can cause the glioma to progress to a higher grade. The present invention describes pharmaceutical compositions that contain eflornithine or a derivative, analog, or prodrug thereof. The pharmaceutical compositions can be prepared in a number of dosage forms and may contain another therapeutically active agent or an agent that enhances the therapeutic activity of the elformithine or the derivative, analog, or prodrug thereof. The present invention also describes a kit that includes dosage forms of pharmaceutical compositions according to the present invention.

16 Claims, 3 Drawing Sheets

Specification includes a Sequence Listing.

(56) References Cited

OTHER PUBLICATIONS

Chamberlain et al. Salvage Chemotherapy with Cyclophosphamide for Recurrent Temozolomide-Refractory Anaplastic Astrocytoma. Cancer 106(1):172-179 (2006). Published online Dec. 1, 2005.
Co-pending U.S. Appl. No. 17/234,289, inventor Levin; Victor A., filed Apr. 19, 2021.
Co-pending U.S. Appl. No. 17/337,846, inventor Levin; Victor A., filed Jun. 3, 2021.
Killela et al. The genetic landscape of anaplastic astrocytoma. Oncotarget. Mar. 2014; 5(6):1452-1457. Published online Oct. 16, 2013. doi: 10.18632/oncotarget.1505.
U.S. Appl. No. 16/087,195 Office Action dated Jan. 27, 2021.
Bachmann et al., "Clinical Applications of Polyamine-Based Therapeutics", Polyamine Drug Discovery, (P.M. Woster & R.A. Casero, Jr., eds., RSC Publishing, 1992), ch. 11, pp. 257-276, 20 Pages.
Bartholeyns, "Treatment of Metastatic Lewis Lung Carcinoma with dl-a-Difluoromethylornithine", European Journal of Clinical Oncology, Apr. 1983, vol. 19, No. 4, pp. 567-572, 6 Pages.
Bristol-Myers Squibb Labeling VANIQA (Jul. 27, 2000). 10 pages.
Buckner et al., "Phase II Trial of Recombinant Interferon-Alpha-2a and Eflornithine in Patients with Recurrent Glioma", Journal of Neuro-Oncology, Jan. 1998, vol. 36, No. 1, pp. 65-70, 6 Pages.
Cohen et al., "Effect of Difluoromethylornithine on the Antiglioma Therapeutic Efficacy of Infra-Arterial BCNU", Journal of neurosurgery, Nov. 1986, vol. 65, No. 5, pp. 671-678, 8 Pages.
Compound Summary: Vaniqa. PubChem CID: 441361. National Center for Biotechnology Information. Accessed Jun. 21, 2020 from: https://pubchem.ncbi.nlm.nih.gov/compound/441361. Created Jun. 24, 2005. 29 pages.
Co-pending U.S. Appl. No. 16/748,581, inventor Levin; Victor A., filed Jan. 21, 2020.
Co-pending U.S. Appl. No. 16/812,633, inventor Levin; Victor A., filed Mar. 9, 2020.
EP17770846.8 Extended European Search Report dated Oct. 14, 2019.
EP17858939.6 Extended European Search Report dated Apr. 14, 2020.
Hayes et al., "Polyamine-Blocking Therapy Reverses Immunosuppression in the Tumor Microenvironment", Cancer Immunol. Research, Mar. 2014, retrieved on Jul. 18, 2016 from http://cancerimmunolres.aacrjournals.org/content/2/3/274.full.pdf, 13 Pages.
Koomoa et al., "Ornithine DecarboxylaseInhibition by a-Difluoromethylornithine Activates Opposing Signaling Pathways via Phosphorylation of Both Akt/Protein Kinase B and p27kip1 in Neuroblastoma", Cancer Research Center of Hawaii, Dec. 1, 2008, retrieved on Jul. 18, 2016 from http://citeseerx.ist.psu.edu/viewdoc/download;sessionid=DB165269FD2A8A1F82DC6C035292CE11?doi=10.1.1.585.4781&rep=rep1&ttype=pdf, 7 Pages.
Levin et al. No. 49. Final report for evaluable patients treated on DM92-035, Phase III randomized study of post-irradiation PCV versus DFMO-PCV, for anaplastic gliomas (AG). Neuro-Oncology 14(Suppl 6):vi74-vi75 (Oct. 2012).
Levin et al. Phase III Randomized Study of Postradiotherapy Chemotherapy with α-Difluoromethylornithine-Procarbazine, N-(2-Chloroethyl)-N'-cyclohexyl-N-nitrosurea, Vincristine (DFMO-PCV) Versus PCV for Glioblastoma Multiforme. Clinical Cancer Research 6(10):3878-3884 (Oct. 2000).
Levin et al. Phase I-II Study of Eflornithine and Mitoguazone Combined in the Treatment of Recurrent Primary Brain Tumors. Cancer Treatment Reports 71(5):459-464 (1987).
Levin et al. Treatment of Recurrent Gliomas With Eflornithine. Journal of the National Cancer Institute 84(18):1432-1437 (Sep. 16, 1992).
Marton et al., "Potentiation of the Antitumor Therapeutic Effects of 1,3-Bis(2-chloroethyl)-1-Nitrosourea by a-Difluoromethylornithine an Ornithine Decarboxylase Inhibitor", Cancer Research, Nov. 1981, vol. 41, retrieved on Jul. 18, 2016 from http://cancerres.aacrjournals.org/content/canres/41/11_Part_1/4426.full.pdf, 6 Pages.
M. Prados et al., "Treatment of Recurrent Gliomas with 1,3-Bis(2-Chloroethyl)-1-Nitrosourea and a-Difluoromethylornithine" Neurosurgery, Jun. 1989, vol. 24, No. 6, pp. 806-809, 4 Pages.
National Center for Biotechnology Information. PubChem Database. Eflornithine, CID-3009, https://pubchem.ncbi.nlm.nih.gov/compound/Eflornithine (create date Sep. 16, 2004; accessed on Apr. 1, 2020).
PCT/US2017/022718 International Preliminary Report on Patentability dated May 25, 2018.
PCT/US2017/022718 International Search Report and Written Opinion dated Jun. 2, 2017.
PCT/US2017/054450 International Preliminary Report on Patentability dated Oct. 29, 2018.
PCT/US2017/054450 International Search Report and Written Opinion dated Dec. 14, 2017.
Samal et al., "AMXT-1501, a Novel Polyamine Transport Inhibitor Synergizes with DFMO in Inhibiting Neuroblastoma Cell Proliferation by Targeting Both Ornithine Decarboxylase and Polyamine Transport", International Journal of Cancer, 2013, vol. 133, retrieved on Jul. 18, 2016 from http://onlinelibrary.wiley.com/doi/10.1002/ijc.28139/pdf, 11 Pages.
Siimes et al., "Synergistic Action of Two Polyamine Metabolites Leads to a Rapid Therapeutic Response in Childhood Leukemia", International Journal of Cancer, 1981, vol. 28, No. 5, pp. 567-570, 4 Pages.
U.S. Appl. No. 15/218,149 Office Action dated Jan. 11, 2017.
U.S. Appl. No. 15/218,149 Office Action dated Sep. 8, 2017.
U.S. Appl. No. 15/218,149 Office Action dated May 22, 2018.
U.S. Appl. No. 15/218,149 Office Action dated May 24, 2019.
U.S. Appl. No. 15/218,149 Office Action dated Nov. 26, 2018.
U.S. Appl. No. 15/218,149 Office Action dated Sep. 10, 2019.
U.S. Appl. No. 16/087,195 Office Action dated May 21, 2020.
U.S. Appl. No. 16/087,195 Office Action dated Feb. 13, 2020.
V.A. Levin et al., "CNS Toxicity and CSF Pharmacokinetics of Intraventricular DFMO and MGBG in Beagle Dogs," Cancer Chemother. Pharmacol. 13: 200-205 (1984).
V.A. Levin et al., "Phase III Randomized Study of Postradiotherapy Chemotherapy with Combination a-Difluoromethylornithine-PCV versus PCV for Anaplastic Gliomas," Clin. Cancer Res. 9: 981-990 (2003).
V.B. Grossie, Jr. et al., "Effect of Intravenous a-Difluoromethylornithine on the Polyamine Levels of Normal Tissue and a Transplantable Fibrosarcoma," Cancer Res. 47: 1836-1840 (1987).
W.D. Heston et al., "Growth Inhibition of a Prostate Tumor by a-Difluoromethylornithine and by Cyclophosphamide," Cancer Lett. 16: 71-79 (1982).
Co-pending U.S. Appl. No. 17/532,960, inventor Levin; Victor A., filed on Nov. 22, 2021.
Co-pending U.S. Appl. No. 17/575,408, inventor Levin; Victor A., filed on Jan. 13, 2022.
Co-pending U.S. Appl. No. 17/680,135, inventor Levin; Victor A., filed on Feb. 24, 2022.

\* cited by examiner

Illustration of the amount of Eflornithine used to "Seed" the Formulations (0.003 g)

Formulations Testing Schedule

Figure 3

Freezing Trend Analysis in "Seeded" Eflornithine Formulations

Nominal Logistic Fit for Seeding-2 Freezing Observations

Effect Summary

| Source | LogWorth | PValue |
|---|---|---|
| Eflornithine | 2.242 | 0.00573 |
| PG | 2.099 | 0.00796 |

Converged in Gradient, 6 iterations

Whole Model Test

| Model | -LogLikelihood | DF | ChiSquare | Prob>ChiSq |
|---|---|---|---|---|
| Difference | 6.170792 | 2 | 12.34158 | 0.0021* |
| Full | 7.591985 | | | |
| Reduced | 13.762776 | | | |

| | |
|---|---|
| RSquare (U) | 0.4484 |
| AICc | 22.684 |
| BIC | 24.1712 |
| Observations (or Sum Wgts) | 20 |

Parameter Estimates

| Term | Estimate | Std Error | ChiSquare | Prob>ChiSq |
|---|---|---|---|---|
| Intercept | 2.08231759 | 1.1954715 | 3.03 | 0.0815 |
| Eflornithine | -3.8144169 | 1.9296864 | 3.91 | 0.0481* |
| PG | 2.23584701 | 1.130155 | 3.91 | 0.0479* |

For log odds of n/y

SEQUENCE LISTING

<160> NUMBER OF SEQ ID NOS: 1

<210> SEQ ID NO 1
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Val Ala Pro Glu Glu His Pro Thr Leu Leu Thr Glu Ala Pro Leu Asn
1               5                   10                  15

Pro Lys

FORMULATIONS FOR ADMINISTRATION OF EFLORNITHINE

CROSS-REFERENCES TO RELATED APPLICATIONS

This application is a continuation of U.S. application Ser. No. 16/339,664, filed Apr. 4, 2019, which is a National Stage Entry of International Application No. PCT/US2017/054450, filed Sep. 29, 2017, which claims the benefit of U.S. Provisional Patent Application No. 62/404,981, filed Oct. 6, 2016, each of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Mar. 16, 2022, is named 57339_703_301_SL.txt and is 676 bytes in size.

FIELD OF THE INVENTION

This invention is directed to formulations for administration of the anti-neoplastic agent eflornithine, particularly for treatment of gliomas.

BACKGROUND OF THE INVENTION

Glioma is one of the most common and serious forms of brain tumor. Gliomas are classified by cell type, by grade, and by location. Gliomas are generally named according to the specific type of cell with which they share histological features. These are not necessarily the cell types from which the glioma originated. The main types of glioma are: ependyoma (ependymal cells), astrocytoma (astrocytes), oligodendroglioma (oligodendrocytes), brainstem glioma (brain stem), optic nerve glioma (cells in or around the optic nerve), and mixed glioma (cells from different types of glia). Gliomas are further characterized according to their grade, generally stated according to the WHO classification. Grade I is the lowest grade with the least advanced disease and the best prognosis, and Grade I gliomas are generally considered benign. Grade II of the WHO classification is the next lowest grade. Gliomas of Grade II are well-differentiated and not anaplastic. Although these tend to exhibit benign tendencies and can be associated with a favorable prognosis, they have a tendency to recur and to increase in grade, and thus, in severity, over time. High-grade gliomas, Grades III and IV in the WHO classification, are undifferentiated or anaplastic and are clearly malignant. These grades carry the worst prognosis. Gliomas can also be classified according to their location, specifically whether they are above or below a membrane in the brain, the tentorium. The tentorium separates the cerebrum from the cerebellum. Supratentorial gliomas are more common in adults, while infratentorial gliomas are more common in children. Certain types of glioma, such as subependymoma or juvenile pyelocytic astrocytoma (JPA) tend to be non-invasive or much less invasive.

The symptoms of glioma generally depend on which part of the central nervous system is affected. Gliomas in the brain can cause headaches, vomiting, seizures, focal weakness, problems forming new memories, problems with speech, and cranial nerve disorders as a result of tumor growth. Gliomas of the optic nerve can cause visual disturbances or vision loss. Gliomas of the spinal cord can cause pain, weakness, or numbness in one or more extremities. Generally, gliomas do not metastasize through the bloodstream, but can spread through the cerebrospinal fluid and cause drop metastases in the spinal cord.

The exact causes of gliomas are not known. Certain hereditary genetic disorders such as type 1 or type 2 neurofibromatosis or tuberous sclerosis can predispose to their development. A number of oncogenes can be involved in glioma initiation and development. Many gliomas are infected with cytomegalovirus, which can accelerate their development. Germ-line (inherited) polymorphisms of the DNA repair genes ERCC1, ERCC2 (XPD) and XRCC1 can increase the risk of glioma. This indicates that altered or deficient repair of DNA damage can contribute to the formation of gliomas. Excess DNA damage can give rise to mutations through translesion synthesis. Furthermore, incomplete DNA repair can give rise to epigenetic alterations or epimutations. Such mutations and epimutations may provide a cell with a proliferative advantage which can then, by a process of natural selection, lead to progression to cancer. Epigenetic repression of DNA repair genes is often found in progression to sporadic glioblastoma. For instance, methylation of the DNA repair gene MGMT promoter was observed in a substantial fraction of glioblastomas. In addition, in some glioblastomas, the MGMT protein is deficient due to another type of epigenetic alteration. MGMT protein expression may also be reduced due to increased levels of a microRNA that inhibits the ability of the MGMT messenger RNA to produce the MGMT protein. It was found that, in glioblastomas without methylated MGMT promoters, that the level of microRNA miR-181d is inversely correlated with protein expression of MGMT and that the direct target of miR-181d is the MGMT mRNA 3'UTR. Epigenetic reductions in expression of another DNA repair protein, ERCC1, were found in many gliomas; in some cases, the reduction was due to reduced or absent ERCC1 protein expression was reduced or absent. In other cases, the reduction was due to methylation of the ERCC1 promoter. In a small number of cases, the reduction could have been due to epigenetic alterations in microRNAs that affect ERCC1 expression. When expression of DNA repair genes is reduced, DNA damage can accumulate in cells at increased levels. In gliomas, mutations frequently occur in the isocitrate dehydrogenase genes IDH1 and IDH2. These mutations may result in production of an excess metabolic intermediate, 2-hydroxyglutarate, which binds to catalytic sites in key enzymes that are important in altering histone and DNA promoter methylation. This may result in a DNA CpG island methylator phenotype (CIMP) that can cause promoter hypermethylation and concomitant silencing of tumor suppressor genes such as DNA repair genes MGMT and ERCC1. Additionally, mutations in IDH1 and IDH2 may cause increased oxidative stress and thus initiate increased oxidative damage to DNA.

Several acquired genetic mutations are commonly found in gliomas, including mutations in p53 and PTEN; the gene encoding PTEN may also be lost. These mutations can lead to overexpression of EGFR. However, hypermutation associated with gliomas is not confined to specific locations.

High-grade gliomas are highly vascular tumors and have a tendency to infiltrate. They have extensive areas of necrosis and hypoxia. Often, tumor growth causes a breakdown of the blood-brain barrier in the vicinity of the tumor. As a rule, high-grade gliomas almost always grow back even after complete surgical excision, so are commonly called recurrent cancer of the brain. In contrast, lower-grade gliomas typically grow relatively slowly and can be followed without the need for aggressive treatment unless they grow or cause symptoms.

Treatment for gliomas depends on the location, the cell type, and the grade of malignancy. A combined approach, including surgical resection, radiotherapy, and chemotherapy, is frequently employed. One therapeutic agent frequently employed is temozolomide, which can cross the blood-brain barrier and is frequently used in treatment of higher-grade gliomas. The angiogenic blocker bevacizumab, a monoclonal antibody, is also frequently used. However, there is increasing evidence that the use of temozolomide may itself induce mutations and worsen prognosis in a significant fraction of patients (B. E. Johnson et al., "Mutational Analysis Reveals the Origin and Therapy-Driven Evolution of Recurrent Glioma," *Science* 343: 189-193 (2014), incorporated herein by this reference). The potentially mutagenic effect of temozolomide must be taken into account in planning a course of treatment for glioma.

Gliomas are rarely curable. The prognosis for patients with high-grade gliomas is generally poor, and is especially so for older patients. Of 10,000 Americans diagnosed each year with malignant gliomas and based on CBTRUS (table 23, 2015 edition), about 57% are alive one year after diagnosis, 41% after two years, and only 31% at five years. Those with anaplastic astrocytoma have about 44% at two years and 28% at five years. Glioblastoma multiforme has a worse prognosis with a 37% one year survival and 15% two year survival after diagnosis. For low-grade gliomas, the prognosis is somewhat more optimistic, but even such patients have a far higher death rate than does the general population when age is taken into account.

Therefore, there is a substantial need for an improved treatment for gliomas. In addition, there is a particular need to provide treatments that can avoid or counteract the potentially mutagenic effect of the frequently-used antineoplastic drugs, such as temozolomide. As detailed below, the principles of treatment provided in the present invention can also be applied to malignancies in general, as cancer is typically characterized by mutation of the neoplastic cells.

U.S. Pat. No. 6,277,411 to Shaked et al. discloses a pharmaceutical formulation containing eflornithine for the treatment of cancer. U.S. Pat. No. 5,851,537 to Alberts et al. discloses a formulation for topical application of eflornithine for the prevention of skin cancer. European Patent Application Publication No. EP 0886519 by Shaked et al. discloses a sustained release formulation containing eflornithine.

As detailed below, one promising treatment for glioma and other malignancies is the administration of eflornithine or a derivative, analog, or prodrug thereof. Therefore, in particular, there is a need for improved formulations of eflornithine or a derivative, analog, or prodrug thereof that can deliver suitable dosages, particularly in an individualized dosing regimen or in a dosing regimen that employs additional therapeutic agents. There is also, in particular, a need for improved formulations of eflornithine that can overcome the blood-brain barrier by creating a plasma concentration that enables a sufficient gradient to overcome it. Additionally, there is a need for dosing devices for accurate delivery of eflornithine for brain tumor treatment.

There is, additionally, a need to provide compositions and delivery methods to meet the challenge of delivering large doses of eflornithine or derivatives, analogs, or prodrugs thereof that are individualized according to the patients' body surface area (BSA) or other parameters used in determining optimum doses for anti-neoplastic therapeutic agents.

SUMMARY OF THE INVENTION

The present invention provides formulations for the administration of eflornithine or a derivative, analog, or prodrug thereof, particularly for treatment of malignancies such as glioma. In particular, the active component or components in these formulations, particularly the eflornithine or the derivative, analog, or prodrug thereof, can penetrate though the blood-brain barrier when administered to a subject suffering from glioma.

One embodiment of the present invention is a pharmaceutical composition comprising:

(1) a therapeutically effective quantity of eflornithine or a derivative, analog, or prodrug thereof; and (2) at least one pharmaceutically acceptable excipient, wherein the pharmaceutically acceptable excipient is selected from the group consisting of:

(a) a preservative;
(b) a sweetening agent;
(c) a thickening agent;
(d) a buffer;
(e) a liquid carrier;
(f) an isotonic agent;
(g) a wetting, solubilizing, or emulsifying agent;
(h) an acidifying agent;
(i) an antioxidant;
(j) an alkalinizing agent;
(k) a carrying agent;
(l) a chelating agent;
(m) a colorant;
(n) a complexing agent;
(o) a solvent;
(p) a suspending and or viscosity-increasing agent;
(q) a flavor or perfume;
(r) an oil;
(s) a penetration enhancer;
(t) a polymer;
(u) a stiffening agent;
(v) a protein;
(w) a carbohydrate;
(x) a bulking agent; and
(y) a lubricating agent.

In one alternative, the eflornithine or derivative, analog, or prodrug thereof is selected from the group consisting of eflornithine and a pharmaceutically acceptable salt form, hydrate, or solvate thereof. In another alternative, the eflornithine or derivative, analog, or prodrug thereof is a derivative, analog, or prodrug of eflornithine.

The pharmaceutical composition can be formulated for treatment of a glioma. In one alternative, when the composition is administered to a subject suffering from a glioma, the eflornithine or derivative, analog, or prodrug thereof can penetrate through the blood-brain barrier. In another alternative, the composition is formulated such that the eflornithine or derivative, analog, or prodrug thereof is delivered in fully dissolved form in doses of above 1.4 g/m$^2$ or higher doses, up to 2.8 g/m$^2$ or higher that can be individually adjusted according to patient BSA. A dose of 2.8 g/m$^2$ is typically optimum.

The pharmaceutical composition can be formulated for oral administration or administration by injection.

The pharmaceutical composition can comprise a therapeutically effective quantity of at least one additional therapeutic agent that is compatible with the eflornithine or the derivative, analog, or prodrug thereof. In other alternatives, the pharmaceutical composition can further comprise: an inhibitor of polyamine transport or polyamine synthesis; an S-adenosylmethionine decarboxylase inhibitor; an agent selected from the group consisting of: a retinoid; a syrbactin compound; a cyclooxygenase-2 inhibitor; a non-steroidal anti-inflammatory agent; castanospermine or castanospermine esters; an aziridinyl putrescine compound; an interferon or interferon inducer; an aryl substituted xylopyranoside derivative; an agent that reduces blood glutamate levels and enhances brain to blood glutamate efflux; chitosan or chitosan derivatives and analogs; 2,4-disulfonyl phenyl tert-butyl nitrone; 3-(4-amino-1-oxo-1,3-dihydro-isoindol-2-yl)-piperidine-2,6-dione; thalidomide; N-2-pyridinyl-2-pyridinecarbothioamide; cambendazole; or an inhibitor of histone demethylase. In yet another alternative, the composition further comprises a quantity of an agent that increases the ability of the eflornithine or derivative, analog, or prodrug thereof to pass through the blood-brain barrier, wherein the quantity of the agent that increases the ability of the eflornithine or derivative, analog, or prodrug thereof to pass through the blood-brain barrier is sufficient to provide a therapeutically effective dose of the eflornithine or derivative, analog, or prodrug thereof to a tissue of the central nervous system. In still another alternative, the composition further comprises a therapeutically effective quantity of an immunomodulatory agent selected from the group consisting of: (a) IL-15; (b) anti-PD1 antibodies; (c) anti-B7-H1 antibodies; (d) IL-12; (e) QS-21; (f) CD-40; (g) anti-CD40 antibody acting as a CD40 agonist; (h) CD40L; (i) IL-7; (j) CpG; (k) 1-methyltryptophan; (l) anti-CD137 antibodies; (m) anti-TGF-β antibodies; (n) anti-IL10 antibodies; (o) anti-ILR10R antibodies; (p) Flt3L; (q) Anti-GITR; (r) CCL21 or a nucleic acid encoding CCL21; (s) monophosphoryl lipid A; (t) poly I:C; (u) poly ICLC; (v) anti-OX40 antibodies; (w) anti-B7-H4 antibodies; (x) an immune response modulator selected from the group consisting of: resiquimod; N-[4-(4-amino-2-ethylimidazo[4,5-c]quinolin-1-yl)butyl]methanesulfonamide); imiquimod; 2-ethoxymethyl)-1H-imidazo[4,5-c]quinolin-4-amine; 2-propylthiazolo[4,5-c]quinolin-4-amine; isatoribine; ANA975, ANA-773; and GS-9620; (y) LIGHT or a nucleic acid encoding LIGHT; (z) antibodies to LAG-3; and (aa) antibodies to CTLA4. In still another alternative, the composition further comprises a therapeutically effective quantity of an EGFR inhibitor.

Typically, the composition is in a physical form selected from the group consisting of solutions, suspensions, gels, rapidly dissolving powders, rapidly dissolving tablets, capsules, tablets, multiple capsules, multiple tablets, chewables, and bars. The composition can be in another physical form as known in the art. Various combinations of excipients can be used in compositions of these physical forms.

Another aspect of the present invention is a kit comprising two or more dosage forms of a pharmaceutical composition according to the present invention that is in a solid dosage form wherein the solid dosage form is selected from the group consisting of powders, capsules and tablets. The two or more dosage forms are packaged such that each dosage form can be accessed separately by a user of the kit. The two or more dosage forms can be identical or different. The solid dosage forms can optionally include an additional component. In another alternative, the kit can comprise at least one dosage form comprising eflornithine or a derivative, analog, or prodrug thereof and at least one additional component. The dosage forms can be incorporated in a blister pack. In another alternative of a kit, the kit can comprise at least one pharmaceutical composition according to the present invention and a dispensing or dosing device.

BRIEF DESCRIPTION OF THE DRAWINGS

These and other features, aspects, and advantages of the present invention will become better understood with reference to the following description, appended claims, and accompanying drawings where:

FIG. 3 is a graph showing the results of freezing trend analysis in seeded eflornithine formulations.

DETAILED DESCRIPTION OF THE INVENTION

Figure 1:
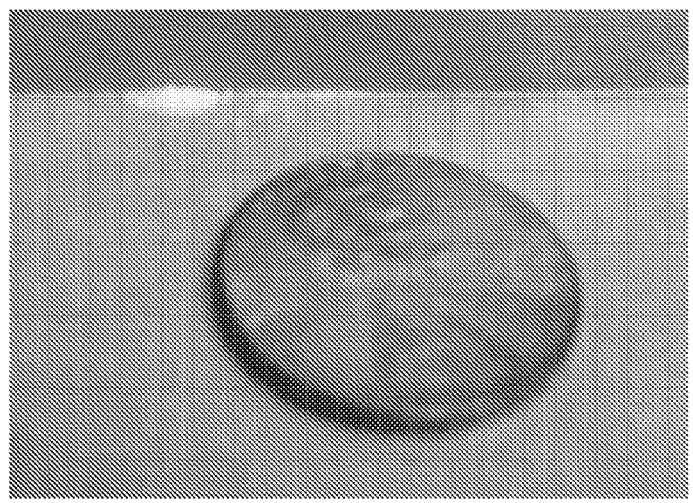
FIG. 1 is an illustration of the quantity of eflornithine used to seed the formulations in Example 4 (0.003 g).

One aspect of the present invention is a pharmaceutical composition comprising:

(1) a therapeutically effective quantity of eflornithine or a derivative, analog, or prodrug thereof; and (2) at least one pharmaceutically acceptable excipient, wherein the pharmaceutically acceptable excipient is selected from the group consisting of:
(a) a preservative;
(b) a sweetening agent;
(c) a thickening agent;
(d) a buffer;
(e) a liquid carrier;
(f) an isotonic agent;
(g) a wetting, solubilizing, or emulsifying agent;
(h) an acidifying agent;
(i) an antioxidant;
(j) an alkalinizing agent;
(k) a carrying agent;
(l) a chelating agent;
(m) a colorant;
(n) a complexing agent;
(o) a solvent;
(p) a suspending and or viscosity-increasing agent;
(q) a flavor or perfume;
(r) an oil;
(s) a penetration enhancer;
(t) a polymer;
(u) a stiffening agent;
(v) a protein;
(w) a carbohydrate;
(x) a bulking agent; and
(y) a lubricating agent.

Eflornithine occurs in two enantiomeric forms: D-eflornithine and L-eflornithine. D-eflornithine is shown in Formula (Ia), below. L-eflornithine is shown in Formula (Ib), below.

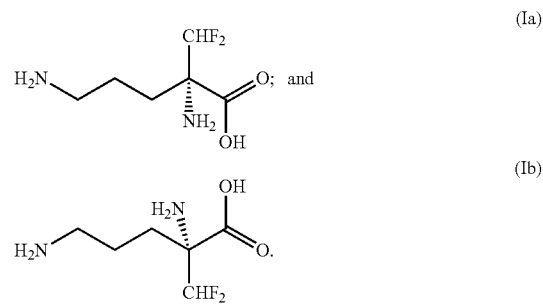

Typically, eflornithine is administered as the racemic mixture of D-eflornithine and L-eflornithine. However, eflornithine can also be administered in a mixture in which the D-eflornithine is relatively enriched with respect to the L-eflornithine, or in a pure or substantially pure preparation of D-eflornithine. In another alternative, eflornithine can be administered in a mixture in which the L-eflornithine is relatively enriched with respect to the D-eflornithine, or in a pure or substantially pure preparation of L-eflornithine.

Eflornithine is a structural analog of the amino acid L-ornithine (shown below as Formula (II)

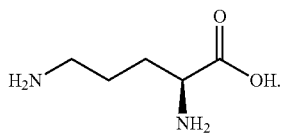
(II)

A number of derivatives and analogs of eflornithine are known in the art, and are described further below.

U.S. Pat. No. 5,614,557 to Bey et al. discloses analogs of eflornithine of Formula (III):

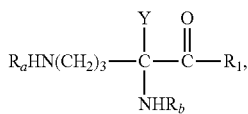
(III)

wherein:
(1) Y is $FCH_2$—, $F_2CH$—, or $F_3C$—;
(2) $R_a$ and $R_b$ are, independently, hydrogen, ($C_1$-$C_4$) alkylcarbonyl, or a group of Formula (III(a))

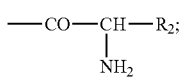
(III(a))

wherein, in Formula (III(a)), $R_2$ is hydrogen, ($C_1$-$C_4$) alkyl, benzyl, or p-hydroxybenzyl;
(3) $R_1$ is hydroxyl, ($C_1$-$C_8$) alkoxy, —$NR_4R_5$, wherein $R_4$ and $R_5$ are independently hydrogen, ($C_1$-$C_4$) alkyl, or a group of Formula (III(b))

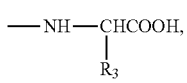
(III(b))

wherein, in Formula (III(b)), $R_3$ is hydrogen, $C_1$-$C_4$) alkyl, or p-hydroxybenzyl.

U.S. Pat. No. 5,002,879 to Bowlin et al. discloses additional ornithine decarboxylase inhibitors of Formulas (IV) and (V):

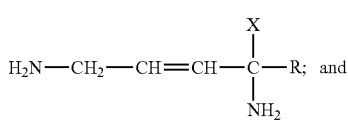
(IV)

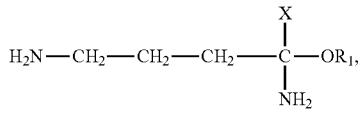
(V)

wherein:
(1) X is —$CHF_2$ or —$CH_2F$;
(2) R is hydrogen or —$COR_1$; and
(3) $R_1$ is —OH or ($C_1$-$C_6$) alkoxy.

Water-soluble salts of eflornithine with polycations such as polycationic carbohydrates (chitosan, water-soluble chitosan derivative, or a salt thereof) or a polyaminoacid, a polyamine, a polypeptide, a basic polymer, or a quaternary ammonium compound are disclosed in United States Patent Application Publication No. 2002/0019338 by Hebert. All pharmaceutically acceptable salt forms, hydrates, and solvates of eflornithine and derivatives, analogs, and prodrugs of eflornithine can be used in methods and compositions of the present invention.

Additional derivatives, analogs, and prodrugs of eflornithine are known in the art. United States Patent Application Publication No. 2010/0120727 by Xu discloses conjugates in which a first moiety that is eflornithine or a derivative, analog, or prodrug of eflornithine is covalently linked to a second moiety that is a non-steroidal anti-inflammatory drug (NSAID). The NSAID can be, for example, aspirin, aceclofenac, acemethacin, alclofenac, amoxiprin, ampyrone, azapropazone, benorylate, bromfenac, choline and magnesium salicylates, choline salicylate, celecoxib, clofezone, diclofenac potassium, diclofenac sodium, diclofenac sodium with misoprostol, diflunisal, droxicam, lornoxicam, meloxicam, tenoxicam, ethenzamide, etodolac, fenoprofen calcium, faislamine, flurbiprofen, flufenamic acid, ibuprofen, ibuproxam, indoprofen, alminoprofen, carprofen, dexibuprofen, dexketoprofen, fenbufen, flunoxaprofen, indomethacin, ketoprofen, ketorolac, kebuzone, loxoprofen, magnesium salicylate, meclofenamate sodium, metamizole, mofebutazone, oxyphenbutazone, phenazone, sulfinpyrazone, mefenamic acid, meloxicam, methyl salicylate, nabumetone, naproxen, naproxen sodium, nebumetone, oxaprozin, oxametacin, phenylbutazone, proglumetacin, piroxicam, pirprofen, suprofen, rofecoxib, salsalate, salicyl salicylate, salicylamide, sodium salicylate, sulindac, tiaprofenic acid, tolfenamic acid, tolmetin sodium, and valdecoxib. The first and second moieties can be linked via a covalent bond selected from the group consisting of an ester bond, an amide bond, an imine bond, a carbamate bond, a carbonate bond, a thioester bond, an acyloxycarbamate bond, an acyloxycarbonate bond, an acyloxythiocarbamate, a phosphate bond, a phosphoramidate and an acyloxyphosphate bond.

United States Patent Application Publication No. 2015/0306241 by Zhu et al. discloses copolymers of formula A-B-C or a pharmaceutically acceptable salt thereof, wherein A comprises a water soluble polymer; B comprises a matrix metalloprotease (MMP)-cleavable polypeptide; C is a chemotherapeutic drug or a derivative thereof; and A is connected to B at a first end through a first covalent bond or a first linking moiety and B is connected to C at a second end through a second covalent bond or a second linking moiety, and wherein the co-polymer is not crosslinked. Typically, in this copolymer, the chemotherapeutic drug is an amino-containing therapeutic drug, such as eflornithine.

United States Patent Application Publication No. 2002/0110590 by Shaked et al. discloses formulations for the administration of eflornithine, including a core having a rapid release DFMO-containing granules and slow release granules and an outer layer surrounding the core comprising a pH responsive coating.

U.S. Pat. No. 7,718,764 to Wong et al. discloses conjugates of eflornithine with peptides, including VAP-EEHPTLLTEAPLNPK (SEQ ID NO: 1) and fragments and derivatives thereof, for use as an anti-neoplastic agent.

Prodrugs of eflornithine are also known in the art. Such prodrugs of eflornithine are disclosed in United States Patent Application Publication No. 2010/0120727 by Xu. Such prodrugs include compounds of Formulas (EP-I) and (EP-II):

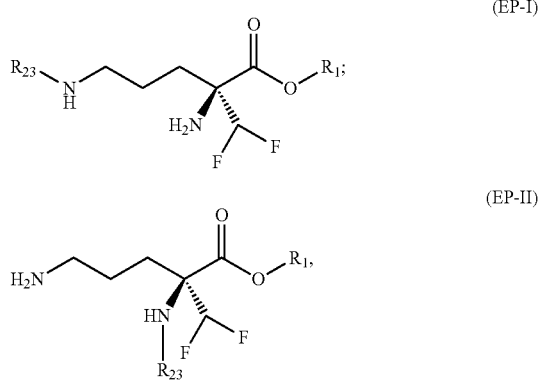

wherein:

(1) $R_{23}$ is selected from the group consisting of hydrogen, $R_{24}C(O)-$, $R_{24}OC(O)-$, $R_{24}C(S)-$, $R_{24}SC(O)-$, $(R_{24}O)(R_{24}O)P(O)-$, and a moiety of Subformula (EP-I(a)), (EP-I(b)), (EP-I(c)), or (EP-I(d))

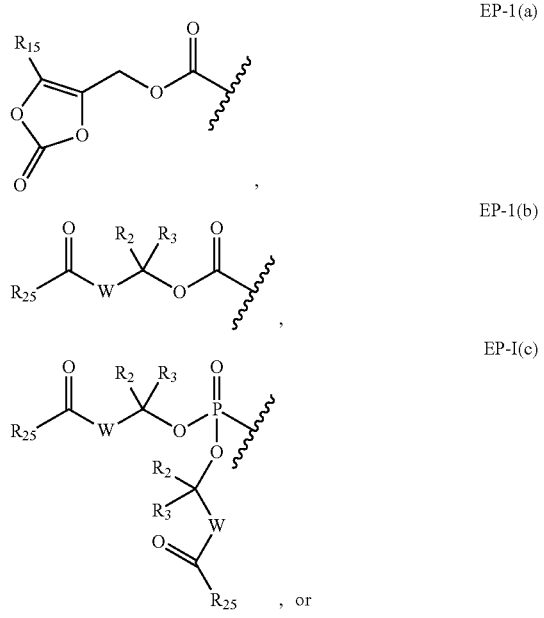

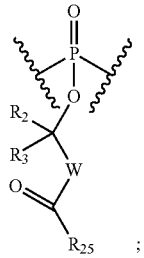

(2) $R_1$ is independently selected from the group consisting of hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl and substituted heteroarylalkyl;

(3) $R_2$ and $R_3$ are each independently selected from the group consisting of hydrogen, alkyl, substituted alkyl, acyl, substituted alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl, substituted heteroaryl, arylalkyl, substituted arylalkyl, heteroarylalkyl and substituted heteroarylalkyl;

(4) $R_{15}$ is selected from the group consisting of hydrogen, alkyl, substituted alkyl, acyl, substituted alkoxycarbonyl, substituted alkoxycarbonyl, aryl, substituted aryl, arylalkyl, substituted arylalkyl, carbamoyl, cycloalkyl, substituted cycloalkyl, cycloalkoxycarbonyl, substituted cycloalkoxycarbonyl, heteroaryl, substituted heteroaryl, arylalkyl, substituted arylalkyl, heteroarylalkyl and substituted heteroarylalkyl;

(5) $R_{24}$ and $R_{25}$ are each independently selected from the group consisting of alkyl, substituted alkyl, acyl, substituted acyl, aryl, substituted aryl, arylalkyl, substituted arylalkyl, cycloalkyl, substituted cycloalkyl, cycloalkoxycarbonyl, substituted cycloalkoxycarbonyl, heteroaryl, substituted heteroaryl, arylalkyl, substituted arylalkyl, heteroarylalkyl and substituted heteroarylalkyl; and (6) W is —O— or —NH—.

In one alternative of an eflornithine prodrug, a phosphoramidate group is cleaved upon in vivo administration of the eflornithine prodrug, releasing the active form of eflornithine in vivo. The phosphoramidate group released from the eflornithine prodrug is typically non-toxic when the eflornithine prodrug is administered to a mammal at a therapeutically effective dosage.

As used herein, the term "prodrug" refers to compounds that are transformed in vivo to yield a disclosed compound or a pharmaceutically acceptable form of the compound. In some embodiments, a prodrug is a compound that may be converted under physiological conditions or by solvolysis to a biologically active compound as described herein. Thus, the term "prodrug" refers to a precursor of a biologically active compound that is pharmaceutically acceptable. A prodrug can be inactive when administered to a subject, but is then converted in vivo to an active compound, for example, by hydrolysis (e.g., hydrolysis in blood or a tissue). In certain cases, a prodrug has improved physical and/or delivery properties over a parent compound from which the prodrug has been derived. The prodrug often offers advantages of solubility, tissue compatibility, or delayed release in a mammalian organism (H. Bundgard, *Design of Prodrugs* (Elsevier, Amsterdam, 1988), pp. 7-9, 21-24), incorporated herein by this reference. A discussion of prodrugs is provided in T. Higuchi et al., "Pro-Drugs as Novel Delivery Systems," *ACS Symposium Series*, Vol. 14 and in E. B. Roche, ed., *Bioreversible Carriers in Drug Design* (American Pharmaceutical Association & Pergamon Press, 1987), both incorporated herein by this reference. Exemplary advantages of a prodrug can include, but are not limited to, its physical properties, such as enhanced water solubility for parenteral administration at physiological pH compared to the parent compound, enhanced absorption from the digestive tract, or enhanced drug stability for long-term storage.

The term "prodrug" is also meant to include any covalently bonded carriers which release the active compound in vivo when the prodrug is administered to a subject. Prodrugs of a therapeutically active compound, as described herein, can be prepared by modifying one or more functional groups present in the therapeutically active compound in such a way that the modifications are cleaved, either in routine manipulation or in vivo, to yield the parent therapeutically active compound. Prodrugs include compounds wherein a hydroxy, amino, or mercapto group is covalently bonded to any group that, when the prodrug of the active compound is administered to a subject, cleaves to form a free hydroxy, free amino, or free mercapto group, respectively. Examples of prodrugs include, but are not limited to, formate or benzoate derivatives of an alcohol or acetamide, formamide or benzamide derivatives of a therapeutically active agent possessing an amine functional group available for reaction, and the like.

For example, if a therapeutically active agent or a pharmaceutically acceptable form of a therapeutically active agent contains a carboxylic acid functional group, a prodrug can comprise an ester formed by the replacement of the hydrogen atom of the carboxylic acid group with a group such as $C_{1-8}$ alkyl, $C_{2-12}$ alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, γ-butyrolacton-4-yl, di-N,N($C_1$-$C_2$)alkylamino($C_2$-$C_3$)alkyl (such as (3-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino-, or morpholino($C_2$-$C_3$)alkyl.

Similarly, if a disclosed compound or a pharmaceutically acceptable form of the compound contains an alcohol functional group, a prodrug can be formed by the replacement of the hydrogen atom of the alcohol group with a group such as ($C_1$-$C_6$)alkanoyloxymethyl, 1-(($C_1$-$C_6$))alkanoyloxy) ethyl, 1-methyl-1-(($C_1$-$C_6$)alkanoyloxy)ethyl ($C_1$-$C_6$) alkoxycarbonyloxymethyl, N($C_1$-$C_6$)alkoxycarbonylaminomethyl, succinoyl, ($C_1$-$C_6$)alkanoyl, α-amino($C_1$-$C_4$) alkanoyl, arylacyl and α-aminoacyl, or α-aminoacyl-α-aminoacyl, where each α-aminoacyl group is independently selected from the naturally occurring L-amino acids, P(O)(OH)$_2$, P(O)(O($C_1$-$C_6$)alkyl)$_2$ or glycosyl (the radical resulting from the removal of a hydroxyl group of the hemiacetal form of a carbohydrate).

If a disclosed compound or a pharmaceutically acceptable form of the compound incorporates an amine functional group, a prodrug can be formed by the replacement of a hydrogen atom in the amine group with a group such as R-carbonyl, RO-carbonyl, NRR'-carbonyl where R and R' are each independently ($C_1$-$C_{10}$)alkyl, ($C_3$-$C_7$)cycloalkyl, benzyl, or R-carbonyl is a natural α-aminoacyl or natural α-aminoacyl-natural α-aminoacyl, C(OH)C(O)OY$^1$ wherein Y$^1$ is H, ($C_1$-$C_6$)alkyl or benzyl, C(OY$^2$)Y$^3$ wherein Y$^2$ is ($C_1$-$C_4$) alkyl and Y$^3$ is ($C_1$-$C_6$)alkyl, carboxy($C_1$-$C_6$) alkyl, amino($C_1$-$C_4$)alkyl or mono-N or di-N,N($C_1$-$C_6$)alkylaminoalkyl, C(Y$^4$)Y$^5$ wherein Y$^4$ is H or methyl and Y$^5$ is mono-N or di-N,N($C_1$-$C_6$)alkylamino, morpholino, piperidin-1-yl or pyrrolidin-1-yl.

The use of prodrug systems is described in T. Jarvinen et al., "Design and Pharmaceutical Applications of Prodrugs" in *Drug Discovery Handbook* (S. C. Gad, ed., Wiley-Interscience, Hoboken, N.J., 2005), ch. 17, pp. 733-796, incorporated herein by this reference.

Other prodrugs of eflornithine or of derivatives or analogs of eflornithine are known in the art and are within the scope of the invention.

Accordingly, one aspect of the present invention is a pharmaceutical composition formulated for the treatment of glioma comprising:

(1) a therapeutically effective quantity of eflornithine or a derivative, analog, or prodrug thereof; and (2) at least one pharmaceutically acceptable excipient; wherein the pharmaceutical composition is formulated for treatment of glioma or another malignancy. As used herein, the term "therapeutically effective quantity," as applied to eflornithine, a derivative, analog, or prodrug of eflornithine, or another therapeutic agent incorporated into a pharmaceutical composition according to the present invention, is a quantity that produces a clinically detectable response. The clinically detectable response is an improvement in one or more of the clinical parameters associated with the glioma or other malignancy, including, but not limited to, reduction in tumor burden, reduction in pain, improvement in central nervous system function, reduction of symptomatology such as seizures or headaches, improvement in Karnofsky Performance Score, and reduction in occurrence of tumor spread or metastasis; the clinical parameter and the improvement associated therewith can be objective or subjective. The term "pharmaceutically acceptable," as applied to an excipient, is defined as compatible with the eflornithine or derivative, analog, or prodrug of eflornithine, compatible with any other therapeutically active agent incorporated into the composition, and being tolerated by the subject to whom the pharmaceutical composition is administered.

Typically, the eflornithine or derivative, analog or prodrug thereof is eflornithine. As described above, the eflornithine can be a racemic mixture of D-eflornithine and L-eflornithine, D-eflornithine, or L-eflornithine.

In another alternative, the eflornithine or derivative, analog, or prodrug of eflornithine is a derivative, analog, or prodrug of eflornithine as described above, including: (A) an analog of eflornithine of Formula (III):

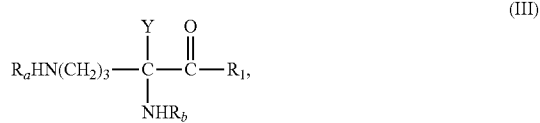

(III)

wherein:

(1) Y is FCH$_2$—, F$_2$CH—, or F$_3$C—;

(2) R$_a$ and R$_b$ are, independently, hydrogen, ($C_1$-$C_4$) alkylcarbonyl, or a group of Formula (III(a))

III(a)

wherein, in Formula (III(a)), R$_2$ is hydrogen, ($C_1$-$C_4$) alkyl, benzyl, or p-hydroxybenzyl;

(3) $R_1$ is hydroxy, $(C_1-C_8)$ alkoxy, $-NR_4R_5$, wherein $R_4$ and $R_5$ are independently hydrogen, $(C_1-C_4)$ alkyl, or a group of Formula (III(b))

wherein, in Formula (III(b)), $R_3$ is hydrogen, $C_1-C_4$ alkyl, or p-hydroxybenzyl; (B) an analog of eflornithine of Formula (IV) or Formula (V):

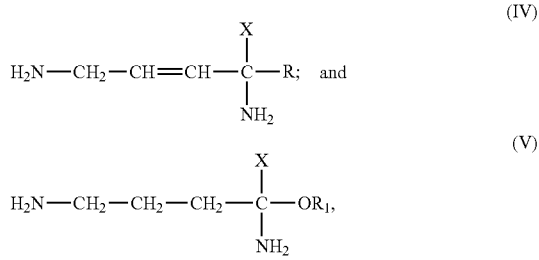

wherein:
(1) X is $-CHF_2$ or $-CH_2F$;
(2) R is hydrogen or $-COR_1$; and
(3) $R_1$ is $-OH$ or $(C_1-C_6)$ alkoxy; (C) a water-soluble salt of eflornithine with a polycation selected from: (i) a polycationic carbohydrate selected from the group consisting of chitosan, water-soluble chitosan derivative, and a salt thereof; (ii) a polyaminoacid; (iii) a polyamine; (iv) a polypeptide; (v) a basic polymer; and (vi) a quaternary ammonium compound; (D) a conjugate comprising a first moiety comprising eflornithine or a derivative, analog, or prodrug of eflornithine covalently linked to a second moiety that is a non-steroidal anti-inflammatory drug selected from the group consisting of aspirin, aceclofenac, acemethacin, alclofenac, amoxiprin, ampyrone, azapropazone, benorylate, bromfenac, choline and magnesium salicylates, choline salicylate, celecoxib, clofezone, diclofenac potassium, diclofenac sodium, diclofenac sodium with misoprostol, diflunisal, droxicam, lornoxicam, meloxicam, tenoxicam, ethenzamide, etodolac, fenoprofen calcium, faislamine, flurbiprofen, flufenamic acid, ibuprofen, ibuproxam, indoprofen, alminoprofen, carprofen, dexibuprofen, dexketoprofen, fenbufen, flunoxaprofen, indomethacin, ketoprofen, ketorolac, kebuzone, loxoprofen, magnesium salicylate, meclofenamate sodium, metamizole, mofebutazone, oxyphenbutazone, phenazone, sulfinpyrazone, mefenamic acid, meloxicam, methyl salicylate, nabumetone, naproxen, naproxen sodium, nebumetone, oxaprozin, oxametacin, phenylbutazone, proglumetacin, piroxicam, pirprofen, suprofen, rofecoxib, salsalate, salicyl salicylate, salicylamide, sodium salicylate, sulindac, tiaprofenic acid, tolfenamic acid, tolmetin sodium, and valdecoxib, wherein the first and second moieties are linked via a covalent bond selected from the group consisting of an ester bond, an amide bond, an imine bond, a carbamate bond, a carbonate bond, a thioester bond, an acyloxycarbamate bond, an acyloxycarbonate bond, an acyloxythiocarbamate, a phosphate bond, a phosphoramidate and an acyloxyphosphate bond; (E) a copolymer of formula A-B-C or a pharmaceutically acceptable salt thereof, wherein: A comprises a water-soluble polymer; B comprises a matrix metalloprotease (MMP)-cleavable polypeptide; C is eflornithine or a derivative, analog, or prodrug of eflornithine; and A is connected to B at a first end through a first covalent bond or a first linking moiety and B is connected to C at a second end through a second covalent bond or a second linking moiety, and wherein the co-polymer is not crosslinked; (F) a conjugate of eflornithine or a derivative, analog, or prodrug of eflornithine conjugated to a peptide selected from the group consisting of: (i) a peptide of sequence VAPEEHPTLLTEAPLNPK (SEQ ID NO: 1); (ii) a fragment of a peptide of SEQ ID NO: 1; and (iii) a derivative of a peptide of SEQ ID NO: 1; and (G) a derivative of eflornithine that is an inhibitor of ornithine decarboxylase and that is selected from a monosubstituted derivative, a disubstituted derivative, a trisubstituted derivative, an ethyl ester derivative, and a 6-amide derivative.

In one alternative, a composition according to the present invention is formulated for oral administration.

In another alternative, a composition according to the present invention is formulated for administration by injection. Typically, when the composition is formulated for administration by injection, the route of injection is selected from the group consisting of intraperitoneal administration, intravenous administration, and subcutaneous administration.

In one alternative, the eflornithine or derivative, analog, or prodrug thereof is delivered in fully dissolved form in doses of above 1.4 $g/m^2$ or higher doses, up to 2.8 $g/m^2$ or higher that can be individually adjusted according to patient BSA. A dose of 2.8 $g/m^2$ is typically optimum.

Typically, the at least one pharmaceutically acceptable excipient is selected from the group consisting of: a liquid carrier; an isotonic agent; a wetting, solubilizing, or emulsifying agent; a preservative; a buffer; an acidifying agent; an antioxidant; an alkalinizing agent; a carrying agent; a chelating agent; a colorant; a complexing agent; a solvent; a suspending and/or viscosity-increasing agent; a flavor or perfume; an oil; a penetration enhancer; a polymer; a stiffening agent; a thickening agent; a sweetening agent; a protein; a carbohydrate; a bulking agent; and a lubricating agent. Pharmaceutically acceptable excipients may be added to facilitate manufacture, enhance stability, control release, enhance product characteristics, enhance bioavailability, drug absorption or solubility, optimize other pharmacokinetic considerations, optimize the pharmaceutical formulation for a route of administration, enhance patient acceptability, or for another reason related to manufacture, storage, or use of a pharmaceutical composition. Excipients used in pharmaceutical compositions according to the present invention are compatible with the pharmaceutically active agent or agents included in the pharmaceutical composition, are compatible with other excipients included in the pharmaceutical composition, and are not injurious to and are tolerated by any patients to whom the pharmaceutical composition is administered.

As is generally known in the art of pharmaceutical formulation, a particular excipient can fulfill one or more of these functions in a particular pharmaceutical composition, depending on the concentration of the excipient, the other excipients in the composition, the physical form of the composition, the concentration of active agent in the composition, the intended route of administration of the composition, and other factors. The recitation of a particular excipient in a category below is not intended to exclude the possible use of the excipient in another category or categories.

Typically, the liquid carrier can be, but is not limited to, a liquid carrier selected from the group consisting of saline, phosphate buffered saline, glycerol, and ethanol.

Typically, the isotonic agent can be, but is not limited to, a polyalcohol selected from the group consisting of mannitol and sorbitol, sodium chloride, and potassium chloride.

Typically, the wetting or emulsifying agent is a surfactant. Typically, the surfactant is selected from the group consisting of benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaureate, sorbitan monooleate, sorbitan monopalmitate, sorbitan monostearate, tyloxapol, acacia, cholesterol, diethanolamine, glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, soritan monooleate, sorbitan monopalmitate, sorbitan monostearate, stearic acid, triethanolamine, emulsifying wax, cetomacrogol, and cetyl alcohol.

Typically, the preservative is selected from the group consisting of benzalkonium chloride, benzalkonium chloride solution, benzethonium chloride, benzoic acid, benzyl alcohol, butylparaben, cetylpyridinium chloride, chlorobutanol, chlorocresol, cresol, dehydroacetic acid, diazolidinyl urea, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, and thymol.

Typically, the buffer is selected from the group consisting of acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate, sodium bicarbonate, Tris (Tris(hydroxymethyl)aminomethane), MOPS (3-(N-morpholino)propanesulfonic acid), HEPES (N-(2-hydroxyethyl)piperazine-N'-(2-ethanesulfonic acid), ACES (2-[(2-amino-2-oxoethyl)amino]ethanesulfonic acid), ADA (N-(2-acetamido)2-iminodiacetic acid), AMPSO (3-[(1,1-dimethyl-2-hydroxyethylamino]-2-propanesulfonic acid), BES (N,N-bis(2-hydroxyethyl)-2-aminoethanesulfonic acid, Bicine (N,N-bis(2-hydroxyethylglycine), Bis-Tris (bis-(2-hydroxyethyl)imino-tris(hydroxymethyl)methane, CAPS (3-(cyclohexylamino)-1-propanesulfonic acid), CAPSO (3-(cyclohexylamino)-2-hydroxy-1-propanesulfonic acid), CHES (2-(N-cyclohexylamino)ethanesulfonic acid), DIPSO (3-[N,N-bis(2-hydroxyethylamino]-2-hydroxy-propane-sulfonic acid), HEPPS (N-(2-hydroxyethylpiperazine)-N'-(3-propanesulfonic acid), HEPPSO (N-(2-hydroxyethyl)piperazine-N'-(2-hydroxypropanesulfonic acid), MES (2-(N-morpholino)ethanesulfonic acid), triethanolamine, imidazole, glycine, ethanolamine, phosphate, MOPSO (3-(N-morpholino)-2-hydroxypropanesulfonic acid), PIPES (piperazine-N,N'-bis(2-ethanesulfonic acid), POPSO (piperazine-N,N'-bis(2-hydroxypropaneulfonic acid), TAPS (N-tris[hydroxymethyl)methyl-3-aminopropanesulfonic acid), TAPSO (3-[N-tris(hydroxymethyl)methylamino]-2-hydroxy-propanesulfonic acid), TES (N-tris(hydroxymethyl)methyl-2-aminoethanesulfonic acid), tricine (N-tris(hydroxymethyl)methylglycine), 2-amino-2-methyl-1,3-propanediol, and 2-amino-2-methyl-1-propanol.

Typically, the acidifying agent is selected from the group consisting of acetic acid, citric acid, fumaric acid, hydrochloric acid, diluted hydrochloric acid, malic acid, nitric acid, phosphoric acid, diluted phosphoric acid, sulfuric acid, and tartaric acid.

Typically, the antioxidant is selected from the group consisting of ascorbic acid, ascorbyl palmitate, butylated hydroxyanisole, butylated hydroxytoluene, hypophosphorous acid, monothioglycerol, propyl gallate, sodium ascorbate, sodium bisulfite, sodium formaldehyde sulfoxylate, sodium metabisulfite, sodium thiosulfate, sulfur dioxide, and tocopherol.

Typically, the alkalinizing agent is selected from the group consisting of strong ammonia solution, ammonium carbonate, diethanolamine, diisopropanolamine, potassium hydroxide, sodium bicarbonate, sodium borate, sodium carbonate, sodium hydroxide, and trolamine.

Typically, the carrying agent is selected from the group consisting of acacia syrup, aromatic syrup, aromatic elixir, cherry syrup, cocoa syrup, orange syrup, syrup, corn oil, mineral oil, peanut oil, sesame oil, bacteriostatic sodium chloride for injection and bacteriostatic water for injection.

Typically, the chelating agent is selected from the group consisting of edetate disodium, ethylenediaminetetraacetic acid, citric acid, and salicylates.

Typically, the coloring agent is selected from the group consisting of ferric oxides red, yellow, black or blends, FD&C Red No. 3, FD&C Red No. 20, FD&C Yellow No. 6, FD&C Blue No. 2, D&C Green No. 5, D&C Orange No. 5, D&C Red No. 8, and dyes suitable for pharmaceutical use.

Typically, the complexing agent is selected from the group consisting of ethylenediaminetetraacetic acid, salts of ethylenediaminetetraacetic acid, gentisic acid ethanolamide, and oxyquinoline sulfate.

Typically, the solvent is selected from the group consisting of acetone, ethanol, diluted alcohol, amylene hydrate, benzyl benzoate, butyl alcohol, carbon tetrachloride, chloroform, corn oil, cottonseed oil, ethyl acetate, glycerol, hexylene glycol, isopropyl alcohol, methyl isobutyl ketone, mineral oil, oleic acid, peanut oil, polyethylene glycol, propylene carbonate, propylene glycol, sesame oil, water for injection, sterile water for injection, sterile water for irrigation, and purified water.

Typically, the suspending and/or viscosity-increasing agent is selected from the group consisting of acacia, agar, alginic acid, aluminum monostearate, bentonite, purified bentonite, magma bentonite, carbomers, carbomer 934p, carboxymethylcellulose calcium, carboxymethylcellulose sodium, carboxymethylcellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, Veegum, and xanthan gum.

Typically, the flavor or perfume is selected from the group consisting of anise oil, cinnamon oil, menthol, anethole, benzaldehyde, ethyl vanillin, menthol, methyl salicylate, monosodium glutamate, orange flower oil, peppermint, peppermint oil, peppermint spirit, rose oil, stronger rose water, thymol, tolu balsam tincture, vanilla, vanilla tincture, and vanillin.

Typically, the oil is selected from the group consisting of *arachis* oil, mineral oil, olive oil, sesame oil, cottonseed oil, safflower oil, corn oil, and soybean oil.

Typically, the penetration enhancer is selected from the group consisting of monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones, and ureas.

Typically, the polymer is selected from the group consisting of cellulose acetate, alkyl celluloses, hydroxyalkylcelluloses, acrylic polymers and copolymers, polyesters, polycarbonates, and polyanhydrides.

Typically, the stiffening agent is selected from the group consisting of hydrogenated castor oil, cetostearyl alcohol, cetyl alcohol, cetyl esters wax, hard fat, paraffin, polyethylene excipient, stearyl alcohol, emulsifying wax, white wax, and yellow wax.

Typically, the sweetening agent is selected from the group consisting of aspartame, dextrates, dextrose, excipient dextrose, fructose, glycerol, mannitol, propylene glycol, saccharin, calcium saccharin, sodium saccharin, sorbitol, solution sorbitol, sucrose, compressible sugar, confectioner's sugar, and syrup.

Typically, the protein is selected from the group consisting of bovine serum albumin, human serum albumin (HSA), recombinant human albumin (rHA), gelatin, and casein.

Typically, the carbohydrate is selected from the group consisting of fructose, maltose, galactose, glucose, D-mannose, sorbose, lactose, sucrose, trehalose, cellobiose, raffinose, melezitose, maltodextrins, dextrans, starches, mannitol, maltitol, lactitol, xylitol, sorbitol, and myoinositol.

Typically, the bulking agent is selected from the group consisting of polypeptides and amino acids.

Typically, the lubricating agent is selected from the group consisting of magnesium stearate, stearic acid, sodium lauryl sulfate, and talc.

In one alternative, a pharmaceutical composition according to the present invention is formulated for treatment of a glioma. Typically, the glioma is a WHO Grade I, II, III or Grade IV glioma. The glioma can be selected from the group consisting of anaplastic glioma, anaplastic oligodendroglioma, and mixed anaplastic oligoastrocytoma. In another alternative, the composition is formulated such that the eflornithine or derivative, analog, or prodrug thereof is delivered in fully dissolved form in doses of In another alternative, the composition is formulated such that the eflornithine or derivative, analog, or prodrug thereof is delivered in fully dissolved form in doses of above 1.4 g/m$^2$ or higher doses, up to 2.8 g/m$^2$ or higher, up to 3.6 g/m$^2$, that can be individually adjusted according to patient BSA. A dose of 2.8 g/m$^2$ is typically optimum, but in some alternatives, an optimum dose can be 3.6 g/m$^2$.

Typically, when a pharmaceutical composition according to the present invention is administered to a subject with glioma, the eflornithine or derivative, analog, or prodrug thereof reduces the rate of mutation of the glioma associated with the administration of an alkylating agent.

In one alternative, a pharmaceutical composition according to the present invention is formulated for oral administration. In another alternative, a pharmaceutical composition according to the present invention is formulated for administration by injection.

Excipients for a pharmaceutical composition according to the present invention are selected such that they do not interfere with the activity of the eflornithine or derivative, analog, or prodrug thereof that is included in the pharmaceutical composition. Excipients for a pharmaceutical composition according to the present invention are also selected so that they do not interfere with the activity of other excipients or cause phase separation in the composition. In general, when a hydrophobic excipient such as an oil is included in the composition, a surfactant, wetting agent, or emulsifier is also included in the composition to ensure that phase separation does not occur and to ensure that composition remains stable and homogeneous. The quantities of any excipient included in a composition according to the present invention can be determined by one of ordinary skill in the art in order to ensure suitable physical properties of the composition and also in order to ensure suitable pharmacokinetics for the eflornithine or derivative, analog, or prodrug thereof included in the composition.

Oral dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms such as for example, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an enteric coating; and a film coating. Examples of binders include microcrystalline cellulose, gum tragacanth, glucose solution, acacia mucilage, gelatin solution, molasses, polvinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include croscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Enteric-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

The eflornithine or derivative, analog or prodrug thereof can be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes, colorings and flavors.

The active materials, such as eflornithine or a derivative, analog, or prodrug of eflornithine, can also be mixed with other active materials which do not impair the desired action, or with materials that supplement the desired action. The active ingredient is a compound or acceptable derivative thereof as described herein. Higher concentrations, up to about 98% by weight of the active ingredient may be included.

In all embodiments of pharmaceutical compositions according to the present invention, tablets and capsules formulations may be coated as known by those of skill in the art in order to modify or sustain dissolution of the active ingredient. Thus, for example, they may be coated with a conventional enterically digestible coating, such as phenyl salicylate, waxes and cellulose acetate phthalate.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Vehicles used in elixirs include solvents. Syrups are concentrated aqueous solutions of a sugar, for example, sucrose, and may contain a preservative. An emulsion is a two-phase system in which one liquid is dispersed in the form of small globules throughout another liquid. Vehicles used in emulsions are non-aqueous liquids, emulsifying agents and preservatives. Suspensions use suspending agents and preservatives. Substances used in non-effervescent granules, to be reconstituted into a liquid oral dosage form, include diluents, sweeteners and wetting agents. Substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such as fruits, and synthetic blends of compounds which produce a pleasant taste sensation.

For a solid dosage form, the solution or suspension, in for example, propylene carbonate, vegetable oils or triglycerides, is in some embodiments encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a liquid vehicle, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or poly-alkylene glycol, including, but not limited to, 1,2-dimethoxyethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including an acetal. Alcohols used in these formulations are any water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

In another alternative, a pharmaceutical composition according to the present invention can comprise a therapeutically effective quantity of at least one additional therapeutic agent that is compatible with the eflornithine or the derivative, analog, or prodrug thereof. Typically, the additional therapeutic agent is an anti-neoplastic therapeutic agent. Preferably, the additional therapeutic agent that is an anti-neoplastic agent is an anti-neoplastic agent that is used for the treatment of glioma. Typically, the anti-neoplastic agent that is used for the treatment of glioma is selected from the group consisting of alkylating agents, antimetabolites, anti-angiogenic agents, EGFR inhibitors, platinum-containing agents, topoisomerase inhibitors, and other classes of anti-neoplastic agents. For example, but not by way of limitation, these agents can include lomustine (CCNU), carmustine (BCNU), temozolomide, procarbazine, vincristine, PCV (a combination of lomustine, procarbazine, and vincristine), carboplatin, carboplatin plus thymidine, carmustine plus temozolomide, erlotinib, carboplatin plus erlotinib, cloretazine, lomustine plus cloretazine, imatinib, hydroxyurea, hydroxyurea plus imatinib, irinotecan, thalidomide, temozolomide plus thalidomide, rilotumumab, cilengitide, cis-retinoic acid, celecoxib, cis-retinoic acid plus celecoxib, enzastaurin, sirolimus, erlotinib plus sirolimus, fenretinide, gefitinib, lapatinib, temsirolimus, tipifarnib, vorinostat, diaziquone, methotrexate, melphalan, thioguanine, TPDCV (thioguanine, procarbazine, dibromodulcitol, lomustine, vincristine), a combination of nitrogen mustard, vincristine, and procarbazine, tenoposide, and carboplatin plus tenoposide. Other agents and combinations of agents are known in the art and can be included as additional anti-neoplastic agents or combinations of agents in pharmaceutical compositions according to the present invention. For example, the composition can comprise an inhibitor of EGFR, particularly of EGFR variant III. (A. H. Thorne et al., "Epidermal Growth Factor Targeting and Challenges in Glioblastoma," *Neuro-Oncology* 18: 914-918 (2016)). EGFR inhibitors include, but are not limited to, erlotinib, gefitinib, lapatinib, afatinib, dacomitinib, neratinib, and the monoclonal antibodies cetuximab, nimotuzumab, panitimumab, mAb425, ABT414, AMG595, and MR1-1. EGFR inhibitors that are monoclonal antibodies can be conjugated to additional therapeutically active agents, such as cytotoxins.

In yet another alternative, the pharmaceutical composition can comprise a therapeutically effective quantity of an inhibitor of polyamine transport and/or polyamine synthesis.

In one alternative, the inhibitor of polyamine transport and/or polyamine synthesis is an aromatic hydrocarbon di-substituted with a polyamine as disclosed in U.S. Pat. No. 9,150,495 to Phanstiel, IV.

In yet another alternative, the inhibitor of polyamine transport and/or polyamine synthesis is a compound of structure R-X-L-polyamine wherein R is a straight or branched $C_{10}$-$C_{50}$ saturated or unsaturated aliphatic, carboxyalkyl, carbalkoxyalkyl, or alkoxy; a $C_1$-$C_8$ alicyclic moiety; a single or multiring aryl substituted or unsubstituted aliphatic; and aliphatic-substituted or unsubstituted single or multiring aromatic; a single or multiring heterocyclic; a single or multiring heterocyclic aliphatic; an aryl sulfonyl; X is —CO—, —SO$_2$—, or —CH$_2$—; and L is a covalent bond or a naturally occurring amino acid, lysine, ornithine, or 2,4-diaminobutyric acid.

In still another alternative, the inhibitor of polyamine transport and/or polyamine synthesis is a compound of Formula (PT-I) or (PT-II):

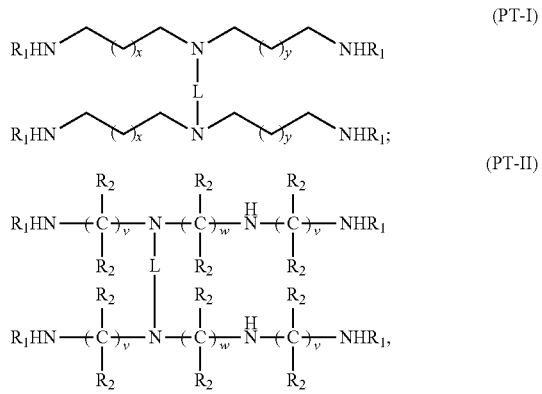

wherein: L is a linker; $R_1$ is hydrogen, methyl, ethyl, or propyl; $R_2$ is hydrogen or methyl; 0<x<3; 0<y<3; 2<v<5; and 2<w<8.

In still another alternative, the inhibitor of polyamine transport and/or polyamine synthesis is an $N^1$-monosubstituted polyamine analog or derivative of Formula (PT-III)

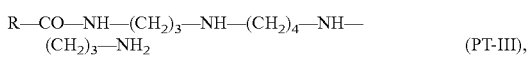

wherein: R is selected from a D or L amino acid; D or L ornithine, an alicyclic, a single or multi-ring aromatic; aliphatic-substituted single or multi-ring aromatic; and a substituted or unsubstituted, single or multi-ring heterocyclic and wherein when R is a substituted single or multi-ring heterocyclic, heterocyclic is substituted with at least one member of the group consisting of: OH, halogen, $NO_2$, $NH_2$, $NH(CH_2)_nCH_3$, $N((CH_2)_nCH_3)_2$, CN, $(CH_2)_nCH_3$, $O(CH_2)_nCH_3$, $S(CH_2)_nCH_3$, $NHCO(CH_2)_nCH_3$, or $O(CF_2)_nCF_3$, $COO(CH_2)_nCH_3$, wherein n is 0-10.

In still another alternative, the inhibitor of polyamine transport and/or polyamine synthesis is a compound of formula $R_1$—X—$R_2$, wherein $R_1$—X— is of the formula R—NH—CR'R"—CO—; wherein NH—CR'R"—CO— is a D- or L-form of valine, asparagine, or glutamine, or the D-form of lysine or arginine; wherein R" is H, $CH_3$, $CH_2CH_3$, or $CHF_2$; where R is H or a head group selected from the group consisting of a straight or branched $C_1$-$C_{10}$ aliphatic, alicyclic, single or multiring aromatic, single or multiring aryl substituted aliphatic, aliphatic-substituted single or multiring aromatic, a single or multiring heterocyclic, a single or multiring heterocyclic-substituted aliphatic and an aliphatic-substituted aromatic; and wherein $R_2$ is a polyamine.

In still another alternative, the inhibitor of polyamine transport and/or polyamine synthesis is a compound of Formula (PT-IV):

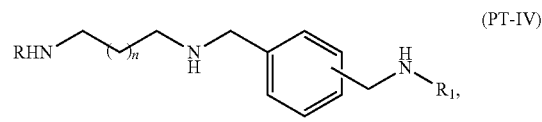

wherein: n can be 0 to 8 and the aminomethyl functionality can be ortho, meta or para substituted, R is hydrogen, 2-aminoethyl, 3-aminopropyl, 4-aminobutyl, 5-aminopentyl, 6-aminohexyl, 7-aminoheptyl, or 8-aminooctyl and $R_1$ is hydrogen and wherein the polyamine is non-symmetrical.

In yet another alternative, the polyamine transport inhibitor and/or polyamine synthesis inhibitor is a compound of Formula (PT-V):

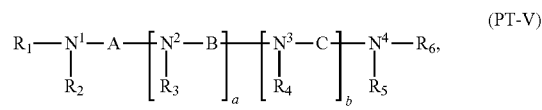

wherein: $R_1$-$R_6$ may be the same or different and are alkyl, aryl, aryl alkyl, or cycloalkyl, optionally having an alkyl chains interrupted by at least one etheric oxygen atom, or hydrogen; $N^1$, $N^2$, $N^3$ and $N^4$ are nitrogen atoms capable of protonation at physiological pH's; a and b may be the same or different and are integers from 1 to 4; A, B and C may be the same or different and are bridging groups which effectively maintain the distance between the nitrogen atoms such that the polyamine: (i) is capable of uptake by a target cell upon administration of the polyamine to a human or non-human animal; and (ii) upon uptake by the target cell, competitively binds via an electrostatic interaction between the positively charged nitrogen atoms to substantially the same biological counter-anions as the intra-cellular natural polyamines in the target cell; the polyamine, upon binding to the biological counter-anion in the cell, functions in a manner biologically different than the intracellular polyamines, the polyamine not occurring in nature.

In still another alternative, the polyamine transport inhibitor and/or polyamine synthesis inhibitor is the polyamine analog N(1),N(11)-diethylnorspermine (DENSPM), which is a polyamine synthesis inhibitor.

In yet another alternative, the polyamine transport inhibitor and/or polyamine synthesis inhibitor is a hydrophobic polyamine analog of Formula (PT-VI), (PT-VII), (PT-VIII), or (PT-IX):

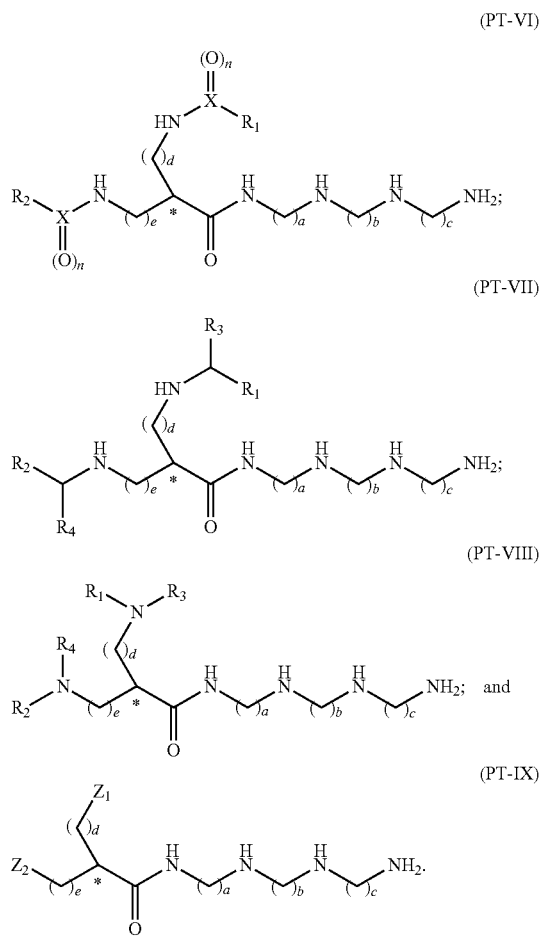

In compounds of Formula (PT-VI): a, b, and c independently range from 1 to 10; d and e independently range from 0 to 30; each X is independently either a carbon (C) or sulfur (S) atom, and $R_1$ and $R_2$ are independently selected from H or from the group of a straight or branched $C_1$-$C_{50}$ saturated or unsaturated aliphatic, carboxyalkyl, carbalkoxyalkyl, or alkoxy; a $C_1$-$C_8$ alicyclic; a single or multiring aryl substituted or unsubstituted aliphatic; an aliphatic-substituted or unsubstituted single or multiring aromatic; a single or multiring heterocyclic; a single or multiring heterocyclic aliphatic; a $C_1$-$C_{10}$ alkyl; an aryl sulfonyl; or cyano; or each of $R_1X\{O\}_n$— and $R_2X\{O\}_n$— are independently replaced by H; wherein * denotes achiral carbon position; and wherein if X is C, then n is 1; if X is S, then n is 2; and if X is C, then the XO group may be $CH_2$ such that n is 0.

In compounds of Formula (PT-VII): a, b, and c independently range from 1 to 10 and d and e independently range from 0 to 30; and $R_1$, $R_2$, $R_3$, and $R_4$ may be the same or different and are independently selected from H or from the group of a straight or branched $C_1$-$C_{50}$ saturated or unsaturated aliphatic, carboxyalkyl, carbalkoxyalkyl, or alkoxy; a $C_1$-$C_8$ alicyclic; a single or multiring aryl substituted or unsubstituted aliphatic; an aliphatic-substituted or unsubstituted single or multiring aromatic; a single or multiring heterocyclic; a single or multiring heterocyclic aliphatic; a $C_1$-$C_{10}$ alkyl; an aryl sulfonyl; or cyano.

In compounds of Formula (PT-VIII): a, b, and c independently range from 1 to 10 and d and e independently range from 0 to 30; and $R_1$, $R_2$, $R_3$, and $R_4$ may be the same or different and are independently selected from H or from the group of a straight or branched $C_1$-$C_{50}$ saturated or unsaturated aliphatic, carboxyalkyl, carbalkoxyalkyl, or alkoxy; a $C_1$-$C_8$ alicyclic; a single or multiring aryl substituted or unsubstituted aliphatic; an aliphatic-substituted or unsubstituted single or multiring aromatic; a single or multiring heterocyclic; a single or multiring heterocyclic aliphatic; a $C_1$-$C_{10}$ alkyl; an aryl sulfonyl; or cyano.

In compounds of Formula (PT-IX): a, b, and c independently range from 1 to 10 and d and C independently range from 0 to 30; and wherein $Z_1$ is $NR_1R_3$ and $Z_2$ is selected from —$R_1$, —$CHR_1R_2$ or —$CR_1R_2R_3$ or $Z_2$ is $NR_2R_4$ and $Z_1$ is selected from —$R_1$, —$CHR_1R_2$ or —$CR_1R_2R_3$, wherein $R_1$, $R_2$, and $R_3$ may be the same or different and are independently selected from H or from the group of a straight or branched $C_1$-$C_{50}$ saturated or unsaturated aliphatic, carboxyalkyl, carbalkoxyalkyl, or alkoxy; a $C_1$-$C_8$ alicyclic; a single or multiring aryl substituted or unsubstituted aliphatic; an aliphatic-substituted or unsubstituted single or multiring aromatic; a single or multiring heterocyclic; a single or multiring heterocyclic aliphatic; a $C_1$-$C_{10}$ alkyl; an aryl sulfonyl; or cyano.

In still another alternative, the polyamine transport inhibitor and/or polyamine synthesis inhibitor is a polyamine analog of formula $R_1$—X—$R_2$, wherein $R_1$ and $R_2$ are independently H or a moiety selected from the group consisting of a straight or branched $C_1$-$C_{10}$ aliphatic, alicyclic, single or multiring aromatic, single or multi-ring aryl substituted aliphatic, aliphatic-substituted single or multiring aromatic, a single or multiring heterocyclic, a single or multi-ring heterocyclic-substituted aliphatic and an aliphatic-substituted aromatic, and halogenated forms thereof; and X is a polyamine with two terminal amino groups, —$(CH_2)_3$—NH—, or —$CH_2$-Ph-$CH_2$—.

In yet another alternative, the polyamine transport inhibitor and/or polyamine synthesis inhibitor is a compound of formula $R_1$—X—$R_2$, wherein $R_1$ and $R_2$ are each a polyamine or an analog or derivative of a polyamine and X is a linker moiety connecting the two polyamine moieties.

In still another alternative, the polyamine transport inhibitor and/or polyamine synthesis inhibitor is a conformationally restricted polyamine analog that is a compound of formula E-NH-D-NH—B-A-B—NH-D-NH-E, wherein: A is selected from the group consisting of $C_2$-$C_6$ alkenyl and $C_3$-$C_6$ cycloalkyl, cycloalkenyl, and cycloakyl; B is independently selected from the group consisting of a single bond and $C_1$-$C_6$ alkyl and alkenyl; D is independently selected from the group consisting of $C_1$-$C_6$ alkyl and alkenyl, and $C_3$-$C_6$ cycloalkyl, cycloalkenyl, and cycloaryl; E is independently selected from the group consisting of H, $C_1$-$C_6$ alkyl and alkenyl.

In still another alternative, the polyamine transport inhibitor and/or polyamine synthesis inhibitor is an inhibitor of polyamine transport that is a synthetic derivative of a dimer of an original polyamine, wherein the original polyamine is modified to comprise an amido group immediately linked to a carbon atom of the original polyamine and being located between two internal atoms, the dimer being linked together by a spacer side chain anchored to the amido group of each monomer.

In yet another alternative, the polyamine transport inhibitor and/or polyamine synthesis inhibitor is a polyamine analog of the formula R—NH—$(CH_2)$—NH—$(CH_2)_x$—

NH—(CH$_2$)$_y$—NH—(CH$_2$)$_z$—NH—R$_2$, wherein R$_1$ and R$_2$ are hydrocarbon chains of 1 to 5 carbons and w, x, y, and z are integers of 1 to 10; one preferred polyamine analog of this formula is N$^1$,N$^{19}$-bis-(ethylamino)-5,10,15-triazanonadecane.

In still another alternative, the polyamine transport inhibitor and/or polyamine synthesis inhibitor is an oxidized polyamine; one preferred oxidized polyamine is N,N'-bis-(3-propionaldehyde)-1,4-diaminobutane (spermine bisaldehyde).

In still another alternative, the polyamine transport inhibitor and/or polyamine synthesis inhibitor is selected from the group consisting of AMXT 1426, AMXT 1501, AMXT 1505, and AMXT 1569.

In still another alternative, the polyamine transport inhibitor and/or polyamine synthesis inhibitor is a polyamine transport inhibitor with increased stability, such as di-substituted aryl polyamine compounds with the structure R'HN—(CH$_2$)$_x$—NH—(CH$_2$)$_y$—NH—CH$_2$—R—CH$_2$—NH—(CH$_2$)$_{xx}$—NH—(CH$_2$)$_{yy}$—NHR" wherein R is selected from the group consisting of anthracene, naphthalene, and benzene; wherein R' and R" are independently selected from the group consisting of H and an alkyl group; and wherein x, xx, y, and yy are independently selected from the group consisting of 3 and 4.

In another alternative of a pharmaceutical composition according to the present invention, the composition further comprises a therapeutically effective quantity of an S-adenosylmethionine decarboxylase inhibitor. The S-adenosylmethionine decarboxylase can be, but is not limited to, SAM486A (an S-adenosylmethionine decarboxylase inhibitor, 4-(aminoiminomethyl)-2,3-dihydro-1H-inden-1-one-diaminomethylenehydrazone).

In still another alternative of a pharmaceutical composition, the composition further comprises a therapeutically effective quantity of a retinoid. The retinoid can be, but is not limited to, retinol, retinal, tretinoin, isotretinoin, alitretinoin, etretinate, acitretin, tazarotene, bexarotene, adapalene, seletinoid G, fenritidine, 13-cis-retinoic acid, 11-cis-retinal, 9-cis-retinal, derivatives of 11-cis-retinal or 9-cis-retinal that are acyclic retinals; retinals with modified polyene chain length, such as trienoic or tetraenoic retinals; retinals with substituted polyene chains, such as alkyl-substituted, halo-substituted, or heteroatom-substituted polyene chains; retinals with modified polyene chains, such as trans- or cis-locked polyene chains or with polyene chains including allene or alkyne modifications; and retinals with ring modifications, such as heterocyclic, heteroaromatic, or substituted cycloalkene rings. Particular retinoids include, but are not limited to, 9-ethyl-11-cis-retinal, 7-methyl-1-cis-retinal, 13-desmethyl-11-cis-retinal, 11-cis-10-F-retinal, 11-cis-10-CI-retinal, 11-cis-10-methyl-retinal, 11-cis-10-ethyl-retinal, 9-cis-10-F-retinal, 9-cis-10-CI-retinal, 9-cis-10-methyl-retinal, 9-cis-10-ethyl-retinal, 11-cis-12-F-retinal, 11-cis-12-CI-retinal, 11-cis-12-methyl-retinal, 11-cis-10-ethyl-retinal, 9-cis-12-F-retinal, 9-cis-12-CI-retinal, 9-cis-12-methyl-retinal 11-cis-14-F-retinal, 11-cis-14-methyl-retinal, 11-cis-14-ethyl-retinal, 9-cis-14-F-retinal, 9-cis-14-methyl-retinal, 9-cis-14-ethyl-retinal, and other derivatives.

Additional retinol derivatives that can be included in pharmaceutical compositions according to the present invention include retinol derivatives of Formula (R-I):

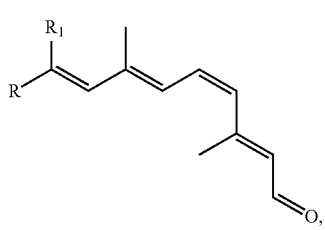

(R-I)

wherein R and R$_1$ are each independently selected from linear alkyl groups, iso-alkyl groups, sec-alkyl groups, tert-alkyl groups, other branched alkyl groups, substituted branched alkyl groups, hydroxyl groups, hydroxyalkyl groups, amine groups, and amide groups.

Further additional retinol derivatives that can be included in pharmaceutical compositions according to the present invention include retinol derivatives of Formula (R-II):

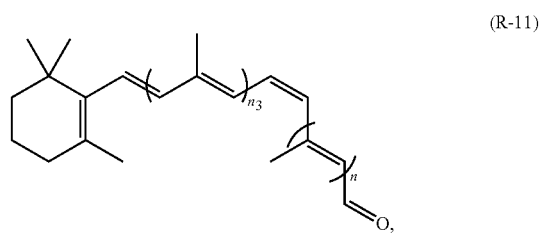

(R-II)

wherein n and n$_1$ are each 0, 1, 2, or 3 alkyl, alkene, or alkylene groups with the proviso that the sum of n and n$_1$ is at least 1.

Further additional retinol derivatives that can be included in pharmaceutical compositions according to the present invention include retinol derivatives of Formula (R-III):

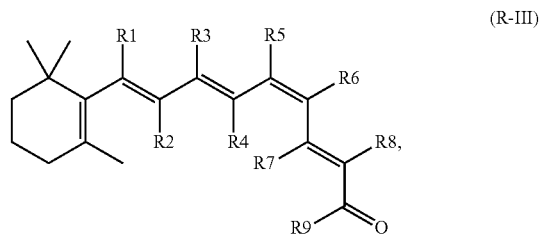

(R-III)

wherein each of R1, R2, R3, R4, R5, R6, R7, R8, and R9 are independently selected from the group consisting of hydrogen, alkyl, branched alkyl, cycloalkyl, halogen, and a heteroatom.

Further additional retinol derivatives that can be included in pharmaceutical compositions according to the present invention include retinol derivatives of Formula (R-IV), (R-V), and (R-VI):

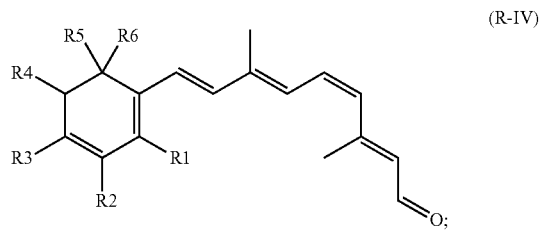

(R-IV)

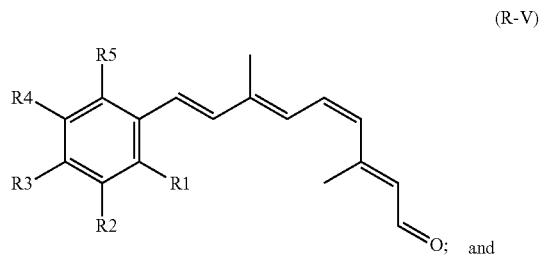

(R-V)

and

-continued (R-VI)

wherein each of R1, R2, R3, R4, R5, and R6, as applicable to the particular structure, is selected from the group consisting of hydrogen, alkyl, substituted alkyl, hydroxyl, hydroxyalkyl, amine, amide, halo, or a heteroatom; in Formula (R-VI), X is sulfur, silicon, nitrogen, or fluoro- or bromo-substituted carbon.

Further additional retinol derivatives that can be included in pharmaceutical compositions according to the present invention include retinol derivatives of Formula (R-VII):

(R-VII)

wherein R is hydrogen, methyl, or another lower alkane or branched alkane, n is 0, 1, 2, 3, or 4, and m plus I is 1, 2, or 3, these derivatives are cis-locked. A particular example is the retinoid of Formula (R-VIII), wherein n is 1, 2, 3, or 4:

(R-VIII)

Further additional retinol derivatives that can be included in pharmaceutical compositions according to the present invention include retinol derivatives of Formula (R-IX):

(R-IX)

wherein each of $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, and $R_{15}$ are independently selected from the group consisting of hydrogen, alkyl, branched alkyl, halogen, hydroxyl, hydroxyalkyl, amine, amide, or a heteroatom, and each of n and $n_1$ can be independently selected from 0, 1, 2, or 3 alkyl, alkene, or alkylene groups, with the proviso that the sum of n and $n_1$ is at least 1; in addition, $R_{11}$-$R_{12}$ and/or $R_{13}$-$R_{14}$ can comprise an alkene group in the cyclic carbon ring, and $R_5$ and $R_7$ together can form a cycloalkyl group or substituted cycloalkyl group.

In yet another alternative of a pharmaceutical composition according to the present invention, the composition further comprises a therapeutically effective quantity of a syrbactin compound such as glidobactin A or syringolin A.

In yet another alternative of a pharmaceutical composition according to the present invention, the composition further comprises a therapeutically effective quantity of a non-steroidal anti-inflammatory compound selected from the group consisting of acetylsalicylic acid (aspirin), sodium salicylate, choline magnesium trisalicylate, salsalate, diflunisal, sulfasalazine, olsalazine, acetaminophen, indomethacin, sulindac, tolmetin, diclofenac, ketorolac, ibuprofen, naproxen, flurbiprofen, ketoprofen, fenoprofin, oxaprozin, mefenamic acid, meclofenamic acid, piroxicam, meloxicam, nabumetone, etodolac, nimesulide, aceclofenac, alclofenac, alminoprofen, amfenac, ampiroxicam, apazone, araprofen, azapropazone, bendazac, benoxaprofen, benzydamine, bermoprofen, benzpiperylon, bromfenac, bucloxic acid, bumadizone, butibufen, carprofen, cinmetacin, cinnoxicam, clidanac, clofezone, clonixin, clopirac, darbufelone, droxicam, eltenac, enfenamic acid, epirizole, esflurbiprofen, ethenzamide, etofenamate, felbinac, fenbufen, fenclofenac, fenclozic acid, fenclozine, fendosal, fentiazac, feprazone, filenadol, flobufen, florifenine, flosulide, flubichin methanesulfonate, flufenamic acid, flufenisal, flunixin, flunoxaprofen, fluprofen, fluproquazone, furofenac, ibufenac, indoprofen, isofezolac, isoxepac, isoxicam, licofelone, lobuprofen, lomoxicam, lonazolac, loxaprofen, mabuprofen, miroprofen, mofebutazone, mofezolac, morazone, nepafanac, niflumic acid, nitrofenac, nitroflurbiprofen, nitronaproxen, orpanoxin, oxaceprol, oxindanac, oxpinac, oxyphenbutazone, pamicogrel, parcetasal, parsalmide, pelubiprofen, pemedolac, phenylbutazone, pirazolac, pirprofen, pranoprofen, salicin, salicylamide, salicylsalicylic acid, satigrel, sudoxicam, suprofen, talmetacin, talniflumate, tazofelone, tebufelone, tenidap, tenoxicam, tepoxalin, tiaprofenic acid, tiaramide, tinoridine, tiopinac, tioxaprofen, tolfenamic acid, triflusal, tropesin, ursolic acid, ximoprofen, zaltoprofen, zidometacin, and zomepirac.

In yet another alternative of a pharmaceutical composition according to the present invention, the composition further comprises a therapeutically effective quantity of a cyclooxygenase-2 inhibitor selected from the group consisting of lumiracoxib, celecoxib, cimicoxib, imrecoxib, rofecoxib, etoricoxib, valdecoxib, tilmacoxib, parecoxib, and deracoxib.

In yet another alternative of a pharmaceutical composition according to the present invention, the composition further comprises a therapeutically effective quantity of an agent which reduces blood glutamate levels and enhances brain to blood glutamate efflux. The agent that reduces blood glutamate levels and enhances brain to blood glutamate efflux can be: (1) a transaminase that can be selected from the group consisting of glutamate oxaloacetate transaminase, glutamate pyruvate transaminase, acetylornithine transaminase, ornithine-oxo-acid transaminase, succinyldiaminopimelate transaminase, 4-aminobutyrate transaminase, (s)-3-amino-2-methylpropionate transaminase, 4-hydroxyglutamate transaminase, diiodotyrosine transaminase, thyroid-hormone transaminase, tryptophan transaminase, diamine transaminase, cysteine transaminase, L-lysine 6-transaminase, histidine transaminase, 2-aminoadipate transaminase, glycine transaminase, branched-chain-amino-acid transaminase, 5-aminovalerate transaminase, dihydroxyphenylalanine transaminase, tyrosine transaminase, phosphoserine transaminase, taurine transaminase, aromatic-amino-acid transaminase, aromatic-amino-acid-glyoxylate transaminase, leucine transaminase, 2-aminohexanoate transaminase, ornithine(lysine) transaminase, kynurenine-oxoglutarate transaminase, D-4-hydroxyphenylglycine transaminase, cysteine-conjugate transaminase, 2,5-diaminovalerate transaminase, histidinol-phosphate transaminase, diaminobutyrate-2-oxoglutarate transaminase, and UDP-2-acetamido-4-amino-2,4,6-trideoxyglucose transaminase; (2) a glutamate dehydrogenase; (3) a glutamate decarboxylase; (4) a glutamate-ethylamine ligase; (5) a transferase that can be selected from the group consisting of glutamate N-acetyltransferase and adenylyltransferase; (6) an aminomutase that can be glutamate-1-semialdehyde 2,1-aminomutase; and (7) a racemase. The enzyme can be used with a cofactor, and the cofactor can be included in the composition.

In yet another alternative of a pharmaceutical composition according to the present invention, the composition further comprises a therapeutically effective quantity of castanospermine or an ester of castanospermine.

In yet another alternative of a pharmaceutical composition according to the present invention, the composition further comprises a therapeutically effective quantity of an aziridinyl putrescine compound such as 1-(4-aminobutyl)aziridine.

In yet another alternative of a pharmaceutical composition according to the present invention, the composition further comprises a therapeutically effective quantity of an interferon or an interferon inducer. The interferon inducer can be tilorone or an analog thereof.

In yet another alternative of a pharmaceutical composition according to the present invention, the composition further comprises a therapeutically effective quantity of 2,4-disulfonyl phenyl tert-butyl nitrone (2,4-ds-PBN).

In yet another alternative of a pharmaceutical composition according to the present invention, the composition further comprises a therapeutically effective quantity of 3-(4-amino-1-oxo-1,3-dihydro-isoindol-2-yl)-piperidine-2,6-dione.

In yet another alternative of a pharmaceutical composition according to the present invention, the composition further comprises a therapeutically effective quantity of an agent selected from the group consisting of thalidomide and lenalidomide.

In yet another alternative of a pharmaceutical composition according to the present invention, the composition further comprises a therapeutically effective quantity of an agent selected from the group consisting of N-2-pyridinyl-2-pyridinecarbothioamide and cambendazole.

In yet another alternative of a pharmaceutical composition according to the present invention, the composition further comprises a therapeutically effective quantity of an inhibitor of histone demethylase. The inhibitor of histone demethylase can be selected from the group consisting of an oligoamine and a polyamine. In one alternative, the polyamine is a compound of Formula (P-I):

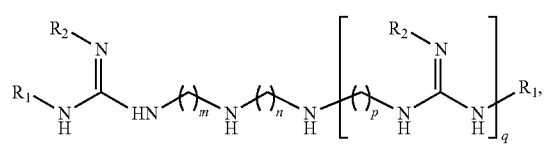
(P-I)

wherein:
(1) n is an integer from 1 to 12;
(2) m and p are each independently an integer from 1 to 5;
(3) q is 0 or 1;
(4) each $R_1$ is independently selected from the group consisting of: $C_1$-$C_8$ substituted or unsubstituted alkyl, $C_4$-$C_{15}$ substituted or unsubstituted cycloalkyl, $C_3$-$C_{15}$ substituted or unsubstituted branched alkyl, $C_6$-$C_{20}$ substituted or unsubstituted aryl, $C_6$-$C_{20}$ substituted or unsubstituted heteroaryl, $C_7$-$C_{24}$ substituted or unsubstituted aralkyl, and $C_7$-$C_{24}$ substituted or unsubstituted heteroaralkyl; and
(5) each $R_2$ is independently selected from hydrogen or a $C_1$-$C_8$ substituted or unsubstituted alkyl. In another alternative, the oligoamine is an oligoamine of Formula (O-I):

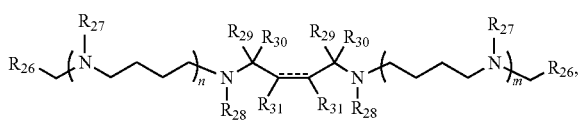
(O-I)

wherein:
(1) n and m are each independently an integer from 1 to 12;
(2) each $R_{26}$, $R_{27}$, $R_{28}$, $R_{29}$, $R_{30}$, and $R_{31}$ is independently selected from hydrogen, a $C_1$-$C_8$ substituted or unsubstituted alkyl, a $C_6$-$C_{20}$ substituted or unsubstituted aryl, and an amine; and
(3) ≈≈≈≈≈ is a single bond or double bond.

In yet another alternative of a pharmaceutical composition according to the present invention, the composition further comprises a therapeutically effective quantity of an aryl substituted xylopyranoside derivative. These compounds are disclosed in United States Patent Application Publication No. 2008/0027023 by Ellervik et al., and include xylose based glycoside compounds that have xylose linked O-, S- or C-glycosidically to an aglycone containing several aromatic rings.

In yet another alternative of a pharmaceutical composition according to the present invention, the composition further comprises a quantity of an agent that increases the ability of the eflornithine or derivative, analog, or prodrug thereof to pass through the blood-brain barrier, wherein the quantity of the agent that increases the ability of the eflornithine or derivative, analog, or prodrug thereof to pass through the blood-brain barrier is sufficient to provide a therapeutically effective dose of the eflornithine or derivative, analog, or prodrug thereof to a tissue of the central nervous system. Typically, the agent that increases the ability of the eflornithine or derivative, analog, or prodrug thereof to pass through the blood-brain barrier is an agent selected from the group consisting of:
(a) a chimeric peptide of the structure of Formula (D-III):

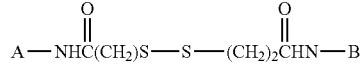
(D-III)

wherein: (A) A is somatostatin, thyrotropin releasing hormone (TRH), vasopressin, alpha interferon, endorphin, muramyl dipeptide or ACTH 4-9 analogue; and (B) B is insulin, IGF-I, IGF-II, transferrin, cationized (basic) albumin or prolactin; or a chimeric peptide of the structure of Formula (D-III) wherein the disulfide conjugating bridge between A and B is replaced with a bridge of Subformula (D-III(a)):

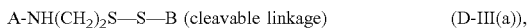

A-NH(CH$_2$)$_2$S—S—B (cleavable linkage)    (D-III(a)), wherein the bridge is formed using cysteamine and EDAC as the bridge reagents; or a chimeric peptide of the structure of Formula (D-III) wherein the disulfide conjugating bridge between A and B is replaced with a bridge of Subformula (D-III(b)):

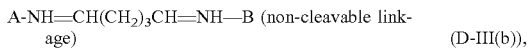

A-NH=CH(CH$_2$)$_3$CH=NH—B (non-cleavable linkage)    (D-III(b)), wherein the bridge is formed using glutaraldehyde as the bridge reagent;
  (b) a composition comprising either avidin or an avidin fusion protein bonded to a biotinylated eflornithine or analog or derivative thereof to form an avidin-biotin-agent complex including therein a protein selected from the group consisting of insulin, transferrin, an anti-receptor monoclonal antibody, a cationized protein, and a lectin;
  (c) a neutral liposome that is pegylated and incorporates the eflornithine or analog or derivative thereof, wherein the polyethylene glycol strands are conjugated to at least one transportable peptide or targeting agent;
  (d) a humanized murine antibody that binds to the human insulin receptor linked to the eflornithine or analog or derivative thereof through an avidin-biotin linkage; and
  (e) a fusion protein comprising a first segment and a second segment: the first segment comprising a variable region of an antibody that recognizes an antigen on the surface of a cell that after binding to the variable region of the antibody undergoes antibody-receptor-mediated endocytosis, and, optionally, further comprises at least one domain of a constant region of an antibody; and the second segment comprising a protein domain selected from the group consisting of avidin, an avidin mutein, a chemically modified avidin derivative, streptavidin, a streptavidin mutein, and a chemically modified streptavidin derivative, wherein the fusion protein is linked to the eflornithine or analog or derivative thereof by a covalent link to biotin.

In still another alternative, the composition further comprises a therapeutically effective quantity of an immunomodulatory agent selected from the group consisting of: (a) IL-15; (b) anti-PD1 antibodies; (c) anti-B7-H1 antibodies; (d) IL-12; (e) QS-21; (f) CD-40; (g) anti-CD40 antibody acting as a CD40 agonist; (h) CD40L; (i) IL-7; (j) CpG; (k) 1-methyltryptophan; (l) anti-CD137 antibodies; (m) anti-TGF-β antibodies; (n) anti-IL10 antibodies; (o) anti-ILR10R antibodies; (p) Flt3L; (q) Anti-GITR; (r) CCL21 or a nucleic acid encoding CCL21; (s) monophosphoryl lipid A; (t) poly I:C; (u) poly ICLC; (v) anti-OX40 antibodies; (w) anti-B7-H4 antibodies; (x) an immune response modulator selected from the group consisting of: resiquimod; N-[4-(4-amino-2-ethylimidazo[4,5-c]quinolin-1-yl)butyl]methanesulfonamide); imiquimod; 2-ethoxymethyl)-1H-imidazo[4,5-c]quinolin-4-amine; 2-propylthiazolo[4,5-c]quinolin-4-amine; isatoribine; ANA975, ANA-773; and GS-9620; (y) LIGHT or a nucleic acid encoding LIGHT; (z) antibodies to LAG-3; and (aa) antibodies to CTLA4.

IL-15 is disclosed in: U.S. Pat. No. 6,258,352 to Shimonaka; U.S. Pat. No. 7,858,081 to Bernard et al. (mutants in the epitope of IL-15 that is responsible for binding to the interleukin-15 receptor α-chain); U.S. Pat. No. 8,124,084 to Lefrancois et al. (use of IL-5 and soluble IL-15R for stimulating an immune response); U.S. Pat. No. 8,163,879 to Wong et al. (fusion molecules and IL-15 variants); U.S. Pat. No. 8,173,786 to Weiner et al. (fusion protein comprising non-IL-15 signal peptides linked to IL-15 protein sequences); U.S. Pat. No. 8,178,660 to Weiner et al. (vaccines and immunotherapeutics using codon-optimized IL-15); and U.S. Pat. No. 8,415,456 to Nellis et al. (IL-15 polypeptides with substitutions to reduce deamination and increase stability).

Anti-PD1 antibodies are disclosed in U.S. Pat. No. 8,735,553 to Li et al. Anti-B7-H1 antibodies are disclosed in U.S. Pat. No. 8,981,063 to Chen.

IL-12 is disclosed in U.S. Pat. No. 6,929,794 to Mills et al.; U.S. Pat. No. 7,374,751 to Hancock (QS-21 and IL-12 as an adjuvant combination; QS-21 is a mixture including water-soluble triterpene glucosides); U.S. Pat. No. 786,788 to Felzmann (dendritic cells expressing IL-12); U.S. Pat. No. 9,233,156 to Har-Noy (induction of IL-12 with activated allogeneic cells); U.S. Pat. No. 8,765,462 to Medin et al. (IL-12 immunotherapy for cancer); U.S. Pat. No. 5,571,515 to Scott et al. (use of IL-12 as an adjuvant); U.S. Pat. No. 5,853,714 to Deetz et al. (purification methods for IL-12); and U.S. Pat. No. 6,303,114 to Metzger et al. (IL-12 enhancement of immune responses to T-independent antigens).

CD40 and CD40L or agonists, including antibodies that act as agonists, for these proteins are disclosed in U.S. Pat. No. 9,315,559 to Spencer (methods for activating an antigen-presenting cell by inducing an inducible pattern recognition receptor adapter or adapter fragment and CD40 activity); U.S. Pat. No. 9,161,976 to Noelle et al. (immunotherapy using TLR9 ligand and CD40 ligand); and U.S. Pat. No. 9,095,608 to Kedl et al. (CD40L polypeptide or agonistic anti-CD40 antibody, where the antibody itself acts as an agonist).

IL-7 is disclosed in U.S. Pat. No. 5,637,323 to Wiltrout et al. (use to stimulate pluripotential hematopoietic stem cells); U.S. Pat. No. 7,323,549 to Lauder et al. (fusion proteins including an immunoglobulin chain and IL-7); U.S. Pat. No. 7,585,947 to Morre et al. (conformers with reduced immunogenicity); and U.S. Pat. No. 7,589,179 to Gillies et al. (variants with reduced immunogenicity).

The use of CpG as an adjuvant is disclosed in B. V. Stern et al., "Vaccination with Tumor Peptide in CpG Adjuvant Protects Via IFN-Gamma-Dependent CD4 Cell Immunity," J. Immunol. 168: 6099-6105 (2002) and in U.S. Pat. No. 8,906,381 to Iannacone et al. (CpG is a TLR9 agonist).

The use of 1-methyltryptophan is disclosed in U.S. Pat. No. 7,879,791 to Munn et al. The compound 1-methyltryptophan is an inhibitor of the enzyme indoleamine 2,3-dioxygenase, which can act to potentiate T-cell suppression.

The use of anti-CD137 antibodies is disclosed in U.S. Pat. No. 9,079,976 to Shirwan et al. The anti-CD137 antibodies can act as a ligand for 4-1BBL and thus stimulate T cell function.

The use of anti-TGF-β antibodies is disclosed in U.S. Pat. No. 9,145,458 to Bedinger et al., U.S. Pat. No. 9,090,685 to Ledbetter et al., and U.S. Pat. No. 8,012,482 to Adams et al.

The use of anti-IL10 or anti-IL10R is disclosed in U.S. Pat. No. 8,956,607 to Osterroth et al. (humanized IL-10); U.S. Pat. No. 7,794,710 to Chen et al. (IL-10 involved in promoting apoptosis of T cells); and U.S. Pat. No. 7,553,932 to Von Herrath et al. (anti-IL10R antibodies).

Flt3L is a ligand for Flt3 and acts as a cytokine and is important for the generation and mobilization of dendritic cells (K. R. Diener et al., "Human Flt-3 Ligand-Mobilized Dendritic Cells Require Additional Activation to Drive Effective Immune Responses," *Exp. Hematol.* 36: 51-60 (2008)). Flt3L is a polypeptide that exists, in humans, in a number of isoforms (GenBank: AAI44130.1). Flt3L promotes migration of dendritic cells to lymph nodes where priming can occur.

Anti-GITR antibodies that can act as immune stimulators are disclosed in U.S. Pat. No. 8,709,424 to Schebye et al. The antibodies can act as activators for GITR.

CCL21 is a cytokine containing 134 amino acids that has a 37-amino-acid basic extension. CCL21 binds to CCR7. The gene for CCL21 can be delivered for subsequent in vivo expression by various viral vectors known in the art, including, but not limited to, adenoviral vectors or retroviral vectors (U. Thanarajasingam et al., "Delivery of CCL21 to Metastatic Disease Improves the Efficacy of Adoptive T-Cell Therapy," *Cancer Res.* 67: 300-308 (2007)).

Monophosphoryl lipid A is an adjuvant; its use is disclosed in U.S. Pat. No. 9,376,726 to Fouchier et al. and in U.S. Pat. No. 9,375,471 to Baudner et al. Monophosphoryl lipid A is an agonist of TLR4.

Poly I:C (polyinosinic:polycytidylic acid) is an adjuvant (M. E. Fortier et al., "The Viral Mimic, Polyinosinic:Polycytidylic Acid," Induces Fever in Rats via an Interleukin-1-Dependent Mechanism," *Am. J. Physiol. Requl. Inteqr. Comp. Physiol.* 287: R759-R766 (2004). It is a mimic of double-stranded viral RNA and thus is a TLR3 agonist. Poly ICLC is an analog of poly I:C that is a polyinosinic acid polycytidylic acid poly-L-lysine carboxy-methylcellulose complex and that also acts as an adjuvant; it is disclosed in U.S. Pat. No. 8,303,965 to Lin.

Anti-OX40 antibodies are disclosed in U.S. Pat. No. 9,006,399 to Liu et al. and in U.S. Pat. No. 9,163,085 to Liu et al. These antibodies have a high affinity for OX40 and act as agonists for that receptor. The activation of OX40 indirectly blocks production of the immunosuppressive cytokine IL-10 by Tr1 cells and other IL-10-producing cells.

Anti-B7-H4 antibodies are disclosed in U.S. Pat. No. 9,279,008 to Scholler et al. B7-H4 acts as an inhibitory regulator of T-cell expression. When present at the surface of antigen presenting cells, B7-H4 negatively regulates T cell activation. Antibodies to B7-H4 can reverse inhibition of T-cell activation and thereby reverse immunosuppression.

Resiquimod (1-[4-amino-2-(ethoxymethyl)imidazo[4,5-c]quinolin-1-yl]-2-methylpropan-2-ol) acts as immune response modifier and can be used as an adjuvant; it is disclosed in U.S. Pat. No. 5,939,090 to Beaurline et al. and U.S. Pat. No. 6,365,166 to Beaurline et al. It is an agonist for TLR7 and TLR8. The agent 852A (N-[4-(4-amino-2-ethylimidazo[4,5-c]quinolin-1-yl)butyl]methanesulfonamide) also acts as a TLR7/TLR8 agonists. Other agents have similar activities, including imiquimod, CL097 (2-ethoxymethyl)-1H-imidazo[4,5-c]quinolin-4-amine), CL075 (2-propylthiazolo[4,5-c]quinolin-4-amine), isatoribine, ANA975, ANA773, and GS-9620.

LIGHT is a ligand for TNFRSF14, a receptor that is a member of the tumor necrosis factor receptor superfamily; LIGHT is a member of the TNF ligand superfamily. It functions as a costimulatory factor for the activation of lymphoid cells and stimulates the proliferation of T cells. It is described in D. Yang et al., "LIGHT, a New Member of the TNF Superfamily," *J. Biol. Regul. Homeostat. Agents* 16: 206-210 (2003). LIGHT and adenoviral vectors for transfection and expression of LIGHT are disclosed in U.S. Pat. No. 9,272,025 to Fu.

Anti-Lymphocyte Activation Gene-3 (LAG-3) antibodies can inhibit the action of this T-cell checkpoint receptor. LAG-3 negatively regulates the proliferation and activation of T cells. Antibodies to LAG-3 are disclosed in U.S. Pat. No. 9,132,281 to Zeng et al.

Anti-CTLA4 antibodies are disclosed in U.S. Pat. No. 9,327,014 to Gurney et al.; U.S. Pat. No. 9,320,811 to Jure-Kunkel (ipilimumab and tremelimumab); and U.S. Pat. No. 9,062,111 to Nichol et al.

As used herein, unless further defined or limited, the term "antibody" encompasses both polyclonal and monoclonal antibodies, as well as genetically engineered antibodies such as chimeric, humanized or fully human antibodies of the appropriate binding specificity. As used herein, unless further defined, the term "antibody" also encompasses antibody fragments such as sFv, Fv, Fab, Fab' and F(ab)'$_2$ fragments. In many cases, it is preferred to use monoclonal antibodies. In some contexts, antibodies can include fusion proteins comprising an antigen-binding site of an antibody, and any other modified immunoglobulin molecule comprising an antigen recognition site (i.e., antigen-binding site) as long as the antibodies exhibit the desired biological activity. An antibody can be any of the five major classes of immunoglobulins: IgA, IgD, IgE, IgG, and IgM, or subclasses (isotypes) thereof (e.g., IgG1, IgG2, IgG3, IgG4, IgA1, and IgA2), based on the identity of their heavy chain constant domains referred to as alpha, delta, epsilon, gamma, and mu, respectively. The different classes of immunoglobulins have different and well-known subunit structures and three-dimensional configurations. Antibodies can be naked or conjugated to other molecules, including but not limited to, toxins, antineoplastic agents, antimetabolites, or radioisotopes, in some cases, conjugation occurs through a linker or through noncovalent interactions such as an avidin-biotin or streptavidin-biotin linkage.

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, single chain antibodies, and multispecific antibodies formed from antibody fragments. "Antibody fragment" as used herein comprises an antigen-binding site or epitope-binding site. The term "variable region" of an antibody refers to the variable region of an antibody light chain, or the variable region of an antibody heavy chain, either alone or in combination. The variable regions of the heavy and light chains each consist of four framework regions (FR) connected by three complementarity determining regions (CDRs), also known as "hypervariable regions." The CDRs in each chain are held together in close proximity by the framework regions and, with the CDRs from the other chain, contribute to the formation of the antigen-binding site of the antibody. There are at least two techniques for determining CDRs: (1) an approach based on cross-species sequence variability (i.e., Kabat et al., 1991, Sequences of Proteins of Immunological Interest, 5th Edition, National Institutes of Health, Bethesda, Md.), and (2) an approach based on crystallographic studies of antigen-antibody complexes (Al-Lazikani et al., 1997, J. Mol. Biol., 273:927-948). In addition, combinations of these two approaches are sometimes used in the art to determine CDRs. The term "monoclonal antibody" as used herein refers to a homogeneous antibody population involved in the highly specific recognition and binding of a single antigenic determinant or epitope. This is in contrast to polyclonal antibodies that typically include a mixture of different antibodies directed against a variety of different antigenic determinants. The term "monoclonal antibody" encompasses both intact and full-length monoclonal antibodies as well as antibody fragments (e.g., Fab, Fab', F(ab')2, Fv), single chain (sFv) antibodies, fusion proteins comprising an antibody portion, and any other modified immunoglobulin molecule comprising an antigen recognition site (antigen-binding site). Furthermore, "monoclonal antibody" refers to such antibodies made by any number of techniques, including but not limited to, hybridoma production, phage selection, recombinant expression, and expression in transgenic animals. The term "humanized antibody" as used herein refers to forms of non-human (e.g., murine) antibodies that are specific immunoglobulin chains, chimeric immunoglobulins, or fragments thereof that contain minimal non-human sequences. Typically, humanized antibodies are human immunoglobulins in which residues of the CDRs are replaced by residues from the CDRs of a non-human species (e.g., mouse, rat, rabbit, or hamster) that have the desired specificity, affinity, and/or binding capability (Jones et al., 1986, Nature, 321:522-525; Riechmann et al., 1988, Nature, 332:323-327; Verhoeyen et al., 1988, Science, 239:1534-1536). In some instances, the Fv framework region residues of a human immunoglobulin are replaced with the corresponding residues in an antibody from a non-human species that has the desired specificity, affinity, and/or binding capability. The humanized antibody can be further modified by the substitution of additional residues either in the Fv framework region and/or within the replaced non-human residues to refine and optimize antibody specificity, affinity, and/or binding capability. In general, the humanized antibody will comprise substantially all of at least one, and typically two or three, variable domains containing all or substantially all of the CDRs that correspond to the non-human immunoglobulin whereas all or substantially all of the framework regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in, for example, U.S. Pat. No. 5,225,539. The term "human antibody" as used herein refers to an antibody produced by a human or an antibody having an amino acid sequence corresponding to an antibody produced by a human. A human antibody may be made using any of the techniques known in the art. This definition of a human antibody specifically excludes a humanized antibody comprising non-human CDRs. The term "chimeric antibody" as used herein refers to an antibody wherein the amino acid sequence of the immunoglobulin molecule is derived from two or more species. Typically, the variable region of both light and heavy chains corresponds to the variable region of antibodies derived from one species of mammals (e.g., mouse, rat, rabbit, or other antibody producing mammal) with the desired specificity, affinity, and/or binding capability, while the constant regions correspond to sequences in antibodies derived from another species (usually human). The terms "epitope" and "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids (also referred to as linear epitopes) are typically retained upon protein denaturing, whereas epitopes formed by tertiary folding (also referred to as conformational epitopes) are typically lost upon protein denaturing. An epitope typically includes at least 3, and more usually, at least 5 or 8-10 amino acids in a unique spatial conformation.

Antibodies that specifically bind to receptors may either inhibit or activate the receptors to which they specifically bind, depending on the specific epitope being targeted by the antibody. In some cases, when antibodies mimic the naturally-occurring agonist for a receptor, the binding of the antibody to the receptor activates the receptor and causes the receptor to initiate signal transduction. In other cases, the antibody may block the binding of the naturally-occurring agonist to the receptor by steric hindrance or other mechanisms.

When nucleic acid molecules, such as nucleic acid molecules encoding a peptide, polypeptide, or protein, are to be delivered in vivo for subsequent expression of the peptide, polypeptide, or protein encoded by the nucleic acid molecule, a vector as known in the art can be used. The terms "vector" or "vectors" refer to a nucleic acid molecule capable of transporting another nucleic acid to which it has been linked. A "vector" as used herein includes, but is not limited to, a viral vector, a plasmid, a RNA vector or a linear or circular DNA or RNA molecule which may consists of a chromosomal, non chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors." A vector as used herein comprises, but is not limited to, a YAC (yeast artificial chromosome), a BAC (bacterial artificial chromosome), a baculovirus vector, a phage, a phagemid, a cosmid, a viral vector, a plasmid, a RNA vector or a linear or circular DNA or RNA molecule which may consist of chromosomal, non chromosomal, semi-synthetic or synthetic DNA. In general, expression vectors of utility in recombinant DNA techniques are often in the form of "plasmids" which refer generally to circular double stranded DNA loops which, in their vector form are not bound to the chromosome. Large numbers of suitable vectors are known to those of skill in the art. Vectors can comprise selectable markers, for example: neomycin phosphotransferase, histidinol dehydrogenase, dihydrofolate reductase, hygromycin phosphotransferase, herpes simplex virus thymidine kinase, adenosine deaminase, glutamine synthetase, and hypoxanthine-guanine phosphoribosyl transferase for eukaryotic cell culture; TRP1 for *Saccharomyces cerevisiae*; tetracycline, rifampicin or ampicillin resistance in *Escherichia coli*. Preferably such vectors are expression vectors, wherein a sequence encoding a polypeptide of interest is placed under control of appropriate transcriptional and translational control elements to permit production or synthesis of said polypeptide. Therefore, the polynucleotide is included in an expression cassette. More particularly, the vector comprises a replication origin, a promoter operatively linked to the encoding polynucleotide, a ribosome binding site, a RNA-splicing site (when genomic DNA is used), a polyadenylation site and a transcription termination site. It also can comprise an enhancer or silencer elements. Selection of the promoter will depend upon the cell in which the polypeptide is expressed. Suitable promoters include tissue specific and/or inducible promoters. Examples of inducible promoters are: eukaryotic metallothionine promoter which is induced by increased levels of heavy metals, prokaryotic lacZ promoter which is induced in response to isopropyl-β-D-thiogalactopyranoside (IPTG) and eukaryotic heat shock promoter which is induced by increased temperature. Examples of tissue specific promoters are skeletal muscle creatine kinase, prostate-specific antigen (PSA), α-antitrypsin protease, human surfactant (SP) A and B proteins, β-casein and acidic whey protein genes. Delivery vectors and vectors can be associated or combined with any cellular permeabilization techniques such as sonoporation or electroporation or derivatives of these techniques. Viral vectors include retrovirus, adenovirus, parvovirus (e.g. adeno-associated viruses), coronavirus, negative strand RNA viruses such as orthomyxovirus (e.g., influenza virus), rhabdovirus (e.g., rabies and vesicular stomatitis virus), paramyxovirus (e.g. measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, and spumavirus. Viral vectors can also include lentiviral vectors, which are HIV-based vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells. Such lentiviral vectors can be either integrating or non-integrating. Another alternative is a shuttle vector. A shuttle vector is a vector that can replicate in two different species, such as a prokaryote such as *E. coli* and in mammalian cells, such as human cells, shuttle vectors that can replicate in both *E. coli* and in mammalian cells, including human cells, include adenoviral vectors.

Typically, when a composition according to the present invention includes eflornithine, the quantity of eflornithine in the composition is such that, when a unit dose of the composition is administered to a subject with a disease or condition treatable by administration of eflornithine, the dosage of eflornithine is from about 1 $g/m^2$ to about 5 $g/m^2$. Preferably, the dosage of eflornithine is about 2.8 $g/m^2$. In other alternatives, the dosage of eflornithine is about 3.6 $g/m^2$.

Typically, when a composition according to the present invention includes a derivative, analog, or prodrug of eflornithine, the quantity of the derivative, analog, or prodrug of eflornithine in the composition is such that, when a unit dose of the composition is administered to a subject with a disease or condition treatable by administration of a derivative, analog, or prodrug of eflornithine, the dosage of the derivative, analog, or prodrug of eflornithine is from about 1 $g/m^2$ to about 5 $g/m^2$.

In one alternative, the dosage of eflornithine or of a derivative, analog, or prodrug of eflornithine in a composition according to the present invention is sufficient to treat anaplastic astrocytoma or a similar malignancy. The dosage of the eflornithine or the derivative, analog, or prodrug of eflornithine in a composition according to the present invention can be adjusted to personalize the dosage as required, taking into account one or more factors selected from the group consisting of the stage of the disease, the severity of the disease, the tissue or organ affected by the disease, the existence or non-existence of metastases, the weight of the subject, the age of the subject, the existence or non-existence of other pathological conditions in the subject, including any conditions that may interfere with treatment or induce side effects if eflornithine or a derivative, analog, or prodrug of eflornithine is administered, the route of administration, and pharmacokinetic considerations such as liver and kidney function.

Typically, the administration of a composition according to the present invention to a subject with a disease or condition treatable by administration of a derivative, analog, or prodrug of eflornithine overcomes the blood-brain barrier by creating a plasma concentration gradient sufficient to overcome the blood-brain barrier.

Pharmaceutical compositions according to the present invention can be prepared in a number of physical forms. The physical form of the composition can be selected by one of ordinary skill in the art for administration and depends on the quantity of eflornithine or a derivative, analog, or prodrug of eflornithine, the presence or absence and, if present, the quantity of other therapeutically effective components, the excipient or excipients used, and the route of administration. Suitable physical forms include, but are not limited to, solutions, suspensions, gels, quick dissolve powders, quick dissolve tablets, capsules, tablets, multiple capsules, multiple tablets, chewables, bars, and other forms.

When a pharmaceutical composition according to the present invention is in the physical form of a capsule or tablet, the composition can include as an excipient a binding material, such as but not limited to, block polymers, natural and synthetic rubber, polyacrylates, polyurethanes, silicones, polysiloxanes and styrene-butadiene copolymers. The composition can also include as an excipient a plasticizer, such as, but not limited to, diethyl phthalate and glycerol. The composition can also include as an excipient a tablet or capsule diluent, such as, but not limited to, dibasic calcium phosphate, kaolin, lactose, mannitol, microcrystalline cellulose, powdered cellulose, precipitated calcium carbonate, sodium carbonate, sodium phosphate, sorbitol, and starch. The composition can also include as an excipient a tablet or capsule opaquant, such as, but not limited to, titanium dioxide.

When a pharmaceutical composition according to the present invention is in the physical form of a tablet, the composition can include as an excipient a tablet anti-adherent agent, such as, but not limited to, magnesium stearate and talc. The composition can also include as an excipient a tablet binder, such as, but not limited to, acacia, alginic acid, carboxymethylcellulose sodium, compressible sugar, ethylcellulose, gelatin, liquid glucose, methylcellulose, non-crosslinked polyvinyl pyrrolidone, and pregelatinized starch. The composition can also include as an excipient a tablet coating agent such as, but not limited to, liquid glucose, hydroxyethyl cellulose, hydroxypropyl cellulose, hydroxypropyl methylcellulose, methylcellulose, ethylcellulose, cellulose acetate phthalate and shellac. The composition can also include as an excipient a tablet direct compression excipient such as, but not limited to, dibasic calcium phosphate. The composition can also include as an excipient a tablet disintegrant such as, but not limited to, alginic acid, carboxymethylcellulose calcium, microcrystalline cellulose, polacrilin potassium, cross-linked polyvinylpyrrolidone, sodium alginate, sodium starch glycolate, and starch. The composition can also include as an excipient a tablet glidant such as, but not limited to, colloidal silica, corn starch, and talc. The composition can also include as an excipient a tablet lubricant such as, but not limited to, calcium stearate, magnesium stearate, mineral oil, stearic acid, and zinc stearate. The composition can also include as an excipient a tablet polishing agent such as, but not limited to, carnauba wax and white wax.

In another embodiment of the present invention, the pharmaceutical composition can be in the physical form of a rapidly dissolving tablet. Rapidly dissolving tablets are disclosed in U.S. Pat. No. 9,273,040 to Layton et al., U.S. Pat. No. 9,220,747 to Nilsson et al., U.S. Pat. No. 9,192,580 to Green et al., U.S. Pat. No. 8,545,989 to Norman et al., U.S. Pat. No. 7,815,937 to Mezaache et al., U.S. Pat. No. 6,221,392 to Khankari et al., U.S. Pat. No. 6,024,981 to Khankari et al., U.S. Pat. No. 5,807,578 to Acosta-Cuello et al., U.S. Pat. No. 5,807,577 to Ouali, U.S. Pat. No. 5,807,576 to Allen. Jr. et al., U.S. Pat. No. 5,776,491 to Allen, Jr. et al., U.S. Pat. No. 5,709,886 to Bettman et al., U.S. Pat. No. 5,639,475 to Bettman et al., U.S. Pat. No. 5,635,210 to Allen, Jr. et al., U.S. Pat. No. 5,607,697 to Alkire et al., U.S. Pat. No. 5,595,761 to Allen, Jr. et al., U.S. Pat. No. 5,587,180 to Allen, Jr., et al., U.S. Pat. No. 5,503,846 to Wehling et al., U.S. Pat. No. 5,466,464 to Masaki et al., U.S. Pat. No. 5,401,513 to Wehling et al., U.S. Pat. No. 5,223,264 to Wehling et al., U.S. Pat. No. 5,219,574 to Wehling et al., and U.S. Pat. No. 5,178,878 to Wehling et al. Such formulations can include, for example, intrabuccally disintegrating solid formulations or preparations which comprise the active ingredient, a sugar comprising lactose and/or mannitol and 0.12% (w/w) to 1.2% (w/w), based on the solid components, of agar and which has a density of 400 mg/mL to 1,000 mg/mL and have a sufficient strength for handling, which in practice may mean sufficient strength to withstand removal from a blister packaging without disintegrating. In one alternative, these dosage forms are hard, compressed, rapidly dissolvable dosage forms adapted for direct oral dosing comprising an active ingredient and a matrix including a non-direct compression filter and a lubricant, where the dosage form is adapted to rapidly dissolve in the mouth of a patient and thereby liberate the active ingredient, and having a friability of about 2% or less when tested according to the U.S.P., the dosage form optionally having a hardness of at least about 15 Newtons (N), preferably from 15-50 N. Typically, such dosage forms dissolve in about 90 seconds or less (preferably 60 seconds or less and most preferably 45 seconds or less) in the patient's mouth. Such formulations can also include particles made of an active ingredient, such as eflornithine or a derivative, analog, or prodrug thereof, and a protective material in which the particles are incorporated. Typically, these particles are provided in an amount of between about 0.01 and about 75% by weight based on the weight of the tablet. The tablet also includes a matrix made from a non-direct compression filler, a wicking agent, and a hydrophobic lubricant. The tablet matrix comprises at least about 60% rapidly water soluble ingredients based on the total weight of the matrix material. The tablet has a hardness of between about 15 and about 50 Newtons, a friability of less than 2% when measured by U.S.P. and is adapted to dissolve spontaneously in the mouth of a patient in less than about 60 seconds and thereby liberate the particles and be capable of being stored in bulk. A very fine grained or powdered sugar known as a non-direct compression sugar may be used as a filler in the matrix of this embodiment of the present invention. This material, in part because of its chemical composition and in part because of its fine particle size, will dissolve readily in the mouth in a matter of seconds once it is wetted by saliva. Not only does this mean that it can contribute to the speed at which the dosage form will dissolve, it also means that while the patient is holding the dissolving dosage form in his or her mouth, the filler will not contribute a "gritty" or "sandy" texture thus adversely affecting the organoleptic sensation of taking the dosage form. In contrast, direct compression versions of the same sugar are usually granulated and treated to make them larger and better for compaction. While these sugars are water soluble, they may not be solubilized quickly enough. As a result, they can contribute to the gritty or sandy texture of the dosage form as it dissolves. Dissolution time in the mouth can be measured by observing the dissolution time of the tablet in water at about 37° C. The tablet is immersed in the water without forcible agitation or with minimal agitation. The dissolution time is the time from immersion to substantially complete dissolution of the rapidly water soluble ingredients of the tablet as determined by visual observation. Particularly preferred fillers, in accordance with the present invention are non-direct compression sugars and sugar alcohols which meet the specifications discussed above. Such sugars and sugar alcohols include, without limitation, dextrose, mannitol, sorbitol, lactose and sucrose. Of course, dextrose, for example, can exist as either a direct compression sugar, i.e., a sugar which has been modified to increase its compressibility, or a non-direct compression sugar. Generally, the balance of the formulation can be matrix. Thus the percentage of filler can approach 100%. However, generally, the amount of non-direct compression filler useful in accordance with the present invention ranges from about 25 to about 95%, preferably between about 50 and about 95% and more preferably from about 60 to about 95%. The amount of lubricant used can generally range from between about 1 to about 2.5% by weight, and more preferably between about 1.5 to about 2% by weight. Hydrophobic lubricants useful in accordance with the present invention include alkaline stearates, stearic acid, mineral and vegetable oils, glyceryl behenate and sodium stearyl fumarate. Hydrophilic lubricants can also be used. Protective materials useful in accordance with this embodiment of the present invention may include any of the polymers conventionally utilized in the formation of microparticles, matrix-type microparticles and microcapsules. Among these are cellulosic materials such as naturally occurring cellulose and synthetic cellulose derivatives, acrylic polymers and vinyl polymers. Other simple polymers include proteinaceous materials such as gelatin, polypeptides and natural and synthetic shellacs and waxes. Protective polymers may also include ethylcellulose, methylcellulose, carboxymethyl cellulose and acrylic resin material sold under the registered trade mark EUDRAGIT® by Rhone Pharma GmbH of Weiterstadt, Germany. In addition to the ingredients previously discussed, the matrix may also include wicking agents, non-effervescent disintegrants and effervescent disintegrants. Wicking agents are compositions which are capable of drawing water up into the dosage form. They help transport moisture into the interior of the dosage form. In that way the dosage form can dissolve from the inside, as well as from the outside. Any chemical which can function to transport moisture as discussed above can be considered a wicking agent. Wicking agents include a number of traditional non-effervescent disintegration agents. These include, for example, microcrystalline cellulose (AVICEL PH 200, AVICEL PH 101), Ac-Di-Sol (Croscarmelose Sodium) and PVP-XL (a crosslinked polyvinylpyrrolidone); starches and modified starches, polymers, and gum such as arabic and xanthan. Hydroxyalkyl cellulose such as hydroxymethylcellulose, hydroxypropylcellulose and hydroxyopropylmethylcellulose, as well as compounds such as carbopol may be used as well. The conventional range of non-effervescent disintegrant agents used in conventional tablets can be as high as 20%. However, generally, the amount of disintegration agent used ranges from between about 2 and about 5%. Typically, the amount of wicking agents used may range from between 2 to about 12% and preferably from between 2 to about 5%. Other ingredients, such as non-effervescent disintegrants or an effervescent couple, can be included; preferred effervescent couples evolve gas by means of a chemical reaction which takes place upon exposure of the effervescent disintegration couple to water and/or to saliva in the mouth, and typically evolve gas by the reaction of a solid acid source and an alkali monohydrogen carbonate or other carbonate source. The acid sources can include, but are not limited to, citric acid, tartaric acid, malic acid, fumaric acid, adipic acid, and succinic acid. Carbonate sources include dry solid carbonate and carbonate or bicarbonate salts such as sodium bicarbonate, sodium carbonate, potassium bicarbonate, or potassium carbonate. In another alternative, a rapidly dissolving tablet can comprise one of the following alternatives (the proportions are for the non-therapeutically-active components): (i) 65-92% by weight of a polyol or mixture of polyols; 2-8% by weight of a cross-linked polyvinylpyrrolidone; 2-6% by weight of sodium croscarmellose; 3-12% by weight of starch; 0.05-0.5% by weight silica gel; and 0.05-0.5% by weight of colloidal silica; (ii) 75-90% by weight of a polyol or mixture of polyols; 3-7% by weight of a cross-linked polyvinyl pyrrolidone; 1-4% by weight of sodium croscarmellose; 4-10% by weight of starch; 0.05-0.3% by weight silica gel; and 0.05-0.3% by weight colloidal silica; (iii) 80-88% by weight of a polyol or mixture of polyols; 3.5-6% by weight of a cross-linked polyvinyl pyrrolidone; 2.5-3.5% by weight of sodium croscarmellose; 5-9% by weight of starch; 0.05-0.25% by weight silica gel; and 0.05-0.25% by weight of colloidal silica; and (iv) 84-85% by weight of a polyol or mixture of polyols; 4-5% by weight of a cross-linked polyvinyl pyrrolidone; 2.9-3.2% by weight of sodium croscarmellose; 7-8% by weight of starch; 0.15-0.20% by weight silica gel; and 0.15-0.20% by weight of colloidal silica. Suitable polyols for these alternatives include sorbitol, mannitol, maltitol, erythritol, xylitol, lactitol, and mixtures thereof. Suitable disintegrating agents include crospovidone, sodium starch glycolate, sodium croscarmellose, and mixtures thereof. Other excipients such as glidants can be included, as can coloring agents, lubricants, citric acid, ascorbic acid, and sweetening agents.

In some alternatives according to the present invention for rapidly dissolving tablets, the dosage form can include a superdisintegrant. Superdisintegrants include, but are not limited to, crospovidone, sodium croscarmellose, and sodium starch glycolate. A superdisintegrant is a disintegrant that has an Eq. Moisture content at 25° C. and 90% relative humidity of over 50%.

In some alternatives according to the present invention, the dosage form can include a high molecular weight polyethylene glycol or a polyethylene glycol glyceryl ester, such as those described in U.S. Pat. No. 7,815,937. The high molecular weight polyethylene glycol and the polyethylene glycol glyceryl ester can be incorporated into microspheres. Either the microspheres or the therapeutically active agent or agents can be coated or encapsulated with at least one coating, such as methacrylate/cellulose polymers, acrylate/cellulose polymers, ethylcellulose, hydroxypropylcellulose, hydroxypropylmethylcellulose, hydroxypropylmethylcellulose phthalate, cellulose acetate phthalate, Eudragit NE 300, Eudragit RS, or Eudragit L 30 D.

In some alternatives according to the present invention for rapidly dissolving tablets, the dosage form can include a pharmaceutically acceptable starch, a starch degrading enzyme, and a tablet lubricant.

In some alternatives according to the present invention for rapidly dissolving tablets, the dosage form can include a first polypeptide component and a second polypeptide component, wherein the first polypeptide component and the second polypeptide component have the same net charge in solution (i.e., either a negative charge or a positive charge). The first polypeptide component can comprise a non-hydrolyzed gelatin and the second polypeptide can comprise a hydrolyzed gelatin. The composition can further comprise a bulking agent.

In some alternatives according to the present invention for rapidly dissolving tablets, the dosage form includes a microencapsulated mixture of sodium bicarbonate and citric acid. The microencapsulation can be by ethylcellulose.

In some alternatives according to the present invention for rapidly dissolving tablets, the dosage form includes a sugar selected from the group consisting of lactose and mannitol and agar.

In some alternatives according to the present invention for rapidly dissolving tablets, the dosage form includes particulate magnesium carbonate and an oil absorbed thereon. The oil can be white mineral oil, soybean oil, or another vegetable oil; the oil can also include flavoring.

In another embodiment of the present invention, the pharmaceutical composition can be in the physical form of a rapidly dissolving powder. Rapidly dissolving powders are disclosed in U.S. Pat. No. 6,197,817 to Matier et al.

In some alternatives according to the present invention for rapidly dissolving powders, the dosage form includes lactose monohydrate, crospovidone, sodium bicarbonate, and magnesium stearate; sweetening agents and flavors may also be added.

In another embodiment of the present invention, the pharmaceutical composition can be in the physical form of a suspension for oral administration. Suspensions for oral administration are disclosed in U.S. Pat. No. 9,309,285 to Roberts et al., U.S. Pat. No. 9,290,491 to Dalziel et al., U.S. Pat. No. 9,284,279 to Ford et al., U.S. Pat. No. 9,283,183 to Mammen et al., and U.S. Pat. No. 9,273,005 to Mercurio et al.

In some alternatives according to the present invention for suspensions for oral administration, the dosage form includes suspending agents such as, for example, ethoxylated isostearyl alcohols, polyoxyethylene sorbitol and sorbitan esters, microcrystalline cellulose, aluminum metahydroxide, bentonite, agar-agar and tragacanth.

In some alternatives according to the present invention for suspensions for oral administration, the dosage form includes natural or synthetic gums, resins, methylcellulose, sodium carboxymethylcellulose, or another suspending agent.

In some alternatives according to the present invention for suspensions for oral administration, the dosage form includes fumaric acid, sodium chloride, methylparaben, propylparaben, granulated sugar, sorbitol, Veegum, flavoring, and coloring.

In some alternatives according to the present invention for suspensions for oral administration, the dosage form includes glycerol, sorbitol, sodium saccharin, xanthan gum, flavoring, citric acid, sodium citrate, methylparaben, and potassium sorbate.

In another embodiment of the present invention, the pharmaceutical composition can be in the physical form of a gel for oral administration. In general, a pharmaceutical composition that is in the form of a gel is liquid and includes one or more gel-forming agents.

In some alternatives according to the present invention for gels for oral administration, the gel-forming agent is selected from the group consisting of polyethylene glycol, polyacrylic acid, polyethylene oxide, polyvinyl alcohol, hydroxypropyl methyl cellulose, methylcellulose, hydroxyethyl cellulose, carboxymethyl cellulose, polyvinyl alcohol, polyvinylpyrrolidone, carbopol, gum Arabic, gum tragacanth, alginate, carrageenate, agar, gelatin, carbomers, and combinations thereof. Other gel-forming agents are known in the art and are described in V. G. Kadajji & G. V. Betageri, "Water Soluble Polymers for Pharmaceutical Applications," *Polymers* 3: 1972-2009 (2011, and include polyacrylamide, poly-N-(2-hydroxypropyl)methacrylamide, divinyl ether-maleic anhydride copolymers, polyoxazoline, polyphosphoesters, polyphosphazenes, xanthan gum, pectin, chitosan derivatives, dextran, guar gum, hyaluronic acid, albumin, starch and derivatives of starch, and combinations thereof.

Other excipients as described above that are compatible with a physical form of a gel for oral administration can be included in the gel.

In another embodiment of the present invention, the pharmaceutical composition can be in the form of a chewable solid. The chewable solid can be a chewable tablet, as described in U.S. Pat. No. 9,320,741 to Bradner et al.; a chewable lozenge as described in U.S. Pat. No. 9,304,134 to Smith; a chewable gum as described in U.S. Pat. No. 9,278,091 to Johnson et al.; or a chewable bar as described in U.S. Pat. No. 9,302,017 to Sancilio et al. Other chewable dosage forms are known in the art.

In one alternative, the pharmaceutical composition is in the physical form of a solution for oral administration and the composition comprises:
(1) from about 13.5% to about 22.5% of eflornithine HCl $H_2O$;
(2) from about 0.1125% to about 0.1875% of sodium benzoate;
(3) from about 0.1125% to about 0.1875% of saccharin sodium dihydrate;
(4) from about 2.25% to about 3.75% of glycerol;
(5) from about 3.75% to about 6.25% of propylene glycol; and
(6) purified water to 100%.

Typically, the pharmaceutical composition comprises:
(1) from about 16.2% to about 19.8% of eflornithine HCl $H_2O$;
(2) from about 0.135% to about 0.165% of sodium benzoate;
(3) from about 0.135% to about 0.165% of saccharin sodium dihydrate;
(4) from about 2.7% to about 3.3% of glycerol;
(5) from about 4.5% to about 5.5% of propylene glycol; and
(6) purified water to 100%.

Preferably, the pharmaceutical composition comprises:
(1) about 18.0% of eflornithine HCl $H_2O$;
(2) about 0.15% of sodium benzoate;
(3) about 0.15% of saccharin sodium dihydrate;
(4) about 3.0% of glycerol;
(5) about 5.0% of propylene glycol; and
(6) purified water to 100%.

In another alternative, the pharmaceutical composition is in the physical form of a rapidly dissolving powder and the composition comprises:
(1) from about 37.5% to about 62.5% of eflornithine HCl $H_2O$;
(2) from about 0.75% to about 1.25% of saccharin sodium dihydrate;
(3) from about 22.5% to about 37.5% of mannitol;
(4) from about 7.5% to about 12.5% of croscarmellose sodium; and
(5) from about 6.75% to about 11.25% of sodium starch glycolate.

Typically, the composition comprises:
(1) from about 45% to about 55% of eflornithine HCl $H_2O$;
(2) from about 0.9% to about 1.1% of saccharin sodium dihydrate;
(3) from about 27% to about 33% of mannitol;
(4) from about 9.0% to about 11.0% of croscarmellose sodium; and
(5) from about 8.1% to about 9.9% of sodium starch glycolate.

Preferably, the composition comprises:
(a) about 50% of eflornithine HCl $H_2O$;
(b) about 1.0% of saccharin sodium dihydrate;
(c) about 30% of mannitol;
(d) about 10% of croscarmellose sodium; and
(e) about 9% of sodium starch glycolate.

In yet another alternative, the pharmaceutical composition is in the physical form of a rapidly dissolving powder and the composition comprises:
(1) from about 37.5% to about 62.5% of eflornithine HCl $H_2O$;
(2) from about 0.75% to about 1.25% of saccharin sodium dihydrate;
(3) from about 26.25% to about 43.75% of mannitol;
(4) from about 5.25% to about 8.75% of sodium starch glycolate; and
(5) from about 5.25% to about 8.75% of camphor.

Typically, the composition comprises:
(1) from about 45% to about 55% of eflornithine HCl $H_2O$;
(2) from about 0.9% to about 1.1% of saccharin sodium dihydrate;
(3) from about 31.5% to about 38.5% of mannitol;
(4) from about 6.3% to about 7.7% of sodium starch glycolate; and
(5) from about 6.3% to about 7.7% of camphor.

Preferably, the composition comprises:
(1) about 50% of eflornithine HCl $H_2O$;
(2) about 1.0% of saccharin sodium dihydrate;
(3) about 35% of mannitol;
(4) about 7.0% of sodium starch glycolate; and
(5) about 7.0% of camphor.

In yet another alternative, the pharmaceutical composition is in the physical form of a rapidly dissolving powder and the composition comprises:
(1) from about 37.5% to about 62.5% of eflornithine HCl $H_2O$;
(2) from about 0.75% to about 1.25% of saccharin sodium dihydrate;
(3) from about 26.25% to about 43.75% of mannitol;

(4) from about 5.25% to about 8.75% of croscarmellose sodium; and
(5) from about 5.25% to about 8.75% of camphor.
Typically, the composition comprises:
(1) from about 45% to about 55% of eflornithine HCl H$_2$O;
(2) from about 0.9% to about 1.1% of saccharin sodium dihydrate;
(3) from about 31.5% to about 38.5% of mannitol;
(4) from about 6.3% to about 7.7% of croscarmellose sodium; and
(5) from about 6.3% to about 7.7% of camphor.
Preferably, the composition comprises:
(1) about 50% of eflornithine HCl H$_2$O;
(2) about 1.0% of saccharin sodium dihydrate;
(3) about 35% of mannitol;
(4) about 7.0% of croscarmellose sodium; and
(5) about 7.0% of camphor.
In yet another alternative, the pharmaceutical composition is in the physical form of a suspension and the composition comprises:
(1) from about 37.5% to about 62.5% of eflornithine HCl H$_2$O;
(2) from about 7.5% to about 12.5% of glycerol;
(3) from about 0.15% to about 0.25% of saccharin sodium dihydrate;
(4) from about 0.15% to about 0.25% of sodium benzoate; and
(5) water to 100%.
Typically, the composition comprises:
(1) from about 45% to about 55% of eflornithine HCl H$_2$O;
(2) from about 9.0% to about 11.0% of glycerol;
(3) from about 0.18% to about 0.22% of saccharin sodium dihydrate;
(4) from about 0.18% to about 0.22% of sodium benzoate; and
(5) water to 100%.
Preferably, the composition comprises:
(1) about 50% of eflornithine HCl H$_2$O;
(2) about 10% of glycerol;
(3) about 0.2% of saccharin sodium dihydrate;
(4) about 0.2% of sodium benzoate; and
(5) about 40% of water.
In yet another alternative, the pharmaceutical composition is in the physical form of a suspension and the composition comprises:
(1) from about 37.5% to about 62.5% of eflornithine HCl H$_2$O;
(2) from about 7.5% to about 12.5% of glycerol;
(3) from about 0.15% to about 0.25% of saccharin sodium dihydrate;
(4) from about 11.25% to about 18.75% of sorbitol;
(5) from about 0.15% to about 0.25% of sodium benzoate; and
(6) water to 100%.
Typically, the composition comprises:
(1) from about 45% to about 55% of eflornithine HCl H$_2$O;
(2) from about 9.0% to about 11.0% of glycerol;
(3) from about 0.18% to about 0.22% of saccharin sodium dihydrate;
(4) from about 13.5% to about 16.5% of sorbitol;
(5) from about 0.18% to about 0.22% of sodium benzoate; and
(6) water to 100%.

Preferably, the composition comprises:
(a) about 50% of eflornithine HCl H$_2$O;
(b) about 10% of glycerol;
(c) about 0.2% of saccharin sodium dihydrate;
(d) about 0.2% of sodium benzoate; and
(e) about 40% of water.
In yet another alternative, the pharmaceutical composition is in the physical form of a suspension and the composition comprises:
(1) from about 37.5% to about 62.5% of eflornithine HCl H$_2$O;
(2) from about 7.5% to about 12.5% of glycerol;
(3) from about 0.15% to about 0.25% of saccharin sodium dihydrate;
(4) from about 11.25% to about 18.75% of sorbitol;
(5) from about 0.15% to about 0.25% of sodium benzoate; and
(6) water to 100%.
Typically, the composition comprises:
(1) from about 45% to about 55% of eflornithine HCl H$_2$O;
(2) from about 9.0% to about 11.0% of glycerol;
(3) from about 0.18% to about 0.22% of saccharin sodium dihydrate;
(4) from about 13.5% to about 16.5% of sorbitol;
(5) from about 0.18% to about 0.22% of sodium benzoate; and
(6) water to 100%.
Preferably, the composition comprises:
(1) about 50% of eflornithine HCl H$_2$O;
(2) about 10% of glycerol;
(3) about 0.2% of saccharin sodium dihydrate;
(4) about 15% of sorbitol;
(5) about 0.2% of sodium benzoate; and
(6) about 25% of water.
In yet another alternative, the pharmaceutical composition is in the physical form of a suspension and the composition comprises:
(1) from about 15% to about 25% of eflornithine HCl H$_2$O;
(2) from about 0.1125% to about 0.1875% of sodium benzoate;
(3) from about 0.1125% to about 0.1875% of saccharin sodium dihydrate;
(4) from about 4.5% to about 7.5% of glycerol;
(5) from about 7.5% to about 12.5% of propylene glycol; and
(6) water to 100%.
Typically, the composition comprises:
(1) from about 18% to about 22% of eflornithine HCl H$_2$O;
(2) from about 0.135% to about 0.165% of sodium benzoate;
(3) from about 0.135% to about 0.165% of saccharin sodium dihydrate;
(4) from about 5.4% to about 6.6% of glycerol;
(5) from about 9.0% to about 11.0% of propylene glycol; and
(6) water to 100%.
Preferably, the composition comprises:
(1) about 20% of eflornithine HCl H$_2$O;
(2) about 0.15% of sodium benzoate;
(3) about 0.15% of saccharin sodium dihydrate;
(4) about 6.0% of glycerol;
(5) about 10.0% of propylene glycol; and
(6) about 63.7% of water.

In yet another alternative, the pharmaceutical composition is in the physical form of a suspension and the composition comprises:
(1) from about 13.5% to about 22.5% of eflornithine HCl H₂O;
(2) from about 0.1125% to about 0.1875% of sodium benzoate;
(3) from about 0.1125% to about 0.1875% of saccharin sodium dihydrate;
(4) from about 2.25% to about 3.75% of glycerol;
(5) from about 3.75% to about 6.25% of propylene glycol; and
(6) water to 100%.

Typically, the composition comprises:
(a) from about 16.2% to about 19.8% of eflornithine HCl H₂O;
(b) from about 0.135% to about 0.165% of sodium benzoate;
(c) from about 0.135% to about 0.165% of saccharin sodium dihydrate;
(d) from about 2.7% to about 3.3% of glycerol;
(e) from about 4.5% to about 5.5% of propylene glycol; and
(f) water to 100%.

Preferably, the composition comprises:
(1) about 18% of eflornithine HCl H₂O;
(2) about 0.15% of sodium benzoate;
(3) about 0.15% of saccharin sodium dihydrate;
(4) about 3.0% of glycerol;
(5) about 5.0% of propylene glycol; and
(6) about 73.70% of water.

In compositions according to the present invention for which the components are described above, substitutions that would be acceptable to one of ordinary skill in the art can be made and such compositions in which such acceptable substitutions are made are also within the scope of the invention. For example, in general, a derivative, analog, or prodrug of eflornithine having inhibitory activity against ornithine decarboxylase can generally replace eflornithine in these compositions. Similarly, particles of other sugar alcohols of an appropriate size range can replace mannitol in compositions according to the present invention. Other substitutions can be determined based on the physical and chemical properties of the component to be substituted and the proposed alternative component.

Another aspect of the present invention is a kit that comprises two or more dosage forms of pharmaceutical compositions according to the present invention. Typically, the dosage forms of the pharmaceutical compositions are in a solid form as described above. The kit can comprise instructions for use of the pharmaceutical compositions. The dosage forms of the pharmaceutical compositions can be the same or different. In one alternative, the dosage forms of the pharmaceutical compositions are the same and include the same dosage of the eflornithine or the derivative, analog, or prodrug of eflornithine. In another alternative, the dosage forms of the pharmaceutical compositions are different and include different dosages of the eflornithine or the derivative, analog, or prodrug of eflornithine. Various arrangements are possible; for example, and not by way of limitation, the kit can comprise a total of 10 dosage forms of the pharmaceutical compositions, two each of five different dosages of the eflornithine or the derivative, analog, or prodrug of eflornithine. In yet another alternative, the kit can include dosage forms of pharmaceutical compositions that include different therapeutic agents. For example, the kit can include: (i) dosage forms of eflornithine or a derivative, analog, or prodrug of eflornithine; and (ii) dosage forms of another therapeutic agent, such as a therapeutic agent for treating a malignancy such as glioma or a therapeutic agent, such as those described above or a conventional agent for the treatment of the malignancy, or an agent for improving the efficacy of the eflornithine or the derivative, analog or prodrug as described above.

In one alternative, the kit comprises two or more dosage forms wherein each dosage form comprises:
(1) a therapeutically effective quantity of eflornithine or a derivative, analog, or prodrug of eflornithine; and
(2) an additional component selected from the group consisting of:
(a) at least one additional therapeutic agent that is compatible with the eflornithine or the derivative, analog, or prodrug thereof;
(b) an inhibitor of polyamine transport or polyamine synthesis;
(c) an S-adenosylmethionine decarboxylase inhibitor;
(d) an agent selected from the group consisting of:
(i) a retinoid;
(ii) a syrbactin compound;
(iii) a cyclooxygenase-2 inhibitor;
(iv) a non-steroidal anti-inflammatory agent;
(v) castanospermine or castanospermine esters;
(vi) an aziridinyl putrescine compound;
(vii) an interferon;
(viii) an aryl substituted xylopyranoside derivative;
(ix) an agent that reduces blood glutamate levels and enhances brain to blood glutamate efflux;
(x) chitosan or chitosan derivatives and analogs;
(xi) 2,4-disulfonyl phenyl tert-butyl nitrone;
(xii) 3-(4-amino-1-oxo-1,3-dihydro-isoindol-2-yl)-piperidine-2,6-dione;
(xiii) thalidomide;
(xiv) N-2-pyridinyl-2-pyridinecarbothioamide;
(xv) cambendazole; and
(xvi) an inhibitor of histone demethylase;
(e) an agent that increases the ability of the eflornithine or derivative, analog, or prodrug thereof to pass through the blood-brain barrier;
(f) an immunomodulator; and
(g) an EGFR inhibitor.

In another alternative, the kit comprises:
(1) at least one dosage form comprising eflornithine or derivative, analog, or prodrug thereof; and
(2) at least one dosage form comprising:
(A) at least one additional therapeutic agent that is compatible with the eflornithine or the derivative, analog, or prodrug thereof;
(B) an inhibitor of polyamine transport or polyamine synthesis;
(C) an S-adenosylmethionine decarboxylase inhibitor;
(D) an agent selected from the group consisting of:
(i) a retinoid;
(ii) a syrbactin compound;
(iii) a cyclooxygenase-2 inhibitor;
(iv) a non-steroidal anti-inflammatory agent;
(v) castanospermine or castanospermine esters;
(vi) an aziridinyl putrescine compound;
(vii) an interferon;
(viii) an aryl substituted xylopyranoside derivative;
(ix) an agent that reduces blood glutamate levels and enhances brain to blood glutamate efflux;
(x) chitosan or chitosan derivatives and analogs;
(xi) 2,4-disulfonyl phenyl tert-butyl nitrone;

(xii) 3-(4-amino-1-oxo-1,3-dihydro-isoindol-2-yl)-piperidine-2,6-dione;
(xiii) thalidomide;
(xiv) N-2-pyridinyl-2-pyridinecarbothioamide;
(xv) cambendazole; and
(xvi) an inhibitor of histone demethylase;
(E) an agent that increases the ability of the eflornithine or derivative, analog, or prodrug thereof to pass through the blood-brain barrier;
(F) an immunomodulator; and
(G) an EGFR inhibitor.

Other arrangements of dosage forms are possible in a kit according to the present invention.

When different solid dosage forms are included in a kit, the solid dosage forms can be distinguished by color, by shape or by other markings. The dosage forms of the kit can be incorporated in a conventional holder for multiple dosage forms such as a blister pack usable by a subject who can self-administer the dosage forms at appropriate times as prescribed.

Kits according to the present invention can further include, separately packaged, instructions for dosage administration or use of the dosage forms included in the kit.

Dosage forms according to the present invention can be used together with dispensing or dosing devices as are generally known in the art. When the dosage forms are solid forms, such as powders, dispensing devices that are metering devices are known in the art, and are described in U.S. Pat. No. 9,278,975 to Sangi; U.S. Pat. No. 8,980,878 to Siegel et al.; U.S. Pat. No. 8,673,366 to Batarseh; U.S. Pat. No. 4,601,897 to Saxton; and U.S. Pat. No. 4,195,023 to Mulvey et al. The metering device can be adapted to dispense the desired quantity of the solid dosage form. Other metering devices are known in the art. Typically, a dispensing device is preloaded with the dosage form so that the dosage form is ready to be administered to a subject in need thereof. A kit can be constructed comprising a dispensing device preloaded with a dosage form and instructions for use of the dispensing device and administration of the dosage form.

When the dosage forms are liquid or substantially liquid dosage forms such as a solution, a gel, or a suspension, the dispensing device can be a dosage cup, a pump, or another device known in the art. Dosage cups are described in U.S. Pat. No. 9,284,543 to Wei et al. and U.S. Pat. No. 8,518,439 to Puttachari et al. Pumps are described in U.S. Pat. No. 9,322,018 to Bettencourt et al.; U.S. Pat. No. 9,321,797 to Sauve et al.; and U.S. Pat. No. 9,321,781 to Lavoie et al. The dosage cup or pump can be adapted to dispense the desired quantity of the solid dosage form. Other dispensing devices for liquid or substantially liquid dosage forms are known in the art. Particularly when the dispensing device is a pump, a dispensing device can be preloaded with the dosage form so that the dosage form is ready to be administered to a subject in need thereof. A kit can be constructed with a dispensing device and instructions for use of the dispensing device and administration of the dosage form. Particularly when the dispensing device is a pump, the dispensing device in the kit can be preloaded with the dosage form.

The compounds described above, including eflornithine or derivatives, analogs, or prodrug thereof, as well as the additional therapeutically active agents or agents that improve the efficacy or delivery of the eflornithine or the derivatives, analogs, or prodrugs thereof, that may be incorporated into a pharmaceutically composition according to the present invention, can optionally be further substituted. In general, for optional substituents at saturated carbon atoms such as those that are part of the structures of the compounds described above, the following substituents can be employed: $C_6$-$C_{10}$ aryl, heteroaryl containing 1-4 heteroatoms selected from N, O, and S, $C_1$-$C_{10}$ alkyl, $C_1$-$C_{10}$ alkoxy, cycloalkyl, F, amino ($NR^1R^2$), nitro, —SR, —S(O)R, —S($O_2$)R, —S($O_2$)$NR^1R^2$, and —$CONR^1R^2$, which can in turn be optionally substituted. Further descriptions of potential optional substituents are provided below.

Optional substituents as described above that are within the scope of the present invention do not substantially affect the activity of the derivative or the stability of the derivative, particularly the stability of the derivative in aqueous solution. This applies to both derivatives, analogs, or prodrugs of eflornithine and derivatives, analogs, or prodrugs of an additional therapeutically active agent that can be incorporated into a composition. Definitions for a number of common groups that can be used as optional substituents are provided below; however, the omission of any group from these definitions cannot be taken to mean that such a group cannot be used as an optional substituent as long as the chemical and pharmacological requirements for an optional substituent are satisfied. The introduction of an optional substituent in a component of a pharmaceutical composition according to the present invention does not interfere with the activity of the eflornithine or derivative, analog, or prodrug thereof that is included in the pharmaceutical composition or with the activity of any additional therapeutically active agent included in the pharmaceutical composition.

As used herein, the term "alkyl" refers to an unbranched, branched, or cyclic saturated hydrocarbyl residue, or a combination thereof, of from 1 to 12 carbon atoms that can be optionally substituted; the alkyl residues contain only C and H when unsubstituted. Typically, the unbranched or branched saturated hydrocarbyl residue is from 1 to 6 carbon atoms, which is referred to herein as "lower alkyl." When the alkyl residue is cyclic and includes a ring, it is understood that the hydrocarbyl residue includes at least three carbon atoms, which is the minimum number to form a ring. As used herein, the term "alkenyl" refers to an unbranched, branched or cyclic hydrocarbyl residue having one or more carbon-carbon double bonds. As used herein, the term "alkynyl" refers to an unbranched, branched, or cyclic hydrocarbyl residue having one or more carbon-carbon triple bonds; the residue can also include one or more double bonds. With respect to the use of "alkenyl" or "alkynyl," the presence of multiple double bonds cannot produce an aromatic ring. As used herein, the terms "hydroxyalkyl," "hydroxyalkenyl," and "hydroxyalkynyl," respectively, refer to an alkyl, alkenyl, or alkynyl group including one or more hydroxyl groups as substituents; as detailed below, further substituents can be optionally included. As used herein, the term "aryl" refers to a monocyclic or fused bicyclic moiety having the well-known characteristics of aromaticity; examples include phenyl, naphthyl, fluorenyl, and indenyl, which can be optionally substituted. As used herein, the term "hydroxyaryl" refers to an aryl group including one or more hydroxyl groups as substituents; as further detailed below, further substituents can be optionally included. As used herein, the term "heteroaryl" refers to monocyclic or fused bicyclic ring systems that have the characteristics of aromaticity and include one or more heteroatoms selected from O, S, and N. The inclusion of a heteroatom permits aromaticity in 5-membered rings as well as in 6-membered rings. Typical heteroaromatic systems include monocyclic $C_5$-$C_6$ heteroaromatic groups such as pyridyl, pyrimidyl, pyrazinyl, thienyl, furanyl, pyrrolyl, pyrazolyl, thiazolyl, oxazolyl, triazolyl, triazinyl, tetrazolyl, tetrazinyl, and imidazolyl, as well as the fused bicyclic moieties formed by fusing one of these monocyclic heteroaromatic groups with a phenyl ring or with any of the heteroaromatic monocyclic groups to form a $C_8$-$C_{10}$ bicyclic group such as indolyl, benzimidazolyl, indazolyl, benzotriazolyl, isoquinolyl, quinolyl, benzothiazolyl, benzofuranyl, pyrazolylpyridyl, quinazolinyl, quinoxalinyl, cinnolinyl, and other ring systems known in the art. Any monocyclic or fused ring bicyclic system that has the characteristics of aromaticity in terms of delocalized electron distribution throughout the ring system is included in this definition. This definition also includes bicyclic groups where at least the ring that is directly attached to the remainder of the molecule has the characteristics of aromaticity, including the delocalized electron distribution that is characteristic of aromaticity. Typically the ring systems contain 5 to 12 ring member atoms and up to four heteroatoms, wherein the heteroatoms are selected from the group consisting of N, O, and S. Frequently, the monocyclic heteroaryls contain 5 to 6 ring members and up to three heteroatoms selected from the group consisting of N, O, and S; frequently, the bicyclic heteroaryls contain 8 to 10 ring members and up to four heteroatoms selected from the group consisting of N, O, and S. The number and placement of heteroatoms in heteroaryl ring structures is in accordance with the well-known limitations of aromaticity and stability, where stability requires the heteroaromatic group to be stable enough to be exposed to water at physiological temperatures without rapid degradation. As used herein, the term "hydroxheteroaryl" refers to a heteroaryl group including one or more hydroxyl groups as substituents; as further detailed below, further substituents can be optionally included. As used herein, the terms "haloaryl" and "haloheteroaryl" refer to aryl and heteroaryl groups, respedively, substituted with at least one halo group, where "halo" refers to a halogen selected from the group consisting of fluorine, chlorine, bromine, and iodine, typically, the halogen is selected from the group consisting of chlorine, bromine, and iodine; as detailed below, further substituents can be optionally included. As used herein, the terms "haloalkyl," "haloalkenyl," and "haloalkynyl" refer to alkyl, alkenyl, and alkynyl groups, respectively, substituted with at least one halo group, where "halo" refers to a halogen selected from the group consisting of fluorine, chlorine, bromine, and iodine, typically, the halogen is selected from the group consisting of chlorine, bromine, and iodine; as detailed below, further substituents can be optionally included.

As used herein, the term "optionally substituted" indicates that the particular group or groups referred to as optionally substituted may have no non-hydrogen substituents, or the group or groups may have one or more non-hydrogen substituents consistent with the chemistry and pharmacological activity of the resulting molecule. If not otherwise specified, the total number of such substituents that may be present is equal to the total number of hydrogen atoms present on the unsubstituted form of the group being described; fewer than the maximum number of such substituents may be present. Where an optional substituent is attached via a double bond, such as a carbonyl oxygen (C=O), the group takes up two available valences on the carbon atom to which the optional substituent is attached, so the total number of substituents that may be included is reduced according to the number of available valences. As used herein, the term "substituted," whether used as part of "optionally substituted" or otherwise, when used to modify a specific group, moiety, or radical, means that one or more hydrogen atoms are, each, independently of each other, replaced with the same or different substituent or substituents.

Substituent groups useful for substituting saturated carbon atoms in the specified group, moiety, or radical include, but are not limited to, —$Z^a$, =O, —$OZ^b$, —$SZ^b$, =$S^-$, —$NZ^cZ^c$, =$NZ^b$, =N—$OZ^b$, trihalomethyl, —$CF_3$, —CN, —OCN, —SCN, —NO, —$NO_2$, =$N_2$, —$N_3$, —$S(O)_2Z^b$, —$S(O)_2NZ^b$, —$S(O_2)O^-$, —$S(O_2)OZ^b$, —$OS(O_2)OZ^b$, —$OS(O_2)O^-$, —$OS(O_2)OZ^b$, —$P(O)(O^-)_2$, —$P(O)(OZ^b)(O^-)$, —$P(O)(OZ^b)(OZ^b)$, —$C(O)Z^b$, —$C(S)Z^b$, —$C(NZ^b)Z^b$, —$C(O)O^-$, —$C(O)OZ^b$, —$C(S)OZ^b$, —$C(O)NZ^cZ^c$, —$C(NZ^b)NZ^cZ^c$, —$OC(O)Z^b$, —$OC(S)Z^b$, —$OC(O)O^-$, —$OC(O)OZ^b$, —$OC(S)OZ^b$, —$NZ^bC(O)Z^b$, —$NZ^bC(S)Z^b$, —$NZ^bC(O)O^-$, —$NZ^bC(O)OZ^b$, —$NZ^bC(S)OZ^b$, —$NZ^bC(O)NZ^cZ^c$, —$NZ^bC(NZ^b)Z^b$, —$NZ^bC(NZ^b)NZ^cZ^c$, wherein $Z^a$ is selected from the group consisting of alkyl, cycloalkyl, heteroalkyl, cycloheteroalkyl, aryl, arylalkyl, heteroaryl and heteroarylalkyl; each $Z^b$ is independently hydrogen or $Z^a$; and each $Z^c$ is independently $Z^b$ or, alternatively, the two $Z^c$'s may be taken together with the nitrogen atom to which they are bonded to form a 4-, 5-, 6-, or 7-membered cycloheteroalkyl ring structure which may optionally include from 1 to 4 of the same or different heteroatoms selected from the group consisting of N, O, and S. As specific examples, —$NZ^cZ^c$ is meant to include —$NH_2$, —NH-alkyl, —N-pyrrolidinyl, and —N-morpholinyl, but is not limited to those specific alternatives and includes other alternatives known in the art. Similarly, as another specific example, a substituted alkyl is meant to include -alkylene-O-alkyl, -alkylene-heteroaryl, -alkylene-cycloheteroaryl, -alkylene-C(O)$OZ^b$, -alkylene-C(O)$NZ^bZ^b$, and —$CH_2$—$CH_2$—C(O)—$CH_3$, but is not limited to those specific alternatives and includes other alternatives known in the art. The one or more substituent groups, together with the atoms to which they are bonded, may form a cyclic ring, including, but not limited to, cycloalkyl and cycloheteroalkyl.

Similarly, substituent groups useful for substituting unsaturated carbon atoms in the specified group, moiety, or radical include, but are not limited to, —$Z^a$, halo, —$O^-$, —$OZ^b$, —$SZ^b$, —$S^-$, —$NZ^cZ^c$, trihalomethyl, —$CF_3$, —CN, —OCN, —SCN, —NO, —$NO_2$, —$N_3$, —$S(O)_2Z^b$, —$S(O_2)O^-$, —$S(O_2)OZ^b$, —$OS(O_2)OZ^b$, —$OS(O_2)O^-$, —$P(O)(O^-)_2$, —$P(O)(OZ^b)(O^-)$, —$P(O)(OZ^b)(OZ^b)$, —$C(O)Z^b$, —$C(S)Z^b$, —$C(NZ^b)Z^b$, —$C(O)O^-$, —$C(O)OZ^b$, —$C(S)OZ^b$, —$C(O)NZ^cZ^c$, —$C(NZ^b)NZ^cZ^c$, —$OC(O)Z^b$, —$OC(S)Z^b$, —$OC(O)O^-$, —$OC(O)OZ^b$, —$OC(S)OZ^b$, —$NZ^bC(O)OZ^b$, —$NZ^bC(S)OZ^b$, —$NZ^bC(O)NZ^cZ^c$, —$NZ^bC(NZ^b)Z^b$, and —$NZ^bC(NZ^b)NZ^cZ^c$, wherein $Z^a$, $Z^b$, and $Z^c$ are as defined above.

Similarly, substituent groups useful for substituting nitrogen atoms in heteroalkyl and cycloheteroalkyl groups include, but are not limited to, —$Z^a$, halo, —$O^-$, —$OZ^b$, —$SZ^b$, —$S^-$, —$NZ^cZ^c$, trihalomethyl, —$CF_3$, —CN, —OCN, —SCN, —NO, —$NO_2$, —$S(O)_2Z^b$, —$S(O_2)O^-$, —$S(O_2)OZ^b$, —$OS(O_2)OZ^b$, —$OS(O_2)O^-$, —$P(O)(O^-)_2$, —$P(O)(OZ^b)(O^-)$, —$P(O)(OZ^b)(OZ^b)$, —$C(O)Z^b$, —$C(S)Z^b$, —$C(NZ^b)Z^b$, —$C(O)OZ^b$, —$C(S)OZ^b$, —$C(O)NZ^cZ^c$, —$C(NZ^b)NZ^cZ^c$, —$OC(O)Z^b$, —$OC(S)Z^b$, —$OC(O)OZ^b$, —$OC(S)OZ^b$, —$NZ^bC(O)Z^b$, —$NZ^bC(S)Z^b$, —$NZ^bC(O)OZ^b$, —$NZ^bC(S)OZ^b$, —$NZ^bC(O)NZ^cZ^c$, —$NZ^bC(NZ^b)Z^b$, and —$NZ^bC(NZ^b)NZ^cZ^c$, wherein $Z^a$, $Z^b$, and $Z^c$ are as defined above.

The compounds described herein may contain one or more chiral centers and/or double bonds and therefore, may exist as stereoisomers, such as double-bond isomers (i.e., geometric isomers such as E and Z), enantiomers or diastereomers. The invention includes each of the isolated stereoisomeric forms (such as the enantiomerically pure isomers, the E and Z isomers, and other alternatives for stereoisomers) as well as mixtures of stereoisomers in varying degrees of chiral purity or percentage of E and Z, including racemic mixtures, mixtures of diastereomers, and mixtures of E and Z isomers, unless a specific stereoisomer is specified. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The invention includes each of the isolated stereoisomeric forms as well as mixtures of stereoisomers in varying degrees of chiral purity, including racemic mixtures. It also encompasses the various diastereomers. Other structures may appear to depict a specific isomer, but that is merely for convenience, and is not intended to limit the invention to the depicted isomer. When the chemical name does not specify the isomeric form of the compound, it denotes any one of the possible isomeric forms or mixtures of those isomeric forms of the compound. As stated above, eflornithine exists in two enantiomeric forms.

The compounds may also exist in several tautomeric forms, and the depiction herein of one tautomer is for convenience only, and is also understood to encompass other tautomers of the form shown. Accordingly, the chemical structures depicted herein encompass all possible tautomeric forms of the illustrated compounds. The term "tautomer" as used herein refers to isomers that change into one another with great ease so that they can exist together in equilibrium; the equilibrium may strongly favor one of the tautomers, depending on stability considerations. For example, ketone and enol are two tautomeric forms of one compound.

As used herein, the term "solvate" means a compound formed by solvation (the combination of solvent molecules with molecules or ions of the solute), or an aggregate that consists of a solute ion or molecule, i.e., a compound of the invention, with one or more solvent molecules. When water is the solvent, the corresponding solvate is "hydrate." Examples of hydrate include, but are not limited to, hemihydrate, monohydrate, dihydrate, trihydrate, hexahydrate, and other water-containing species. It should be understood by one of ordinary skill in the art that the pharmaceutically acceptable salt, and/or prodrug of the present compound may also exist in a solvate form. The solvate is typically formed via hydration which is either part of the preparation of the present compound or through natural absorption of moisture by the anhydrous compound of the present invention.

As used herein, the term "ester" means any ester of a present compound in which any of the —COOH functions of the molecule is replaced by a —COOR function, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl and substituted derivatives thereof. The hydrolysable esters of the present compounds are the compounds whose carboxyls are present in the form of hydrolysable ester groups. That is, these esters are pharmaceutically acceptable and can be hydrolyzed to the corresponding carboxyl acid in vivo.

In addition to the substituents described above, alkyl, alkenyl and alkynyl groups can alternatively or in addition be substituted by $C_1$-$C_8$ acyl, $C_2$-$C_8$ heteroacyl, $C_6$-$C_{10}$ aryl, $C_3$-$C_8$ cycloalkyl, $C_3$-$C_8$ heterocyclyl, or $C_5$-$C_{10}$ heteroaryl, each of which can be optionally substituted. Also, in addition, when two groups capable of forming a ring having 5 to 8 ring members are present on the same or adjacent atoms, the two groups can optionally be taken together with the atom or atoms in the substituent groups to which they are attached to form such a ring.

"Heteroalkyl," "heteroalkenyl," and "heteroalkynyl" and the like are defined similarly to the corresponding hydrocarbyl (alkyl, alkenyl and alkynyl) groups, but the "hetero" terms refer to groups that contain 1-3 O, S or N heteroatoms or combinations thereof within the backbone residue; thus at least one carbon atom of a corresponding alkyl, alkenyl, or alkynyl group is replaced by one of the specified heteroatoms to form, respectively, a heteroalkyl, heteroalkenyl, or heteroalkynyl group. For reasons of chemical stability, it is also understood that, unless otherwise specified, such groups do not include more than two contiguous heteroatoms except where an oxo group is present on N or S as in a nitro or sulfonyl group.

While "alkyl" as used herein includes cycloalkyl and cycloalkylalkyl groups, the term "cycloalkyl" may be used herein to describe a carbocyclic non-aromatic group that is connected via a ring carbon atom, and "cycloalkylalkyl" may be used to describe a carbocyclic non-aromatic group that is connected to the molecule through an alkyl linker.

Similarly, "heterocyclyl" may be used to describe a non-aromatic cyclic group that contains at least one heteroatom (typically selected from N, O and S) as a ring member and that is connected to the molecule via a ring atom, which may be C (carbon-linked) or N (nitrogen-linked); and "heterocyclylalkyl" may be used to describe such a group that is connected to another molecule through a linker. The heterocyclyl can be fully saturated or partially saturated, but non-aromatic. The sizes and substituents that are suitable for the cycloalkyl, cycloalkylalkyl, heterocyclyl, and heterocyclylalkyl groups are the same as those described above for alkyl groups. The heterocyclyl groups typically contain 1, 2 or 3 heteroatoms, selected from N, O and S as ring members; and the N or S can be substituted with the groups commonly found on these atoms in heterocyclic systems. As used herein, these terms also include rings that contain a double bond or two, as long as the ring that is attached is not aromatic. The substituted cycloalkyl and heterocyclyl groups also include cycloalkyl or heterocyclic rings fused to an aromatic ring or heteroaromatic ring, provided the point of attachment of the group is to the cycloalkyl or heterocyclyl ring rather than to the aromatic/heteroaromatic ring.

As used herein, "acyl" encompasses groups comprising an alkyl, alkenyl, alkynyl, aryl or arylalkyl radical attached at one of the two available valence positions of a carbonyl carbon atom, and heteroacyl refers to the corresponding groups wherein at least one carbon other than the carbonyl carbon has been replaced by a heteroatom chosen from N, O and S.

Acyl and heteroacyl groups are bonded to any group or molecule to which they are attached through the open valence of the carbonyl carbon atom. Typically, they are $C_1$-$C_8$ acyl groups, which include formyl, acetyl, pivaloyl, and benzoyl, and $C_2$-$C_8$ heteroacyl groups, which include methoxyacetyl, ethoxycarbonyl, and 4-pyridinoyl.

Similarly, "arylalkyl" and "heteroarylalkyl" refer to aromatic and heteroaromatic ring systems which are bonded to their attachment point through a linking group such as an alkylene, including substituted or unsubstituted, saturated or unsaturated, cyclic or acyclic linkers. Typically the linker is $C_1$-$C_8$ alkyl. These linkers may also include a carbonyl group, thus making them able to provide substituents as an acyl or heteroacyl moiety. An aryl or heteroaryl ring in an arylalkyl or heteroarylalkyl group may be substituted with the same substituents described above for aryl groups. Preferably, an arylalkyl group includes a phenyl ring optionally substituted with the groups defined above for aryl groups and a $C_1$-$C_4$ alkylene that is unsubstituted or is substituted with one or two $C_1$-$C_4$ alkyl groups or heteroalkyl groups, where the alkyl or heteroalkyl groups can optionally cyclize to form a ring such as cyclopropane, dioxolane, or oxacyclopentane. Similarly, a heteroarylalkyl group preferably includes a $C_5$-$C_6$ monocyclic heteroaryl group that is optionally substituted with the groups described above as substituents typical on aryl groups and a $C_1$-$C_4$ alkylene that is unsubstituted or is substituted with one or two $C_1$-$C_4$ alkyl groups or heteroalkyl groups, or it includes an optionally substituted phenyl ring or $C_5$-$C_6$ monocyclic heteroaryl and a $C_1$-$C_4$ heteroalkylene that is unsubstituted or is substituted with one or two $C_1$-$C_4$ alkyl or heteroalkyl groups, where the alkyl or heteroalkyl groups can optionally cyclize to form a ring such as cyclopropane, dioxolane, or oxacyclopentane.

Where an arylalkyl or heteroarylalkyl group is described as optionally substituted, the substituents may be on either the alkyl or heteroalkyl portion or on the aryl or heteroaryl portion of the group. The substituents optionally present on the alkyl or heteroalkyl portion are the same as those described above for alkyl groups generally; the substituents optionally present on the aryl or heteroaryl portion are the same as those described above for aryl groups generally.

"Arylalkyl" groups as used herein are hydrocarbyl groups if they are unsubstituted, and are described by the total number of carbon atoms in the ring and alkylene or similar linker. Thus a benzyl group is a C7-arylalkyl group, and phenylethyl is a C8-arylalkyl.

"Heteroarylalkyl" as described above refers to a moiety comprising an aryl group that is attached through a linking group, and differs from "arylalkyl" in that at least one ring atom of the aryl moiety or one atom in the linking group is a heteroatom selected from N, O and S. The heteroarylalkyl groups are described herein according to the total number of atoms in the ring and linker combined, and they include aryl groups linked through a heteroalkyl linker; heteroaryl groups linked through a hydrocarbyl linker such as an alkylene; and heteroaryl groups linked through a heteroalkyl linker. Thus, for example, C7-heteroarylalkyl would include pyridylmethyl, phenoxy, and N-pyrrolylmethoxy.

"Alkylene" as used herein refers to a divalent hydrocarbyl group; because it is divalent, it can link two other groups together. Typically it refers to —$(CH_2)_n$— where n is 1-8 and preferably n is 1-4, though where specified, an alkylene can also be substituted by other groups, and can be of other lengths, and the open valences need not be at opposite ends of a chain.

In general, any alkyl, alkenyl, alkynyl, acyl, or aryl or arylalkyl group that is contained in a substituent may itself optionally be substituted by additional substituents. The nature of these substituents is similar to those recited with regard to the primary substituents themselves if the substituents are not otherwise described.

"Amino" as used herein refers to —$NH_2$, but where an amino is described as "substituted" or "optionally substituted", the term includes NR'R" wherein each R' and R" is independently H, or is an alkyl, alkenyl, alkynyl, acyl, aryl, or arylalkyl group, and each of the alkyl, alkenyl, alkynyl, acyl, aryl, or arylalkyl groups is optionally substituted with the substituents described herein as suitable for the corresponding group; the R' and R" groups and the nitrogen atom to which they are attached can optionally form a 3- to 8-membered ring which may be saturated, unsaturated or aromatic and which contains 1-3 heteroatoms independently selected from N, O and S as ring members, and which is optionally substituted with the substituents described as suitable for alkyl groups or, if NR'R" is an aromatic group, it is optionally substituted with the substituents described as typical for heteroaryl groups.

As used herein, the term "carbocycle," "carbocyclyl," or "carbocyclic" refers to a cyclic ring containing only carbon atoms in the ring, whereas the term "heterocycle" or "heterocyclic" refers to a ring comprising a heteroatom. The carbocyclyl can be fully saturated or partially saturated, but non-aromatic. For example, the carbocyclyl encompasses cycloalkyl. The carbocyclic and heterocyclic structures encompass compounds having monocyclic, bicyclic or multiple ring systems; and such systems may mix aromatic, heterocyclic, and carbocyclic rings. Mixed ring systems are described according to the ring that is attached to the rest of the compound being described.

As used herein, the term "heteroatom" refers to any atom that is not carbon or hydrogen, such as nitrogen, oxygen or sulfur. When it is part of the backbone or skeleton of a chain or ring, a heteroatom must be at least divalent, and will typically be selected from N, O, P, and S.

As used herein, the term "alkanoyl" refers to an alkyl group covalently linked to a carbonyl (C=O) group. The term "lower alkanoyl" refers to an alkanoyl group in which the alkyl portion of the alkanoyl group is $C_1$-$C_6$. The alkyl portion of the alkanoyl group can be optionally substituted as described above. The term "alkylcarbonyl" can alternatively be used. Similarly, the terms "alkenylcarbonyl" and "alkynylcarbonyl" refer to an alkenyl or alkynyl group, respectively, linked to a carbonyl group.

As used herein, the term "alkoxy" refers to an alkyl group covalently linked to an oxygen atom; the alkyl group can be considered as replacing the hydrogen atom of a hydroxyl group. The term "lower alkoxy" refers to an alkoxy group in which the alkyl portion of the alkoxy group is $C_1$-$C_6$. The alkyl portion of the alkoxy group can be optionally substituted as described above. As used herein, the term "haloalkoxy" refers to an alkoxy group in which the alkyl portion is substituted with one or more halo groups.

As used herein, the term "sulfo" refers to a sulfonic acid (—$SO_3H$) substituent.

As used herein, the term "sulfamoyl" refers to a substituent with the structure —$S(O_2)NH_2$, wherein the nitrogen of the $NH_2$ portion of the group can be optionally substituted as described above.

As used herein, the term "carboxyl" refers to a group of the structure —$C(O_2)H$.

As used herein, the term "carbamyl" refers to a group of the structure —$C(O_2)NH_2$, wherein the nitrogen of the $NH_2$ portion of the group can be optionally substituted as described above.

As used herein, the terms "monoalkylaminoalkyl" and "dialkylaminoalkyl" refer to groups of the structure -$Alk_1$-NH-$Ak_2$ and -$Alk_1$-N($Alk_2$)($Alk_3$), wherein $Alk_1$, $Alk_2$, and $Alk_3$ refer to alkyl groups as described above.

As used herein, the term "alkylsulfonyl" refers to a group of the structure —$S(O)_2$-Alk wherein Alk refers to an alkyl group as described above. The terms "alkenylsulfonyl" and "alkynylsulfonyl" refer analogously to sulfonyl groups covalently bound to alkenyl and alkynyl groups, respectively. The term "arylsulfonyl" refers to a group of the structure —S(O)$_2$—Ar wherein Ar refers to an aryl group as described above. The term "aryloxyalkylsulfonyl" refers to a group of the structure —S(O)$_2$-Alk-O—Ar, where Alk is an alkyl group as described above and Ar is an aryl group as described above. The term "arylalkylsulfonyl" refers to a group of the structure —S(O)$_2$-AlkAr, where Alk is an alkyl group as described above and Ar is an aryl group as described above.

As used herein, the term "alkyloxycarbonyl" refers to an ester substituent including an alkyl group wherein the carbonyl carbon is the point of attachment to the molecule. An example is ethoxycarbonyl, which is CH$_3$CH$_2$OC(O)—. Similarly, the terms "alkenyloxycarbonyl," "alkynyloxycarbonyl," and "cycloalkylcarbonyl" refer to similar ester substituents including an alkenyl group, alkenyl group, or cycloalkyl group respectively. Similarly, the term "aryloxycarbonyl" refers to an ester substituent including an aryl group wherein the carbonyl carbon is the point of attachment to the molecule. Similarly, the term "aryloxyalkylcarbonyl" refers to an ester substituent including an alkyl group wherein the alkyl group is itself substituted by an aryloxy group.

Other combinations of substituents are known in the art and, are described, for example, in U.S. Pat. No. 8,344,162 to Jung et al., incorporated herein by this reference. For example, the term "thiocarbonyl" and combinations of substituents including "thiocarbonyl" include a carbonyl group in which a double-bonded sulfur replaces the normal double-bonded oxygen in the group. The term "alkylidene" and similar terminology refer to an alkyl group, alkenyl group, alkynyl group, or cycloalkyl group, as specified, that has two hydrogen atoms removed from a single carbon atom so that the group is double-bonded to the remainder of the structure.

The compounds disclosed herein may exist as salts at physiological pH ranges or other ranges. Such salts are described further below. In general, the term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either net or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either net or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isbutyric, oxalic, maleic, malonic, benzoic, succinic, suberic, fumeric, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge, S. M., et al., "Pharmaceutical Salts", Journal of Pharmaceutical Science, 1977, 66, 1-19). Certain specific compounds of the present inventions contain both basic and acidic functionalities that allow the compounds to be converted into either base or acid addition salts.

The pharmaceutical composition according to the present invention can, in one alternative, include a prodrug, including a prodrug of eflornithine. When a pharmaceutical composition according to the present invention includes a prodrug, prodrugs and active metabolites of a compound may be identified using routine techniques known in the art. See, e.g., Bertolini et al., J. Med. Chem., 40, 2011-2016 (1997); Shan et al., J. Pharm. Sci., 86 (7), 765-767; Bagshawe, Drug Dev. Res., 34, 220-230 (1995); Bodor, Advances in Drug Res., 13, 224-331 (1984); Bundgaard, Design of Prodrugs (Elsevier Press 1985); Larsen, Design and Application of Prodrugs, Drug Design and Development (Krogsgaard-Larsen et al., eds., Harwood Academic Publishers, 1991); Dear et al., J. Chromatogr. B, 748, 281-293 (2000); Spraul et al., J. Pharmaceutical & Biomedical Analysis, 10, 601-605 (1992); and Prox et al., Xenobiol., 3, 103-112 (1992).

When the pharmacologically active compound in a pharmaceutical composition according to the present invention possesses a sufficiently acidic, a sufficiently basic, or both a sufficiently acidic and a sufficiently basic functional group, these group or groups can accordingly react with any of a number of inorganic or organic bases, and inorganic and organic acids, to form a pharmaceutically acceptable salt. Exemplary pharmaceutically acceptable salts include those salts prepared by reaction of the pharmacologically active compound with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, 3-hydroxybutyrates, glycolates, tartrates, methane-sulfonates, propanesulfonates, naphthalene-1-sulfonates, naphthalene-2-sulfonates, and mandelates. If the pharmacologically active compound has one or more basic functional groups, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. If the pharmacologically active compound has one or more acidic functional groups, the desired pharmaceutically acceptable salt may be prepared by any suitable method available in the art, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

In the case of agents that are solids, it is understood by those skilled in the art that the inventive compounds and salts may exist in different crystal or polymorphic forms, all of which are intended to be within the scope of the present invention and specified formulas.

The compositions of the invention may be manufactured using techniques generally known for preparing pharmaceutical compositions, e.g., by conventional techniques such as mixing, dissolving, granulating, dragee-making, levitating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations, which can be used pharmaceutically.

Proper formulation is dependent upon the route of administration chosen. For injection, the agents of the invention may be formulated into aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers known in the art. Such carriers enable the compounds of the invention to be formulated as tablets, pills, dragees, capsules, liquids, gels, syrups, slurries, solutions, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agents.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate, and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in conventional manner.

Pharmaceutical formulations for parenteral administration can include aqueous solutions or suspensions. Suitable lipophilic solvents or vehicles include fatty oils such as sesame oil or synthetic fatty acid esters, such as ethyl oleate or triglycerides. Aqueous injection suspensions may contain substances which increase the viscosity of the suspension, such as sodium carboxymethyl cellulose, sorbitol, or dextran. Optionally, the suspension may also contain suitable stabilizers or modulators which increase the solubility or dispersibility of the composition to allow for the preparation of highly concentrated solutions, or can contain suspending or dispersing agents. Pharmaceutical preparations for oral use can be obtained by combining the pharmacologically active agent with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating modulators may be added, such as the cross-linked polyvinyl pyrrolidone, agar, or alginic acid or a salt thereof such as sodium alginate.

Other ingredients such as stabilizers, for example, antioxidants such as sodium citrate, ascorbyl palmitate, propyl gallate, reducing agents, ascorbic acid, vitamin E, sodium bisulfite, butylated hydroxytoluene, BHA, acetylcysteine, monothioglycerol, phenyl-α-naphthylamine, or lecithin can be used. Also, chelators such as EDTA can be used. Other ingredients that are conventional in the area of pharmaceutical compositions and formulations, such as lubricants in tablets or pills, coloring agents, or flavoring agents, can be used. Also, conventional pharmaceutical excipients or carriers can be used. The pharmaceutical excipients can include, but are not necessarily limited to, calcium carbonate, calcium phosphate, various sugars or types of starch, cellulose derivatives, gelatin, vegetable oils, polyethylene glycols and physiologically compatible solvents. Other pharmaceutical excipients are well known in the art. Exemplary pharmaceutically acceptable carriers include, but are not limited to, any and/or all of solvents, including aqueous and non-aqueous solvents, dispersion media, coatings, antibacterial and/or antifungal agents, isotonic and/or absorption delaying agents, and/or the like. The use of such media and/or agents for pharmaceutically active substances is well known in the art. Except insofar as any conventional medium, carrier, or agent is incompatible with the active ingredient or ingredients, its use in a composition according to the present invention is contemplated. Supplementary active ingredients can also be incorporated into the compositions, particularly as described above. For administration of any of the compounds used in the present invention, preparations should meet sterility, pyrogenicity, general safety, and purity standards as required by the FDA Office of Biologics Standards or by other regulatory organizations regulating drugs.

For administration intranasally or by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents, which increase the solubility of the compounds to allow for the preparation of highly concentrated solutions.

Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides.

In addition to the formulations described above, the compounds may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

A pharmaceutical composition can be administered by a variety of methods known in the art. The routes and/or modes of administration vary depending upon the desired results. Depending on the route of administration, the pharmacologically active agent may be coated in a material to protect the therapeutic agent or agents from the action of acids and other compounds that may inactivate the agent. Conventional pharmaceutical practice can be employed to provide suitable formulations or compositions for the administration of such pharmaceutical compositions to subjects. Any appropriate route of administration can be employed, for example, but not limited to, intravenous, parenteral, intraperitoneal, intravenous, transcutaneous, subcutaneous, intramuscular, or oral administration. Depending on the severity of the malignancy or other disease, disorder, or condition to be treated, as well as other conditions affecting the subject to be treated, either systemic or localized delivery of the pharmaceutical composition can be used in the course of treatment. The pharmaceutical composition as described above can be administered together with additional therapeutic agents intended to treat a particular disease or condition, which may be the same disease or condition that the pharmaceutical composition is intended to treat, which may be a related disease or condition, or which even may be an unrelated disease or condition.

As detailed above, eflornithine and derivatives, analogs, or prodrugs thereof have been described as effective for the treatment of glioma, in particular with respect to inhibiting or slowing the progression of glioma to a higher grade. However, all forms of cancer are associated with mutation in malignant cells, so eflornithine or derivatives, analogs, or prodrugs thereof can be similarly administered to inhibit or slow the advance of other malignancies as well by preventing mutation in the malignant cells. Although eflornithine or its derivatives, analogs, or prodrugs can be used to slow the advance of and prevent mutation in many types of cancers, in particular, eflornithine or its derivatives analogs, or prodrugs can be used to treat neuroblastoma. Accordingly, compositions according to the present invention can be used to treat neuroblastoma and other malignancies. Eflornithine or its derivatives, analogs, or prodrugs increase the concentration of p21 (waf1/cip1) and p27kip-1 and this acts as a cause of cell cycle arrest. Among the tumor types for which such observations have been made are leukemia, pancreatic cancer, neuroblastoma, mammary tumors, and gastric cancer. This is addressed in the following references: (i) P. M. Bauer et al., "Role of p42/p44 Mitogen-Activated-Protein Kinase and p21waf1/cip1 in the Regulation of Vascular Smooth Muscle Cell Proliferation by Nitric Oxide," *Proc. Natl. Acad. Sci. USA* 98: 12802-12807 (2001); (ii) S. H. Choi et al., "Polyamine-Depletion Induces p27Kip1 and Enhances Dexamethasone-Induced G1 Arrest and Apoptosis in Human T lymphoblastic Leukemia Cells," *Leukemia Res.* 24: 119-127 (2000); (iii) H. Guo et al., "RhoA Stimulates IEC-6 Cell Proliferation by Increasing Polyamine-Dependent Cdk2 Activity," *Am. J. Physiol. Gastrointest. Liver Physiol.* 285: G704-713 (2003); (iv) L. Li et al., "JunD Stabilization Results in Inhibition of Normal Intestinal Epithelial Cell Growth through P21 after Polyamine Depletion," *Gastroenterology* 123: 764-779 (2002); (v) M. Li et al., "Chemoprevention of Mammary Carcinogenesis in a Transgenic Mouse Model by Alpha-Difluoromethylornithine (DFMO) in the Diet Is associated with Decreased Cyclin D1 Activity," *Oncogene* 22: 2568-2572 (2003); (vi) A. Mohammed et al., "Eflornithine (DFMO) Prevents Progression of Pancreatic Cancer by Modulating Ornithine Decarboxylase Signaling," *Cancer Prev. Res.* 7: 1198-1209 (2014); (vii) T. Nemoto et al., "p53 Independent G(1) arrest Induced by DL-Alpha-Difluoromethylornithine," *Biochem. Biophys. Res. Commun.* 280: 848-854 (2001); (viii) "R. M. Ray et al., "Polyamine Depletion Arrests Cell Cycle and Induces Inhibitors p21(Waf1/Cip1), p27(Kip1), and p53 in IEC-6 Cells," *Am. J Physiol.* 276: C684-691 (1999); (ix) R. J. Rounbehler et al., "Targeting Ornithine Decarboxylase Impairs Development of MYCN-Amplified Neuroblastoma," *Cancer Res.* 69: 547-553 (2009); (x) J. Singh et al., "Modulation of Azoxymethane-Induced Mutational Activation of ras Protooncogenes by Chemopreventive Agents in Colon Carcinogenesis," *Carcinogenesis* 15: 1317-1323 (1994); (xi) R. Singh et al., "Activation of Caspase-3 Activity and Apoptosis in MDA-MB-468 Cells by N(omega)-Hydroxy-L-Arginine, an Inhibitor of Arginase, Is Not Solely Dependent on Reduction in Intracellular Polyamines," *Carcinogenesis* 22: 1863-1869 (2001); (xii) L. Tao et al., "Altered Expression of c-myc, p16 and p27 in Rat Colon Tumors and Its Reversal by Short-Term Treatment with Chemopreventive Agents." *Carcinogenesis* 23: 1447-1454

(2002); (xiii) C. J. Wallick et al., "Key Role for p27Kip1, Retinoblastoma Protein Rb, and MYCN in Polyamine Inhibitor-Induced G1 Cell Cycle Arrest in MYCN-Amplified Human Neuroblastoma Cells," *Oncogene* 24: 5606-5618 (2005); (xiv) Q. Xiang et al., "[Apoptotic Induction of Human Lung Carcinoma A549 Cells by DFMO through Fas/FasL Pathway]," *Ai Zheng* 12: 1260-1263 (2003); and References (9) and (10), below.

The invention is illustrated by the following Examples. These Examples are included for illustrative purposes only, and are not intended to limit the invention.

Example 1

Eflornithine Oral Solution

An eflornithine oral solution was prepared according to the proportions described in Table 1. Sodium benzoate and saccharin sodium dihydrate were added to purified water and mixed to achieve a clear solution. The solution was then heated to approximately 55° C. and eflornithine was added to achieve full dissolution. Aqueous solution of sodium benzoate, saccharin sodium and eflornithine was then cooled to approximately 30° C. and glycerin and propylene glycol were added and mixed until the solution was clear. The solution was tested for drug content and sodium benzoate content by High Performance Liquid Chromatography (HPLC). The solution was also tested for antimicrobial effectiveness and microbial count at preparation and after 28 days of storage.

TABLE 1

| Ingredient | Function | % Wt |
|---|---|---|
| Eflornithine HCl•H$_2$O | API | 18.0% |
| Sodium Benzoate | Preservative | 0.15% |
| Saccharin Sodium Dihydrate | Sweetening agent | 0.15% |
| Glycerol | Thickening agent | 3.0% |
| Propylene Glycol | Thickening agent | 5.0% |
| Purified Water | Solvent | 73.70% |

Example [N71]2

Eflornithine Oral Solution Dosing Regimen (Prospective Example)

Eflornithine oral solution as prepared in Example 1 may be administered three times a day to provide 2.8 g/m$^2$ eflornithine free base equivalent per single dose. The dosing may be continued for 2 weeks, then interrupted for one week and continued again for 2 weeks. This pattern can be continued for the entire therapy duration. Alternatively, the duration of dosing in each cycle may be adjusted to 3 or 4 weeks to achieve the desired therapeutic effect. Alternatively, the interruption of the dosing may be adjusted in each cycle to 2 or 3 weeks to ensure minimization of the adverse events.

Example 3

Co-Administration of Eflornithine Oral Solution with Adjuvant Therapeutic Agents (Prospective Example)

Eflornithine oral solution as prepared in Example 1 may be administered with or without an adjuvant therapeutic agent, such as lomustine. When administered with an adjuvant therapeutic agent, it is preferable that eflornithine is administered alone for 2 weeks prior to administration of the adjuvant therapeutic agent. In this example, eflornithine oral solution is administered for 2 weeks, three times a day to provide 2.8 g/m$^2$ eflornithine free base equivalent per single dose. A prescribed amount of lomustine (e.g. 110 mg/m$^2$) is then administered as a single dose. Following a 1-week interruption, the eflornithine is dosed for another 2 weeks, three times a day to provide 2.8 g/m$^2$ eflornithine free base equivalent per single dose. This pattern may be continued for the entire therapy duration or may be adjusted to achieve the desired therapeutic effect and minimize the adverse events.

Example 4

Fast-Dissolve Formulations

Fast-dissolve formulations with high drug load that provided initial positive results (<30 sec dispersion time and acceptable assay level) are listed in Table 2. These formulations disperse into cloudy solutions that eventually settle, but can be easily re-suspended by manual shaking. These formulations can also be compressed into large tablets that easily disintegrate.

TABLE 2

| Material | Formulation 3 | Formulation 4 | Formulation 5 |
|---|---|---|---|
| Eflornithine HCl•H2O | 50% | 50% | 50% |
| Saccharin Sodium Dihydrate | 1% | 1% | 1% |
| Mannitol | 30% | 35% | 35% |
| Croscarmellose sodium (Vivasol) | 10% | — | 7% |
| Sodium Starch Glycolate | 9% | 7% | — |
| Camphor | — | 7% | 7% |

Example 5

Eflornithine Powder for Oral Solution

Eflornithine powder for oral solution can be prepared as follows: 99% wt eflornithine and 1% wt of saccharin sodium dihydrate can be compounded and dispensed into individual pouches of desired dosage strengths (e.g. 5 g). The powder would be mixed with water or juice for oral administration. This formulation can be optimized for best flow or compressibility.

Example 6

Suspensions

Suspensions can be prepared with a high drug load. The formulations for these suspensions are shown in Table 3. Typically, suspensions are used for poorly soluble drugs. For the highly soluble compound like eflornithine, a saturated solution is first made and then excess drug is suspended in it. This formulation can be optimized for stabilization of the suspension.

TABLE 3

| Material | Formulation 1 | Formulation 2 |
|---|---|---|
| Eflornithine HCl·H₂O | 50% | 50% |
| Glycerol | 7.5% | 7.5% |
| Saccharin Sodium Dihydrate | 0.2% | 0.2% |
| Sorbitol | 0% | 15% |
| Na Benzoate | 0.2% | 0.2% |
| Avicel RC-591 | 2.5% | 2.5% |
| Water | 40% | 25% |

The eflornithine in these compositions is preferably micronized.

Example 7

A formulation screening experiment was conducted to enhance robustness of eflornithine oral solution. Twenty formulations were prepared to investigate the effect of solvent system composition and eflornithine concentration on physical stability of the formulations. The experiments were conducted at room temperature and with refrigeration/freezing and specifically addressed the effect of local increase in drug concentration on precipitation of the product. The physical stability of formulations was assessed by visual observation. The results of the study suggested that while the entire range of excipient levels examined in this experiment provided a high level of robustness at ambient and low temperatures, decrease of eflornithine concentration from 20 to 18% offered added benefits in terms of higher resistance to freezing and related short-term crystallization. The working ranges for levels of propylene glycol and glycerol in the new eflornithine oral solution formulation have been defined as 5 and 3%, respectively. The concentration ranges for these components have been characterized to provide understanding of the physical stability of the formulation in a wide variety of solvent system compositions.

The objective was to investigate the effect of solvent system composition and eflornithine concentration on the physical stability of eflornithine oral solution formulation. The experiment was designed as three-factor mixed-level DOE, as shown in Table 4. The variables studied in this experiment included eflornithine concentration at 18 and 20% levels, propylene glycol (PG) concentration at 0, 5 and 10% levels and glycerol concentration at 0, 3 and 6% levels. The amount of water varied to attain the total formulation amount. The compositions of the formulations are shown in Table 5.

TABLE 4

| Run # | Eflornithine, Coded | PG, Coded | Glycerol, Coded | Eflornithine, % | PG, % | Glycerol, % |
|---|---|---|---|---|---|---|
| 1 | 0 | -1 | -1 | 18 | 0 | 0 |
| 2 | 0 | -1 | 0 | 18 | 0 | 3 |
| 3 | 0 | -1 | 1 | 18 | 0 | 6 |
| 4 | 0 | 0 | -1 | 18 | 5 | 0 |
| 5 | 0 | 0 | 0 | 18 | 5 | 3 |
| 6 | 0 | 0 | 1 | 18 | 5 | 6 |
| 7 | 0 | 1 | -1 | 18 | 10 | 0 |
| 8 | 0 | 1 | 0 | 18 | 10 | 3 |
| 9 | 0 | 1 | 1 | 18 | 10 | 6 |
| 10 | 0 | 1 | 0.83 | 18 | 5 | 5 |
| 11 | 1 | -1 | -1 | 20 | 0 | 0 |
| 12 | 1 | -1 | 0 | 20 | 0 | 3 |
| 13 | 1 | -1 | 1 | 20 | 0 | 6 |
| 14 | 1 | 0 | -1 | 20 | 5 | 0 |
| 15 | 1 | 0 | 0 | 20 | 5 | 3 |
| 16 | 1 | 0 | 1 | 20 | 5 | 6 |
| 17 | 1 | 1 | -1 | 20 | 10 | 0 |
| 18 | 1 | 1 | 0 | 20 | 10 | 3 |
| 19 | 1 | 1 | 1 | 20 | 10 | 6 |
| 20 | 1 | 1 | 0.83 | 20 | 5 | 5 |

TABLE 5

| Ingredient | Eflornithine HCl-H₂O | Sodium Benzoate | Saccharin Sodium Dihydrate | Glycerol | Propylene Glycol | Purified Water |
|---|---|---|---|---|---|---|
| Formulation 1 | 18.00% | 0.15% | 0.15% | 0.00% | 0.00% | 81.70% |
| Formulation 2 | 18.00% | 0.15% | 0.15% | 3.00% | 0.00% | 78.70% |
| Formulation 3 | 18.00% | 0.15% | 0.15% | 6.00% | 0.00% | 75.70% |
| Formulation 4 | 18.00% | 0.15% | 0.15% | 0.00% | 5.00% | 76.70% |
| Formulation 5 | 18.00% | 0.15% | 0.15% | 3.00% | 5.00% | 73.70% |
| Formulation 6 | 18.00% | 0.15% | 0.15% | 6.00% | 5.00% | 70.70% |
| Formulation 7 | 18.00% | 0.15% | 0.15% | 0.00% | 10.00% | 71.70% |
| Formulation 8 | 18.00% | 0.15% | 0.15% | 3.00% | 10.00% | 68.70% |
| Formulation 9 | 18.00% | 0.15% | 0.15% | 6.00% | 10.00% | 65.70% |
| Formulation 10 | 18.00% | 0.15% | 0.15% | 5.00% | 5.00% | 71.70% |
| Formulation 11 | 20.00% | 0.15% | 0.15% | 0.00% | 0.00% | 79.70% |
| Formulation 12 | 20.00% | 0.15% | 0.15% | 3.00% | 0.00% | 76.70% |
| Formulation 13 | 20.00% | 0.15% | 0.15% | 6.00% | 0.00% | 73.70% |
| Formulation 14 | 20.00% | 0.15% | 0.15% | 0.00% | 5.00% | 74.70% |
| Formulation 15 | 20.00% | 0.15% | 0.15% | 3.00% | 5.00% | 71.70% |
| Formulation 16 | 20.00% | 0.15% | 0.15% | 6.00% | 5.00% | 68.70% |
| Formulation 17 | 20.00% | 0.15% | 0.15% | 0.00% | 10.00% | 69.70% |
| Formulation 18 | 20.00% | 0.15% | 0.15% | 3.00% | 10.00% | 66.70% |
| Formulation 19 | 20.00% | 0.15% | 0.15% | 6.00% | 10.00% | 63.70% |
| Formulation 20 | 20.00% | 0.15% | 0.15% | 5.00% | 5.00% | 69.70% |

The formulations were prepared in clear 20-cc scintillation vials. Sodium benzoate and saccharin sodium dihydrate was dispensed to each vial and purified water added to achieve a clear solution. The solution was then heated to approximately 55° C. and eflornithine was added and mixed using a Vortex mixer for approximately 1 minute to achieve a clear solution. Aqueous solution of sodium benzoate, saccharin sodium and eflornithine was then cooled to room temperature and glycerin and propylene glycol were added into each vial and mixed until the solution was clear. The formulations were filtered using 0.2 µm syringe filter (Gelman Science #4454), split into two aliquots of 4.5 to 4.8 g and filled into 8-mL clear HPLC vials. The vials were placed in a refrigerator at 0° C. for 56 hours, removed and inspected.

In order to test robustness of the formulations, one of the vials of each formulation was "seeded" with eflornithine (0.003±0.0005 g). After adding eflornithine, the formulations were mixed using a Vortex mixer for approximately 2-3 seconds and inspected. The vials were inspected again after 6 hours at room temperature, then placed in a refrigerator at 0° C. for 12 hours and inspected again.

The second vial of each formulation was used to sample 2 g of each formulation and place into 4-mL clear HPLC vials. Eflornithine in the amount of 0.003±0.0005 g was then added into each 2-g aliquot of formulation and inspected. The vials were inspected again after 6 hours at room temperature, then placed in refrigerator at 0° C. for 12 hours and inspected again.

For reference, the amount of eflornithine used to "seed" the formulations (0.003 g) is illustrated in FIG. 1.

Figure 2:
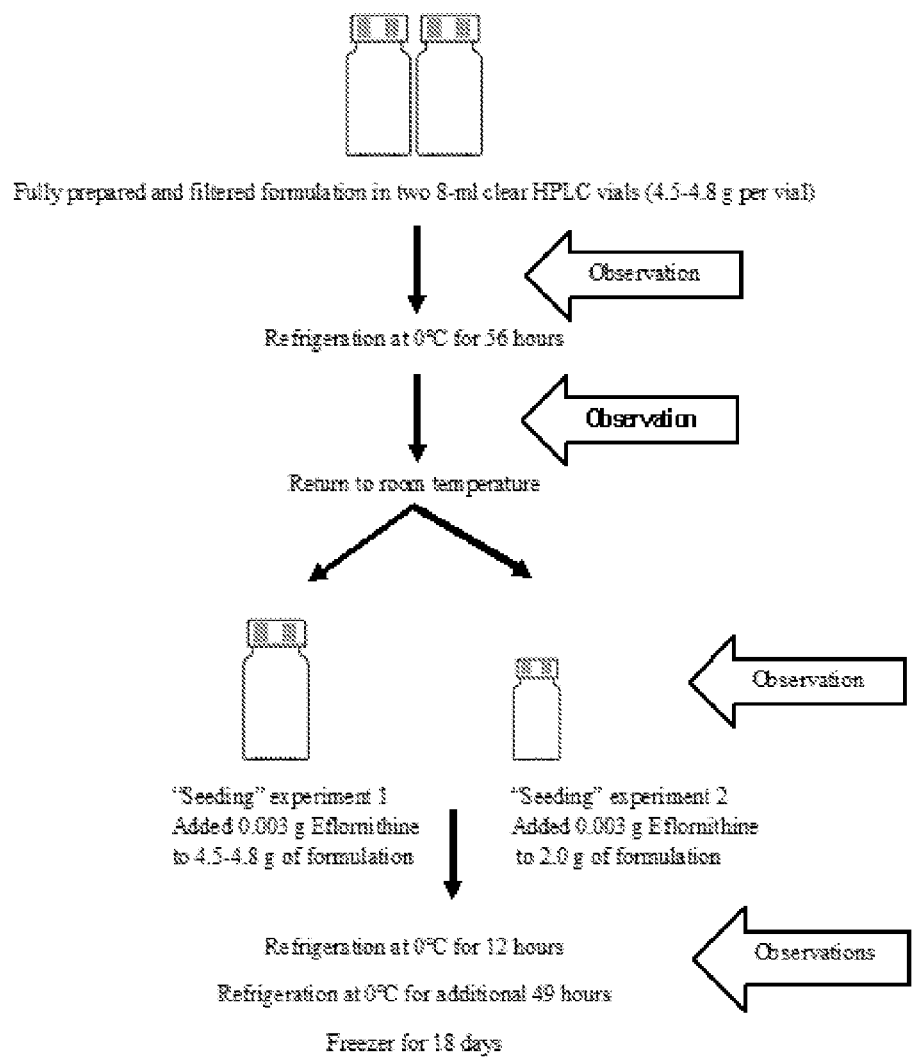
FIG. 2 is a schematic diagram showing the process of formulation testing in Example 4.

Observations of formulation clarity and potential precipitation were made after each part of the experiment (see FIG. 2 for formulation testing schematics).

There were no notable observations during eflornithine oral solution preparation. All solutions were clear as prepared with no crystals noted in any formulation. Refrigeration of solutions at 0° C. for 56 hours did not produce precipitation in any formulation.

"Seeding" with eflornithine did not cause precipitation in any samples. It was noted during addition of eflornithine into the vials with 20% formulations that the particles of the API were visible on the bottom of the bottles, but readily dissolved after shaking or mixing using a Vortex mixer for 1-2 seconds. Addition of eflornithine into the 18% formulations was seamless and did not require considerable shaking or use of a Vortex mixer.

The samples were then placed in refrigerator at 0° C. After inspecting each sample at 12-hour time point, the samples were placed into a refrigerator again and upon additional inspection showed no precipitation at 49-hr time point. Finally, the samples were placed in the freezer at −18° C. for 18 days and inspected again. Some solutions froze and showed crystallization immediately upon unfreezing at ambient conditions. However, once the solutions were shaken and reached close to room temperature, the entire precipitate dissolved with formation of clear solution. The clarity of the solutions and complete absence of visible precipitation was confirmed again in 24 hours.

The summary of observations in terms of precipitation and freezing is shown in Table 6. The freezing trend in "seeded" solutions was analyzed using JMP™ fit model/nominal logistic fit. It was shown that in the range of 0 to 6% glycerol there was no freezing of the formulations. Further analysis of reduced model (FIG. 3) showed that both eflornithine and propylene glycol concentrations have significant effects on propensity of the formulation to freeze at 18° C. The trends are opposite in directions (see signs of parameter estimates): minimal freezing can be achieved at higher concentrations of propylene glycol and lower level of eflornithine.

TABLE 6

| | | | | Precipitation | | |
|---|---|---|---|---|---|---|
| | | | | | "Seeding" 1 and 2 at RT followed by 0° C. for 12 + 49 hrs And −18° C. for 18 days | Freezing −18° C. for 18 days ("Seeding" 2 only) |
| Run # | DFMO, % | PG, % | Glycerol, % | After 56 hours at 0° C. | | |
| 1 | 18 | 0 | 0 | no | no | yes |
| 2 | 18 | 0 | 3 | no | no | yes |
| 3 | 18 | 0 | 6 | no | no | no |
| 4 | 18 | 5 | 0 | no | no | no |
| 5 | 18 | 5 | 3 | no | no | no |
| 6 | 18 | 5 | 6 | no | no | no |
| 7 | 18 | 10 | 0 | no | no | no |
| 8 | 18 | 10 | 3 | no | no | no |
| 9 | 18 | 10 | 6 | no | no | no |
| 10 | 18 | 5 | 5 | no | no | no |
| 11 | 20 | 0 | 0 | no | no | yes |
| 12 | 20 | 0 | 3 | no | no | yes |
| 13 | 20 | 0 | 6 | no | no | yes |
| 14 | 20 | 5 | 0 | no | no | yes |
| 15 | 20 | 5 | 3 | no | no | no |
| 16 | 20 | 5 | 6 | no | no | yes |
| 17 | 20 | 10 | 0 | no | no | yes |
| 18 | 20 | 10 | 3 | no | no | yes |
| 19 | 20 | 10 | 6 | no | no | no |
| 20 | 20 | 5 | 5 | no | no | no |

An 18% oral formulation of eflornithine for scale-up is shown in Table 7.

TABLE 7

| Ingredient | Function | % Wt |
|---|---|---|
| Eflornithine HCl•H$_2$0 | API | 18.0% |
| Sodium Benzoate | Preservative | 0.15% |
| Saccharin Sodium Dihydrate | Sweetening agent | 0.15% |
| Glycerol | Thickening agent | 3.0% |
| Propylene Glycol | Thickening agent | 5.0% |
| Purified Water | Solvent | 73.70% |

The effect of solvent system composition and eflornithine concentration on physical stability of eflornithine oral solution formulation has been investigated at three different temperatures: ambient, 0° C. and −18° C. The results of the study suggested that while the entire range of excipient levels examined in this experiment provided a high level of robustness at ambient and low temperatures, decrease of eflornithine concentration to 18% offered added benefits in terms of higher resistance to freezing and related short-term crystallization.

The following publications are incorporated herein by this reference. These publications are referred to herein by the numbers provided below. The inclusion of any publication in this list of publications is not to be taken as an admission that any publication referred to herein is prior art.

1. Metcalf R, Bey P, Danzin C, Jung M J, Casara P, Vevert J P. Catalytic irreversible inhibition of mammalian ornithine decarboxylase (EC 4.1.1.17) by substrate and analog product analogs. J Am Chem Soc. 1978; 100:2551-2552.
2. Bacchi C J, Garofalo J, Mockenhaupt D, et al. In vivo effects of alpha-D L-difluoromethylornithine on the metabolism and morphology of *Trypanosoma brucei brucei*. Mol Biochem Parasitol. March 1983; 7(3):209-225.
3. Bacchi C J, Nathan H C, Hutner S H, McCann P P, Sjoerdsma A. Polyamine metabolism: a potential therapeutic target in trypanosomes. Science. Oct. 17, 1980; 210(4467):332-334.

4. Shantz L M, Levin V A. Regulation of ornithine decarboxylase during oncogenic transformation: mechanisms and therapeutic potential. *Amino Acids*. August 2007; 33(2):213-223.
5. Childs A C, Mehta D J, Gerner E W. Polyamine-dependent gene expression. *Cell Mol Life Sci*. July 2003; 60(7): 1394-1406.
6. Gerner E W, Meyskens F L, Jr. Polyamines and cancer: old molecules, new understanding. *Nat Rev Cancer*. October 2004; 4(10):781-792.
7. Levin V A, Hess K R, Choucair A, et al. Phase III randomized study of postradiotherapy chemotherapy with combination alpha-difluoromethylornithine-PCV versus PCV for anaplastic gliomas. *Clinical Cancer Research*. March 2003; 9(3):981-990.
8. Levin V A, Hess K R, Choucair A K, et al. Final report for evaluable patients treated on DM92-035, phase III randomized study of post-irradiation PCV versus DFMO-PCV, for anaplastic gliomas (AG). *Neuro Oncol*. 2012; 14(Supplement 6):vi74.
9. Koomoa D L, Yco L P, Borsics T, Wallick C J, Bachmann A S. Ornithine decarboxylase inhibition by DFMO activates opposing signaling pathways via phosphorylation of both Akt/PKB and p27Kip1 in neuroblastoma. *Cancer Res*. Dec. 1, 2008; 68(23):9825-9831.
10. Koomoa D L, Geerts D, Lange I, et al. DFMO/eflornithine inhibits migration and invasion downstream of MYCN and involves p27Kip1 activity in neuroblastoma. *Int J Oncol*. April 2013; 42(4):1219-1228.
11. Johnson B E, Mazor T, Hong C, et al. Mutational Analysis Reveals the Origin and Therapy-Driven Evolution of Recurrent Glioma. *Science*. Dec. 12, 2013.
12. Hunter C, Smith R, Cahill D P, et al. A hypermutation phenotype and somatic MSH6 mutations in recurrent human malignant gliomas after alkylator chemotherapy. *Cancer Res*. Apr. 15, 2006; 66(8):3987-3991.
13. Yip S, Miao J, Cahill D P, et al. MSH6 mutations arise in glioblastomas during temozolomide therapy and mediate temozolomide resistance. *Clin Cancer Res*. Jul. 15, 2009; 15(14):4622-4629.
14. The Cancer Genome Atlas Research Network. Comprehensive genomic characterization defines human glioblastoma genes and core pathways. *Nature*. 2008; 455:1061-1068.
15. Bodell W J, Gaikwad N W, Miller D, Berger M S. Formation of DNA adducts and induction of lacI mutations in Big Blue Rat-2 cells treated with temozolomide: implications for the treatment of low-grade adult and pediatric brain tumors. *Cancer Epidemiol Biomarkers Prev*. June 2003; 12(6):545-551.
16. Einspahr J G, Nelson M A, Saboda K, Warneke J, Bowden G T, Alberts D S. Modulation of biologic endpoints by topical difluoromethylornithine (DFMO), in subjects at high-risk for nonmelanoma skin cancer. *Clin Cancer Res*. January 2002; 8(1):149-155.
17. Hoshino T, Prados M, Wilson C B, Cho K G, Lee K S, Davis R L. Prognostic implications of the bromodeoxyuridine labeling index of human gliomas. *J Neurosurg*. 1989; 71(3):335-341.
18. Labrousse F, Daumas-Duport C, Batorski L, Hoshino T. Histological grading and bromodeoxyuridine labeling index of astrocytomas. Comparative study in a series of 60 cases. *J Neurosurg*. 1991; 75(2):202-205.
19. Prados M D, Krouwer H G, Edwards M S, Cogen P H, Davis R L, Hoshino T. PROLIFERATIVE POTENTIAL AND OUTCOME IN PEDIATRIC ASTROCYTIC TUMORS. *J Neurooncol*. 1992; 13(3):277-282.
20. Hoshino T, Ahn D, Prados M D, Lamborn K, Wilson C B. Prognostic significance of the proliferative potential of intracranial gliomas measured by bromodeoxyuridine labeling. *Int J Cancer*. 1993 1993; 53(4):550-555.
21. Ito S, Chandler K L, Prados M D, et al. Proliferative potential and prognostic evaluation of low-grade astrocytomas. *J Neuro-Oncol*. 1994 1994; 19(1):1-9.
22. Onda K, Davis R L, Shibuya M, Wilson C B, Hoshino T. Correlation between the bromodeoxyuridine labeling index and the MIB-1 and Ki-67 proliferating cell indices in cerebral gliomas. *Cancer*. 1994 1994; 74(7):1921-1926.
23. Kajiwara Y, Panchabhai S, Levin V A. A new preclinical 3-dimensional agarose colony formation assay. *Technol Cancer Res Treat*. August 2008; 7(4):329-334.
24. Kajiwara Y, Panchabhai S, Liu D D, Kong M, Lee J J, Levin V A. Melding a New 3-Dimensional Agarose Colony Assay with the E(max) Model to Determine the Effects of Drug Combinations on Cancer Cells. *Technol Cancer Res Treat*. April 2009; 8(2):163-176.
25. Levin V A, Panchabhai S C, Shen L, Kornblau S M, Qiu Y, Baggerly K A. Different changes in protein and phosphoprotein levels result from serum starvation of high-grade glioma and adenocarcinoma cell lines. *J Proteome Res*. January 2010; 9(1):179-191.
26. Levin V A, Panchabhai S, Shen L, Baggerly K A. Protein and phosphoprotein levels in glioma and adenocarcinoma cell lines grown in normoxia and hypoxia in monolayer and three-dimensional cultures. *Proteome Sci*. Jan. 25, 2012; 10(1):5.

Advantages of the Invention

Compositions according to the present invention can be administered to treat glioma, for example, by protecting against progression of anaplastic gliomas (especially anaplastic astrocytoma) to a more malignant phenotype, such as glioblastoma. These compositions are well-tolerated, do not produce significant side effects, and can be used together with other anti-neoplastic agents.

Compositions according to the present invention possess industrial applicability as pharmaceutical compositions, particularly for the treatment of glioma.

In some contexts, the composition claims of the present invention are directed to new ways of using an existing drug.

The inventions illustratively described herein can suitably be practiced in the absence of any element or elements, limitation or limitations, not specifically disclosed herein. Thus, for example, the terms "comprising," "including," "containing," etc. shall be read expansively and without limitation. Moreover, the term "comprising," as used herein, is intended also to encompass the terms "consisting essentially of" and "consisting essentially of" unless excluded. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein.

In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. The disclosures of all articles and references, including patent publications, are incorporated herein by reference.

3. The kit of claim 1, wherein the instructions describe preparing an eflornithine hydrochloride hydrate oral solution with a concentration of about 16.2 wt % to about 19.8 wt % in water.

4. The kit of claim 1, wherein the solid eflornithine hydrochloride hydrate is in the form of a powder.

5. The kit of claim 1, wherein the solid eflornithine hydrochloride hydrate is in the form of a tablet.

6. The kit of claim 1, wherein the one or more pouches further comprise a sweetening agent.

7. The kit of claim 6, wherein the one or more pouches comprise less than 1 wt % of the sweetening agent.

8. The kit of claim 7, wherein the sweetening agent is selected from the group consisting of an aspartame, dextran, dextrose, fructose, glycerol, mannitol, saccharin, calcium saccharin, sodium saccharin, sorbitol, sucrose, compressible sugar, confectioner's sugar, and syrup.

9. The kit of claim 8, wherein the sweetening agent is saccharin sodium dihydrate.

10. The kit of claim 1, wherein the pharmaceutically acceptable excipient is selected from the group consisting of maize starch, wheat starch, rice starch, potato starch, gelatin, gum, methyl cellulose, hydroxypropylmethyl-cellulose, sodium carboxymethylcellulose, or polyvinylpyrrolidone (PVP).

11. The kit of claim 10, wherein the pharmaceutically acceptable excipient is hydroxypropylmethyl-cellulose or polyvinylpyrrolidone.

12. The kit of claim 1, further comprising one or more additional pouches of solid eflornithine hydrochloride hydrate wherein each additional pouch comprises an individual dosage of eflornithine hydrochloride hydrate and a pharmaceutically acceptable excipient.

13. A method of preparing an oral solution of eflornithine hydrochloride hydrate, comprising adding the contents of a

What is claimed is:

1. A kit, comprising:
   a pouch of solid eflornithine hydrochloride hydrate wherein the pouch comprises an individual dosage of eflornithine hydrochloride hydrate and a pharmaceutically acceptable excipient; and
   instructions to prepare an oral solution of eflornithine hydrochloride hydrate.

2. The kit of claim 1, wherein the instructions describe preparing an eflornithine hydrochloride hydrate oral solution with a concentration of about 13.5 wt % to about 22.5 wt % in water.

pouch of the kit of claim 1 to water according to the instructions to make the oral solution.

14. A method of treating a subject with anaplastic astrocytoma, comprising administering a dose of an oral solution of eflornithine hydrochloride hydrate prepared with a pouch of the kit of claim 1 to a subject in need thereof.

15. The method of claim 14, comprising administering to the subject two or more doses of eflornithine hydrochloride hydrate per day.

16. The method of claim 14, wherein the eflornithine hydrochloride hydrate oral solution is administered for two weeks out of every three weeks.

* * * * *